US010125150B2

(12) United States Patent
Li et al.

(10) Patent No.: US 10,125,150 B2
(45) Date of Patent: Nov. 13, 2018

(54) CRYSTALLINE FORMS OF A PI3K INHIBITOR

(71) Applicant: Incyte Corporation, Wilmington, DE (US)

(72) Inventors: Yun-Long Li, Chadds Ford, PA (US); Brian W. Metcalf, Moraga, CA (US); Hui-Yin Li, Hockessin, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 15/980,400

(22) Filed: May 15, 2018

(65) Prior Publication Data

US 2018/0258105 A1 Sep. 13, 2018

Related U.S. Application Data

(62) Division of application No. 15/150,999, filed on May 10, 2016, now Pat. No. 9,988,401.

(60) Provisional application No. 62/159,726, filed on May 11, 2015.

(51) Int. Cl.
*C07D 519/00* (2006.01)
*C07D 473/34* (2006.01)
*C07D 513/04* (2006.01)

(52) U.S. Cl.
CPC ......... *C07D 519/00* (2013.01); *C07D 473/34* (2013.01); *C07D 513/04* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 3,037,980 A | 6/1962 | Hitchings et al. |
| 3,169,967 A | 2/1965 | Schittler |
| 3,506,643 A | 4/1970 | Thiel et al. |
| 3,862,189 A | 1/1975 | Schwender |
| 3,936,454 A | 2/1976 | Schwender |
| 3,962,443 A | 6/1976 | Minami et al. |
| 4,482,629 A | 11/1984 | Nakagawa et al. |
| 4,840,951 A | 6/1989 | Iwasaki et al. |
| 4,845,020 A | 7/1989 | Itoh et al. |
| 4,861,701 A | 8/1989 | Burns et al. |
| 5,124,331 A | 6/1992 | Arita et al. |
| 5,208,250 A | 5/1993 | Cetenko et al. |
| 5,252,580 A | 10/1993 | Takahashi et al. |
| 5,294,620 A | 3/1994 | Ratcliffe et al. |
| 5,314,883 A | 5/1994 | Tanikawa et al. |
| 5,459,132 A | 10/1995 | Bru-Magniez et al. |
| 5,521,184 A | 5/1996 | Zimmerman |
| 5,646,153 A | 7/1997 | Spada et al. |
| 5,811,439 A | 9/1998 | Ogawa et al. |
| 5,866,702 A | 2/1999 | Mackman et al. |
| 6,028,076 A | 2/2000 | Hirota et al. |
| 6,342,501 B1 | 1/2002 | Townsend et al. |
| 6,376,501 B1 | 4/2002 | Isobe et al. |
| 6,392,047 B1 | 5/2002 | Geissler et al. |
| 6,479,487 B1 | 11/2002 | Dumont et al. |
| 6,630,496 B1 | 10/2003 | Seehra et al. |
| 6,734,187 B1 | 5/2004 | Tanaka et al. |
| 6,828,344 B1 | 12/2004 | Seehra et al. |
| 7,129,264 B2 | 10/2006 | Smallheer et al. |
| 7,494,987 B2 | 2/2009 | Akada et al. |
| 7,495,002 B2 | 2/2009 | Langkopt et al. |
| 7,528,143 B2 | 5/2009 | Noronha et al. |
| 7,598,257 B2 | 10/2009 | Rodgers et al. |
| 7,612,114 B2 | 11/2009 | Hamaoka et al. |
| 8,680,108 B2 | 3/2014 | Li et al. |
| 8,759,359 B2 | 6/2014 | Combs et al. |
| 8,940,752 B2 | 1/2015 | Li et al. |
| 9,096,600 B2 | 8/2015 | Li et al. |
| 9,199,982 B2 | 12/2015 | Li et al. |
| 9,249,087 B2 | 2/2016 | Kozikowski et al. |
| 9,309,251 B2 | 4/2016 | Combs et al. |
| 9,434,746 B2 | 9/2016 | Li et al. |
| 9,527,848 B2 | 12/2016 | Li et al. |
| 9,707,233 B2 | 7/2017 | Li et al. |
| 9,730,939 B2 | 8/2017 | Li et al. |
| 9,815,839 B2 | 11/2017 | Li et al. |
| 9,944,646 B2 | 4/2018 | Combs et al. |
| 2003/0008898 A1 | 1/2003 | Mahboobi et al. |
| 2003/0157052 A1 | 8/2003 | Choe et al. |
| 2004/0058930 A1 | 3/2004 | Belema et al. |
| 2004/0063658 A1 | 4/2004 | Roberts et al. |
| 2004/0067964 A1 | 4/2004 | Matsuoka et al. |
| 2004/0142941 A1 | 7/2004 | Gudmundsson et al. |
| 2004/0209866 A1 | 10/2004 | Wang et al. |

(Continued)

FOREIGN PATENT DOCUMENTS

| AT | 388372 | 6/1989 |
| CA | 1066701 | 11/1979 |

(Continued)

OTHER PUBLICATIONS

"A to Z List of Cancers," National Cancer Institute (http://www.cancer.gov/)(Downloaded May 29, 2014), 22 pages.
"Angiogenesis" Merriam-Webster.com. Merriam-Webster, n.d. Web Jun. 16, 2014, www.merriam-webster.com/dictionary/angiogenesis, 3 pages.
"Arthritis: MedlinePlus Medical Encyclopedica," 2014, p. 1-5, accessed online Oct. 7, 2014; http://www.nlm.nih.gove/medlineplus/ency/article/001243.htm.
"Autoimmune disorders: MedlinePlus Medical Encyclopedia," 2013, p. 1-4, accessed online Oct. 7, 2014; http://www.nlm.nih.gov/medlineplus/ency/article/000816.htm.

(Continued)

*Primary Examiner* — Savitha M Rao
*Assistant Examiner* — Gregg Polansky
(74) *Attorney, Agent, or Firm* — Fish & Richardson P.C.

(57) ABSTRACT

The present invention is related to crystalline forms of (S)-7-(1-(9H-purin-6-ylamino)ethyl)-6-(3-fluorophenyl)-3-methyl-5H-thiazolo[3,2-a]pyrimidin-5-one which is a PI3K inhibitor useful in the treatment of cancer and other diseases.

31 Claims, 36 Drawing Sheets

(56) References Cited

U.S. PATENT DOCUMENTS

| | | |
|---|---|---|
| 2004/0242615 A1 | 12/2004 | Yamamori et al. |
| 2005/0043328 A1 | 2/2005 | Dolezal |
| 2005/0059677 A1 | 3/2005 | Alberti et al. |
| 2005/0107343 A1 | 5/2005 | Kasibhatla et al. |
| 2005/0165030 A1 | 7/2005 | Liu et al. |
| 2005/0261317 A1 | 11/2005 | Sadhu et al. |
| 2005/0267110 A1 | 12/2005 | Hirano et al. |
| 2005/0282831 A1 | 12/2005 | Beauglehole et al. |
| 2006/0025383 A1 | 2/2006 | Wishart et al. |
| 2006/0052403 A1 | 3/2006 | Isobe et al. |
| 2006/0074102 A1 | 4/2006 | Cusack et al. |
| 2006/0084687 A1 | 4/2006 | Boyce et al. |
| 2006/0166925 A1 | 7/2006 | Dolezal et al. |
| 2006/0247245 A1 | 11/2006 | Xu |
| 2006/0293334 A1 | 12/2006 | Fuji et al. |
| 2007/0060577 A1 | 3/2007 | Player et al. |
| 2007/0066624 A1 | 3/2007 | Zhou et al. |
| 2007/0167443 A1 | 7/2007 | Melikian et al. |
| 2007/0191395 A1 | 8/2007 | Kawakami et al. |
| 2007/0225303 A1 | 9/2007 | Ogita et al. |
| 2007/0275984 A1 | 11/2007 | Imogai et al. |
| 2008/0004269 A1 | 1/2008 | Xu et al. |
| 2008/0009508 A1 | 1/2008 | Szucova et al. |
| 2008/0014227 A1 | 1/2008 | Popa et al. |
| 2008/0114007 A1 | 5/2008 | Player et al. |
| 2008/0161332 A1 | 7/2008 | Bissantz et al. |
| 2008/0194616 A1 | 8/2008 | Liu et al. |
| 2008/0249155 A1 | 10/2008 | Gong et al. |
| 2008/0287469 A1 | 11/2008 | Diacovo et al. |
| 2008/0293739 A1 | 11/2008 | Trede |
| 2008/0306093 A1 | 12/2008 | Servant et al. |
| 2009/0023729 A1 | 1/2009 | Nakamura et al. |
| 2009/0047249 A1 | 2/2009 | Graupe et al. |
| 2009/0053192 A1 | 2/2009 | Millan et al. |
| 2009/0074884 A1 | 3/2009 | Chesney et al. |
| 2009/0118263 A1 | 5/2009 | Hashimoto et al. |
| 2009/0137581 A1 | 5/2009 | Chen et al. |
| 2009/0163545 A1 | 6/2009 | Goldfarb |
| 2009/0170879 A1 | 7/2009 | Szucova et al. |
| 2009/0253717 A1 | 10/2009 | Brown et al. |
| 2009/0325930 A1 | 12/2009 | Hamaoka et al. |
| 2010/0010059 A1 | 1/2010 | Yeh et al. |
| 2010/0035756 A1 | 2/2010 | Luthy et al. |
| 2010/0105683 A1 | 4/2010 | Keegan et al. |
| 2010/0190819 A1 | 7/2010 | Kanner |
| 2010/0240537 A1 | 9/2010 | Spichal et al. |
| 2010/0256118 A1 | 10/2010 | Isobe et al. |
| 2010/0298334 A1 | 11/2010 | Rodgers et al. |
| 2010/0298351 A1 | 11/2010 | Konakanchi et al. |
| 2011/0015212 A1 | 1/2011 | Li et al. |
| 2011/0028715 A1 | 2/2011 | Isobe et al. |
| 2011/0059951 A1 | 3/2011 | Rodgers et al. |
| 2011/0098248 A1 | 4/2011 | Halcomb et al. |
| 2011/0105508 A1 | 5/2011 | Allen et al. |
| 2011/0166164 A1 | 7/2011 | Brewster |
| 2011/0183985 A1 | 7/2011 | Li et al. |
| 2011/0190319 A1 | 8/2011 | Combs et al. |
| 2011/0224155 A1 | 9/2011 | Tachdjian et al. |
| 2011/0224190 A1 | 9/2011 | Huang et al. |
| 2011/0281884 A1 | 11/2011 | Combs et al. |
| 2011/0312979 A1 | 12/2011 | Li et al. |
| 2012/0149681 A1 | 6/2012 | Rodgers et al. |
| 2012/0149682 A1 | 6/2012 | Rodgers et al. |
| 2012/0157430 A1 | 6/2012 | Li et al. |
| 2013/0018034 A1 | 1/2013 | Yao et al. |
| 2013/0029982 A1 | 1/2013 | Castro et al. |
| 2013/0045963 A1 | 2/2013 | Rodgers et al. |
| 2013/0059835 A1 | 3/2013 | Li et al. |
| 2013/0261101 A1 | 10/2013 | Combs et al. |
| 2014/0005166 A1 | 1/2014 | Rodgers et al. |
| 2014/0031355 A1 | 1/2014 | Fisher et al. |
| 2014/0057912 A1 | 2/2014 | Combs et al. |
| 2014/0066448 A1 | 3/2014 | Combs et al. |
| 2014/0121198 A1 | 5/2014 | Li et al. |
| 2014/0121222 A1 | 5/2014 | Li et al. |
| 2014/0249132 A1 | 9/2014 | Li et al. |
| 2014/0275127 A1 | 9/2014 | Combs et al. |
| 2014/0343030 A1 | 11/2014 | Li et al. |
| 2015/0284390 A1 | 10/2015 | Li et al. |
| 2015/0361094 A1 | 12/2015 | Li et al. |
| 2016/0022685 A1 | 1/2016 | Li et al. |
| 2016/0024117 A1 | 1/2016 | Li et al. |
| 2016/0257689 A1 | 9/2016 | Qiao et al. |
| 2016/0264580 A1 | 9/2016 | Combs et al. |
| 2016/0362424 A1 | 12/2016 | Li et al. |
| 2016/0362425 A1 | 12/2016 | Li et al. |
| 2016/0362426 A1 | 12/2016 | Zhou et al. |
| 2017/0050987 A1 | 2/2017 | Li et al. |
| 2017/0158696 A1 | 6/2017 | Li et al. |

FOREIGN PATENT DOCUMENTS

| | | |
|---|---|---|
| DE | 1770420 | 11/1971 |
| DE | 2139107 | 2/1973 |
| EP | 255085 | 2/1988 |
| EP | 464612 | 1/1992 |
| EP | 481614 | 4/1992 |
| EP | 1138328 | 11/2001 |
| EP | 1109805 | 12/2003 |
| EP | 1783114 | 5/2007 |
| EP | 1972631 | 9/2008 |
| EP | 2031037 | 3/2009 |
| EP | 2050749 | 4/2009 |
| EP | 934307 | 4/2011 |
| GB | 1440478 | 6/1976 |
| GB | 1472342 | 5/1977 |
| JP | 50111080 | 9/1975 |
| JP | 53059663 | 5/1978 |
| JP | 53092767 | 8/1978 |
| JP | 56025234 | 6/1981 |
| JP | 56123981 | 9/1981 |
| JP | 58083698 | 5/1983 |
| JP | 62103640 | 5/1987 |
| JP | 62245252 | 10/1987 |
| JP | 1250316 | 10/1989 |
| JP | 4190232 | 7/1992 |
| JP | 9087282 | 3/1997 |
| JP | 9176116 | 7/1997 |
| JP | 10025294 | 1/1998 |
| JP | 10231297 | 9/1998 |
| JP | 2000080295 | 3/2000 |
| JP | 2000281654 | 10/2000 |
| JP | 2001151771 | 6/2001 |
| JP | 2005035924 | 2/2005 |
| JP | 2009080233 | 4/2009 |
| JP | 2009120686 | 6/2009 |
| JP | 2011511761 | 4/2011 |
| JP | 2011136925 | 7/2011 |
| RU | 2233842 | 8/2004 |
| SU | 1712359 | 2/1992 |
| WO | WO 1993/16076 | 8/1993 |
| WO | WO 1993/22291 | 11/1993 |
| WO | WO 1993/25524 | 12/1993 |
| WO | WO 1999/43651 | 9/1999 |
| WO | WO 1999/43672 | 9/1999 |
| WO | WO 2000/09495 | 2/2000 |
| WO | WO 2000/044750 | 8/2000 |
| WO | WO 2000/053595 | 9/2000 |
| WO | WO 2001/014402 | 3/2001 |
| WO | WO 2001/064639 | 9/2001 |
| WO | WO 2001/064655 | 9/2001 |
| WO | WO 2001/072709 | 10/2001 |
| WO | WO 2002/000196 | 1/2002 |
| WO | WO 2002/006477 | 1/2002 |
| WO | WO 2002/024685 | 3/2002 |
| WO | WO 2002/064599 | 8/2002 |
| WO | WO 2002/066478 | 8/2002 |
| WO | WO 2002/078701 | 10/2002 |
| WO | WO 2003/020721 | 3/2003 |
| WO | WO 2003/024967 | 3/2003 |
| WO | WO 2003/029209 | 4/2003 |
| WO | WO 2003/037347 | 5/2003 |
| WO | WO 2003/044014 | 5/2003 |
| WO | WO 2003/049678 | 6/2003 |

(56) References Cited

FOREIGN PATENT DOCUMENTS

| | | |
|---|---|---|
| WO | WO 2003/050064 | 6/2003 |
| WO | WO 2003/068750 | 8/2003 |
| WO | WO 2003/074497 | 9/2003 |
| WO | WO 2003/099771 | 12/2003 |
| WO | WO 2004/005281 | 1/2004 |
| WO | WO 2004/024693 | 3/2004 |
| WO | WO 2004/046120 | 6/2004 |
| WO | WO 2004/048365 | 6/2004 |
| WO | WO 2004/056786 | 7/2004 |
| WO | WO 2004/069256 | 8/2004 |
| WO | WO 2004/076455 | 9/2004 |
| WO | WO 2004/080980 | 9/2004 |
| WO | WO 2004/087704 | 10/2004 |
| WO | WO 2004/107863 | 12/2004 |
| WO | WO 2004/113335 | 12/2004 |
| WO | WO 2005/000309 | 1/2005 |
| WO | WO 2005/016528 | 2/2005 |
| WO | WO 2005/028444 | 3/2005 |
| WO | WO 2005/046578 | 5/2005 |
| WO | WO 2005/091857 | 10/2005 |
| WO | WO 2005/113556 | 12/2005 |
| WO | WO 2006/008523 | 1/2006 |
| WO | WO 2006/030031 | 3/2006 |
| WO | WO 2006/056399 | 6/2006 |
| WO | WO 2006/068760 | 6/2006 |
| WO | WO 2006/089106 | 8/2006 |
| WO | WO 2007/002701 | 1/2007 |
| WO | WO 2007/012724 | 2/2007 |
| WO | WO 2007/042806 | 4/2007 |
| WO | WO 2007/076092 | 7/2007 |
| WO | WO 2007/087548 | 8/2007 |
| WO | WO 2007/095588 | 8/2007 |
| WO | WO 2007/102392 | 9/2007 |
| WO | WO 2007/114926 | 10/2007 |
| WO | WO 2007/126841 | 11/2007 |
| WO | WO 2008/002490 | 1/2008 |
| WO | WO 2008/005303 | 1/2008 |
| WO | WO 2008/025821 | 3/2008 |
| WO | WO 2008/032033 | 3/2008 |
| WO | WO 2008/064018 | 5/2008 |
| WO | WO 2008/064157 | 5/2008 |
| WO | WO 2008/082490 | 7/2008 |
| WO | WO 2008/097991 | 8/2008 |
| WO | WO 2008/100867 | 8/2008 |
| WO | WO 2008/116129 | 9/2008 |
| WO | WO 2008/118454 | 10/2008 |
| WO | WO 2008/118468 | 10/2008 |
| WO | WO 2009/026701 | 3/2009 |
| WO | WO 2009/034386 | 3/2009 |
| WO | WO 2009/062118 | 5/2009 |
| WO | WO 2009/063235 | 5/2009 |
| WO | WO 2009/081105 | 7/2009 |
| WO | WO 2009/085230 | 7/2009 |
| WO | WO 2009/086123 | 7/2009 |
| WO | WO 2009/097446 | 8/2009 |
| WO | WO 2009/128520 | 10/2009 |
| WO | WO 2009/130560 | 10/2009 |
| WO | WO 2009/140215 | 11/2009 |
| WO | WO 2009/151972 | 12/2009 |
| WO | WO 2010/006234 | 1/2010 |
| WO | WO 2010/008739 | 1/2010 |
| WO | WO 2010/018458 | 2/2010 |
| WO | WO 2010/036380 | 4/2010 |
| WO | WO 2010/057048 | 5/2010 |
| WO | WO 2010/074588 | 7/2010 |
| WO | WO 2010/075068 | 7/2010 |
| WO | WO 2010/092340 | 8/2010 |
| WO | WO 2010/114900 | 10/2010 |
| WO | WO 2010/118367 | 10/2010 |
| WO | WO 2010/123931 | 10/2010 |
| WO | WO 2010/127208 | 11/2010 |
| WO | WO 2010/129816 | 11/2010 |
| WO | WO 2010/151735 | 12/2010 |
| WO | WO 2010/151740 | 12/2010 |
| WO | WO 2011/001052 | 1/2011 |
| WO | WO 2011/002708 | 1/2011 |
| WO | WO 2011/002817 | 1/2011 |
| WO | WO 2011/008302 | 1/2011 |
| WO | WO 2011/008487 | 1/2011 |
| WO | WO 2011/011550 | 1/2011 |
| WO | WO 2011/025889 | 3/2011 |
| WO | WO 2011/048082 | 4/2011 |
| WO | WO 2011/055215 | 5/2011 |
| WO | WO 2011/058111 | 5/2011 |
| WO | WO 2011/058113 | 5/2011 |
| WO | WO 2011/058474 | 5/2011 |
| WO | WO 2011/069294 | 6/2011 |
| WO | WO 2011/075628 | 6/2011 |
| WO | WO 2011/075630 | 6/2011 |
| WO | WO 2011/075643 | 6/2011 |
| WO | WO 2011/092198 | 8/2011 |
| WO | WO 2011/117711 | 9/2011 |
| WO | WO 2011/123751 | 10/2011 |
| WO | WO 2011/130342 | 10/2011 |
| WO | WO 2011/146882 | 11/2011 |
| WO | WO 2011/156759 | 12/2011 |
| WO | WO 2011/163195 | 12/2011 |
| WO | WO 2012/003262 | 1/2012 |
| WO | WO 2012/003271 | 1/2012 |
| WO | WO 2012/003274 | 1/2012 |
| WO | WO 2012/040634 | 3/2012 |
| WO | WO 2012/061696 | 5/2012 |
| WO | WO 2012/064973 | 5/2012 |
| WO | WO 2012/068343 | 5/2012 |
| WO | WO 2012/080729 | 6/2012 |
| WO | WO 2012/087784 | 6/2012 |
| WO | WO 2012/087881 | 6/2012 |
| WO | WO 2012/097000 | 7/2012 |
| WO | WO 2012/125629 | 9/2012 |
| WO | WO 2012/135009 | 10/2012 |
| WO | WO 2013/033569 | 3/2013 |
| WO | WO 2013/052699 | 4/2013 |
| WO | WO 2013/151930 | 10/2013 |
| WO | WO 2015/191677 | 12/2015 |
| WO | WO 2016/138363 | 9/2016 |
| WO | WO 2016/183060 | 11/2016 |
| WO | WO 2016/183062 | 11/2016 |

OTHER PUBLICATIONS

"Adult Acute Myeloid Leukemia Treatment (PDQ®)—Patient Version, Last Modified Jul. 30, 2012," National Cancer Institute, [retrieved from the internet on Nov. 26, 2012] at http://www.cancer.gov/cancertopics/pdq/treatment/adultAML/Patient/page1, 5 pgs.

Ali, et al., "Essential Role for the p110δ phosphoinositide 3-kinase in the allergic response," Nature. 2004, 431 (7011):1007-11.

Allen, et al., "Synthesis of C-6 substituted pyrazolo[1,5-a]pyridines with potent activity against herpesviruses," *Bioorganic & Medicinal Chemistry* (2006), 14(4), 944-954.

Apsel et al., "Targeted polypharmacology: discovery of dual inhibitors of tyrosine and phosphoinositide kinases," Nat. Chem. Biol., 2008, 4(11):691-699.

Badger, et al., "Cancer-specific mutations in PIK3CA are oncogenic in vivo," Proc Natl Acad Scie U S A. 2006, 103(5):1475-9.

Baek et al., "Complete Remission induced by rituximab in refractory, seronegative, muscle-specific, kinase-positive myasthenia gravis," J Neurol Neurosurg Psychiatry, 2007, 78(7):771.

Ball, "PI3K inhibitors as potential therapeutics for autoimmune disease," Drug Discovery Today, 2014, pp. 1195-119.

Barber, et al., "PI3Kγ inhibition block gloerulonephritis and extends lifespan in mouse model fo systemic lupus," Nat Med. 2005, 11(9):933-5.

Barragan et al., "Protein Kinases in the Regulation of Apoptosi in B-cell Chronic Lymphocytic Leukemia," *Leukemia and Lymphoma*, 2003, 44(11):1865-1870.

Belema, et al., "Synthesis and structure-activity relationship of imidazo(1,2-a)thiebi(3,2-e)pyrazines as IKK-β inhibitors," *Bioorganic & Medicinal Chemistry Letters* (2007), 17(15), 4284-4289.

Bendell, J.C., "Phase I, dose-escalation study of BKM120, an oral pan-Class I PI3K inhibitor, in patients with advanced solid tumors," Journal of Clinical Oncology (2011): JCO-2011.

(56) References Cited

OTHER PUBLICATIONS

Benistant, et al., "A specific function for phosphatidylinositol 3-kinase α (p85α-p110α) in cell survival and for phosphatidylinositol 3-kinase β (p85α-p110β) in de novo DNA synthesis of Human Colon carcinoma cells," Oncogene, 2000, 19(44):5083-90.
Bennasar, et al., "Generation and Intermolecular Reactions of 2-Indolylacyl Radicals," *Organic Letters* (2001), 3(11), 1697-1700, CODEN: ORLEF7; ISSN: 1523-7060.
Berge et al., "Pharamceutical Salts," J Pharma Sci, 1977, 66(1):1-19.
Bergman, et al., "Synthesis of indolocarbazole quinones; potent aryl hydrocarbon receptor ligands," *Tetrahedron* (2002), 58(7), 1443-1452.
Bhatia and Rose, "Autoimmunity and autoimmune disease," Principles of Med Biol., 1996, 6:239-263, 244.
Bhovi, et al., "1,3-dipolar cycloaddition reaction: Synthesis and antimicrobial activity of some new3-ethoxycarbonyl-5-methoxy-6-bromo-2-triazolylmethylindoles," *Indian Journal of Heterocyclic Chemistry* (2004), 14(1), 15-18 CODEN: IJCHEI; ISSN: 0971-1627.
Billottet, et al., "A selective inhibitor of the p110δ isoform of PI 3-kinase inhibits AML cell proliferation and survival and increases the cytotoic effects of VP16," Oncogene. 2006, 25(50):6648-59.
Biswas, et al., "Synthesis of trifluoromthylindolocarbazole, novel cyclic 27- and 36-membered N-benzyltri- and -tetraindoles, and an N-benzyltetraindolyltrimethane," *Monatshefte fuer Chemie* (1999), 130(10), 1227-1239, CODEN: MOCMB7; ISSN: 0026-9247.
Blom et al., Preparative LC-MS Purification: Improved Compund Specific Method Optimization, J. Combi. Chem. 2004, 6(6), 874-883.
Blom et al., "Two-Pump at Column Dilution Configuration for Preparative LC-MS," 2002, 4: 295.
Blom et al., "Optimizing Preparative LC-MS Configurations and Methods for Parallel Synthesis Purification," 2003, 5:670.
Boger, et al., "FIrst and Second Generation Total Synthesis of the Teicoplanin Aglycon," JACS, 123(9), 1862-1871, 2001.
Brachmann et al., "PI3K and mTOR inhibitors—a new generation of targeted anticancer agents," Current Opinion Cell Biol., 2009, 21:194-198.
Bringmann, et al., "Novel concepts in directed biaryl synthesis. Part 65. Synthesis and structure of a novel twofold lactone-bridged ternaphthyl," *Tetrahedron Letters* (1998), 39(12), 1545-1548 CODEN: TELEAY; ISSN: 0040-4039.
Brock et al., "Roles of Gβγ in membrane recruitment and activation of p110γ/p101 phosphoinositide 3-kinaseγ," J Cell Biol., 2003, 160(1):89-99.
Brown, et al., "Small molecule inhibitors of IgE synthesis," *Bioorganic & Medicinal Chemistry Letters* (2006), 16(17), 4697-4699.
Cacoub et al., "Anti-CD20 monoclonal antibody (rituximab) treatment for cryoglobulinemic vasculitis: where do we stand?," Ann Rheum Dis, Mar. 2008, 67: 283-287.
Camps, et al., "Blockaed of PI3kγ suppresses joint inflammation and damage in mouse models of rheumatoid arthritis," Nat Med. 2005, 11(9):936-43.
Canadian Examination Report in Canadian Application No. 2,766,100, dated Jan. 31, 2017, 3 pages.
Cannon, Burger's Medicinal Chemistry and Drug Discovery, Fifth Edition, vol. 1 Principles and Practice, Wiley-Interscience 1995, Ch. 19, pp. 785-803, 784.
Cantley, "The Phosphoinositide 3-Kinase Pathway," Science, (2002) 296 (5573):1655-7.
Castillo-Trivino, et al., "Rituximab in relapsing and progressive forms of multiple sclerosis: a systematic review," The PLoS One. Jul. 2013; 8(7):e66308.doi: 10.1371/journal.pone.0066308. Print 2013.
Chai, et al., "Synthesis and in vitro anti-hepatitis B virus activities of some ethyl 6-bromo-5-hydroxy-1H-indole-3-carboxylates," *Bioorganic & Medicinal Chemisty* (2006), 14(4), 911-917.
Chang, K-Y., "Novel phosphoinositide 3-kinase/mTOR dual inhibitor, NVP-BGT226, displays potent growth-inhibitory activity against human head and neck cancer cells in vitro and in vivo," Clinical Cancer Research 17.22 (2011): 7116-7126.
Chen, X., "Targeting oxidative stress in embryonal rhabdomyosarcoma," Cancer cell 24.6 (2013): 710-724.
Clayton, et al., "A Crucial Role for the p110δ Subunit of Phosphatidylinositol 3-Kinase in B Cell Development and Activiations," J Exp Med. 2002, 196(6):753-63.
Collins et al., "Rituximab treatment of fibrillary glomerulonephritis," Am J Kidney Dis., 2008, 52(6):1158-62.
Coughlin et al., Approaches and limitations of phosphatidylinositol-3-kinase-pathway activation status as a predictive biomarker in the clinical development of targeted theraphy, Breast Cancer Res Treatment, 2010, 124:1-11.
Courtney et al., "The PI3K Pathway as Drug Target in Human Cancer," J Clinc Oncol., 2010, 29:1075-1083.
Crabbe, "The PI3K inhibitor arsenal: choose your weapon!" Trends Biochem Sci., 2007, 32(10):450-56.
Dagia et al., A preferential pp110α/ γPI3K inhibitor attenuates experimental inflammation by suppressing the production of proinflammatory mediators in a NF-κB-dependent manner, Am J Physiol—Cell Physiol., 2010, 298:929-941.
DeBeradinis et al., "The Biology of Cancer: Metabolic Reprogramming Fuels Cell Growth and Proliferation," Cell Metabolism, Jan. 2008, 7:11-20.
Delmas and Meunier, "The Management of Paget's Disease of Bone," N Engl J Med., 1997, 336:558-566.
Devauchelle-Pensec, "Threatment of Primary Sjorgren Syndrome with Rituximab," Annal Internal Med., 2014, 160:233-242.
Dolezal et al., "Preparation and biological activity of 6-benzylaminopurine derivatives in plants and human cancer cells," *Bioorganic & Medicinal Chemistry* (2006), 14(3), 875-884.
Dolezal et al., "Preparation, biological activity and endogenous occurrence of N6-benzyladenosines," *Bioorganic & Medicinal Chemistry* (2007), 15(11), 3737-3747.
Dorokhov, et al., "Synthesis of Functionalized pyrimidine-4-thiones and pyrido[2,3-d]pyrimidin-5-one derivatives form aminals of monoacylketenes", Izvestiya Akademii Nauk, Seriya Khimichekaya (1993), (11), 1932-7.
Doukas et al., "Aerosolize Phophoinositide 3-Kinase γ/δ Inhibitor TG100-115 [3-[2,4-Diamino-6-(3-hydroxyphyl)pteridin-7-yl]phenol]as a Therapeutic Candidate for Asthma and Chronic Obstructive Pulmonary Disease," The Journal of Pharmacology and Experimental Therapeutics, 328(3):758-765, 2009.
Dushianthan et al., "Acute respiratory distress syndrome and acute lung injury," Post Graduate Med J., 2011, 87:612-622.
Engelman, "Targeting PI3K signalling in cancer: opportunities, challenges and limitations," Nature Rev: Camcer, 2009, 9:550-562.
Fadeyeva, et al., "Inhibitors of early virus-cell interaction stages among 3-ethoxycarbonyl-5-hydroxy-bromoindole derivatives," *Khimiko-Farmatsevticheskii Zhurnal* (1992), 26(9-10), 17-20 (with English abstract).
Fine et al., "Neoplasms of the Central Nervous System," Cancer Principles Practice Oncol., 2005, 2:1834-1887.
Flinn et al., "Preliminary evidence of clinical activity in a phase I study of CAL-101, a selective inhibitor of the p110δ isoform of phosphatidylinositol 3-kinase (PI3K), in patients with select hematolofic malignancies," Journal of Clinical Oncology, (abstract), 27(15S):3543, 2009.
Floberg et al., "Extractive alkylation of 6-mercaptopurine and determination in plasma by gas chromatography-mass spectrometry," *Journal of Chromatograhpy, Biomedical Applications*, (1981), 225(1),73-81.
Fruman and Bismuth, "Fine Tuning he immune Response with PI3K," *Immunological Revs.*, 2006, 228:253-272.
Garvey, "Rituximab in the treatment of autimmune haematologoical disorders," British Journal of Haematology, 2008, 141: 149-169.
Gati et al., "(125I)Iodohydroxynitrobenzylthioinosine: a new high-affinity nucleoside transporter probe," *Biochemistry and Cell Biology* (1987), 65(5), 467-73.
Geng, et al., "Exploring 9-benzyl purines as inhibitors of glutamate racemase (MurI) in Gram-positive bacteria", Bioorganic & Medicinal Chemistry Letters (2008), 18(15), 4368-4372.

(56) References Cited

OTHER PUBLICATIONS

Ghigo et al., "PI3K inhibition in inflammation: Toward tailored therapies for specific disease," BioEssays, 2010, 32:185-196.
Godeau et al., "Rituximab efficacy and safety in adult splenectomy candidates with chronic immune thrombocytopenic purpura: results of a prospective multicenter phase 2 study," Blood, 2008, 112(4): 999-1004.
Golantsov, et al., "Chirally N-substituted indole-2-carbaldehydes. Preparation and use in asymmetric synthesis," *Chemistry of Heterocyclic Compounds* (New York, NY, United States) (2005), 41(10), 1290-1299.
Granik, "Acetals of lactams and amides of acids. 40. synthesis and hydrolytic splitting of mono- and bicyclic derivatives of 4-pyrimidinone", Khimiya Geterotsiklicheskikh Soedinenii (1984), (4), 532-7 (with English abstract).
Greene and P. G. M. Wuts, Protective Groups in Organic Synthesis, 3rd ed., Wiley & Sons, Inc., New York (1999)*Too Voluminous to Provide.
Wuts and Green, Protective Groups in Organic Synthesis, 4th ed., John Wiley & Sons: New Jersey, pp. 696-887,2007.
Harley, "Medical Management of Actue Renal Failure," Renal Failure Replacement Therapies, 2008, pp. 26-32.
Harris et al., "Alkyl 4-Chlorobenzoyloxycarbamates as Highly Effective Nitrogen Source Reagents for the Base-Free, Intermolecular Aminohydroxylation Reaction," J. Org. Chem., 76, 358-372, 2011.
Hauser et al., "B-Cell Depletion with Rituximab in Relapsing-Remitting Multiple Sclerosis," The New England Journal of Medicine, 358(7):676-688, 2008.
Hayter and Cook, "Updated assessment of the prevalence, spectrum and case definition of autoimmune disease," Autoimmunity reviews, 2012, 11:754-765.
Hickey, et al., "BCR-ABL Regulates Phosphatidylinositol 3-Kinase-p110γTranscription and Activation and is Required for Proliferation and Drug Resistance," J Biol Chem. 2006, 281(5):2441-50.
Hirose, et al., "Pyridone-carboxylic acids as antibacterial agents. I. Synthesis and antibacterial activity of 1-alkyl-1,4-dihydro-4-oxo-1,8- and -,6-naphthyridine-3-carboxylic acids", Chemical & Pharmaceutical Bulletin (1982), 30(7), 2399-409.
Hirota, "Effiecient Synthesis of 2,9-disubstituted 8-hydroxyadenine derivatives", Organic & Biomolecular Chemistry (2003), 1(8), 1354-1365.
Hirsch et al., "Taming the PI3K team to hold inflammation and cancer at bay," Pharmacology & Therapeutics, 2008, 118: 192-205.
Hosalkar et al., "Skeletal Trauma and Common Orthopedic Problems," Chpt 10, Khurana (ed.) Bone Pathology, 2009, 93 pages.
Huang et al., "Design and synthesis of pyrido[2,3-d]pyrimidin-5-one class of anti-inflammatory FMS inhibitors,", *Bioorganic & Medicinal Chemistry Letters* (2008), 18(7), 2355-2361.
Huang et al., "Synthesis and bioassay of fluorine-containing cytokinin, N6-pentafluoro-benzyladenosine," *Youji Huaxue* (1988), 8(2), 147-8 (with English abstract).
Ihle et al., "Inhibitors of phosphatidylinositol-3-kinase in cancer therapy", *Molecular Aspects of Medicine*, 31(2):135-144, 2010.
Irie, et al., "Discovery of selective and nonpeptidic cathepsin Sinhibitors," *Bioorganic & Medicinal Chemistry Letters* (2008), 18(14), 3959-3962.
Isobe, et al., "Synthesis and Biological Evaluation of Novel 9-Substituted-8-hydroxyadenine drivatives as Potent Interferon Inducers", Journal of Medicinal Chemistry (2006), 49(6),2088-2095.
Itaya, et al., "Syntheses of the marine ascidian purine aplidiamine and its 9-β-D-ribofuranoside," *Tetrahedron Letters* (1998), 39(26), 4695-4696.
Itaya, et al., "Synthesis and structure of the marine ascidian 8-oxoadenine aplidiamine," *Chemical & Pharmaceutical Bulletin* (1999), 47(9), 1297-1300.
Jager et al., "Molecular recognition. II Discrimination of speciic and non-specific intermolecular interactions by means of magnetic resonance spectroscopy," *Magnetic Resonance in Chemistry* (1998), 36(3), 205-210, CODEN: MRCHEG; ISSN: 0749-1581.

Jager, et al., "Molecular recognition analyzed by EPR, ENDOR, and NMR spectroscopy," *Angewandte Chemie*, International Edition in English (1996), 35(16), 1815-1818.
Japanese Office Action in Japanese Application No. 2014-528654, dated Mar. 29, 2016, 5 pages (English Translation).
Jimenez, et al., "The p85 Regulator Subunit Controls Sequential Activation of Phosphoinositide 3-Kinase by Tyr Kinases and Ras," J Biol Chem., 2002, 277(44):41556-62.
Jou, et al., "Essential, Nonredundant Role for the Phospoinositide 3-Kinase p110δ in Signaling by the B-Cell Receptor Complex," Mol Cell Biol. 2002, 22(24):8580-91.
Kang et al., "Aplidiamine, a unique zwitterionic benzyl hydroxyadenine from the Western Australian marine ascidian Aplidopsis sp.," *Tetrahedron Letters* (1997), 38(6), 941-944.
Kang, et al., "Phosphtidylinositol 3-kinase mutations identified in human cancer are concogenic," Proc Natl Acad Sci U S A. 2005, 102(3):802-7.
Karpouzas, et al., "Rituximab Therapy Induces Durable Remissions in Hispanic and African American Patients with Refractory Sytemic Lupus Erythematosus (SLE)," Presented at 73th Annual Scientific Meeting of the American College of Rheumatology, Oct. 2009; Philadelphia, PA.
Kasibhatla, "Rationally Designed High-Affinity 2-Amino-6halopurine Heat Shock Protein 90 Inhibitors That Exhibit Potent Antitumor Activity", Journal of Medicinal Chemistry (2007), 50(12),2767-2778.
Katritzky, et al., "Facile Synthesis of 2-Substituted Indoles and Indolo [3,2-b]carbazoles from 2-(Benzotriazol-1-ylmethyl)indole," *Journal of Organic Chemistry* (1995), 60(11), 3401-4.
Kim et al., "A signalling network in Phenylephrine-Induced Benign Prostatic Hyperplasia," Endocrinology, 2009-150:3576-3583.
Kim, et al., "A new structural class of S-adenosylhomocysteine hydrolase inhibitors", Bioorganic & Medicinal Chemistry (2009), 17(18), 6707-6714.
Kim, et al., "Synthesis and evaluation of antitumor activity of novel 1,4-naphthoquinone derivatives," *Archives of Pharmacal Research* (2006), 29(2), 123-130 CODEN: APHRDQ; ISSN: 0253-6269.
Knobbe, et al., "Genetic alteration and expression of the phosphoinositol-3-kinase/Akt pathway genes *PIK3CA* and *PIKE* in human glioblastomas," Neuropathol Appl Neurobiol. 2005, 31(5):486-90.
Kolasa, et al., "Synthesis of Indolylalkoxyiminoalkylcarboxylates as leukotriene biosynthesis inhibitors," *Bioorganic & Medicinal Chemistry* (1997), 5(3), 507-514.
Kolliputi and Waxman, "IL-6 cytoprotection in hyperoxic acute lung injury occurs via PI3K/Akt-mediated Bax phosphorylation," Am J Physiol Lung Cellular Mole Physiol., 2009, 297:L6-L16.
Kong and Yamori, "Phosphatidylinositol 3-kinase inhibitors: promising drug candidates for cancer theraphy," Cancer Sci., 2008, 9:1734-1740.
Kong and Yamorie, "Advances in Development of Phosphatidylinositol 3-Kinase Inhibitors," Current Medicinal Chemistry, 16:2839-2854, 2009.
Kuduk et al., "Heterocyclic fused pyridone carboxylic acid M1 positive allosteric modulators," *Bioorganic & Medicinal Chemistry Letters* (2010), 20(8), 2533-2537.
Kung et al., "Characterization of a Murine Model of Allergic Pulmonary Inflammation," Int. Arch. Allergy Immunol., (abstract), 105(1):83-90, 1994.
Kurimoto, et al., "Synthesis and Biological Evaluation of 8-Oxoadenine Derivatives as Toll-like Receptor 7 Agonists Introducing the Antedrug Concept", *Journal of Medicinal Chemistry* (2010), 53(7),2964-2972.
Kuster (ed), Kindase Inhibitors: Methods and Protocols Methods in Molecular Biology, 2012, 795:1-44.
Kutney, et al., "Dihydropyridines in synthesis and biosynthesis. IV. Dehydrosecodine, in vitro precursor of indole alkaloids," *Canadian Journal of Chemistry* (1982), 60(11), 1269-78.
Lee, et al., "Inhibition of phosphoinositide 3-kinase δ attenuates allergic airway inflammation and hyperresponsiveness in murine model," FASEB J. 2006, 20(3):455-65.

(56) References Cited

OTHER PUBLICATIONS

Li et al., "Design, synthesis and antitumor activities of novel 4-anilino-5H-pyridazino[4,5-b]indoles," *Zhongnan Yaoxue* (2008), 6(2), 144-148, CODEN: ZYHAC; ISSN: 1672-2981, Publisher: Zhongnan Yaoxue Zazhishe (with English abstract within the article).

Li et al., "Synthesis and antitumor activities of novel 1-anilino 5-pyridazino[4,5-b]indoles," *Zhongguo Yaowu Huaxue Zazhi* (2007), 17(6), 339-343, CODEN: ZYHZEF; ISSN: 1005-0108 (with English abstract within the article).

Li, et al., "Optimization of the heterocyclic core of the quinazolinone-derived CXCR3 antagonists," *Bioorganic & Medicinal Chemistry Letters* (2008), 18(2), 688-693.

Li, et al., "Synthesis and anti-tumor activities of a novel series of tricyclic 1-anilino-5H-pyridazino[4,5-B]indoles," *Archiv der Pharmazie* (Weinheim, Germany) (2007), 340(8), 424-428, CODEN: ARPMAS; ISSN: 0365-6233.

Lindsay, et al., "SmI2-Promoted Radical Addition Reactions with N-(2-Indolylacyl)oxazolidinones: Synthesis of Bisindole Compounds," *Journal of Organic Chemistry* (2007), 72(11), 4181-4188, CODEN: JOCEAH; ISSN:0022-3263.

Link, J. T., "The intramolecular Heck Reaction," *Organic Reactions* (Hoboken, NJ, United States) (2002), 60, No pp. given CODEN: ORHNBA URL: http://www3.interscience.wiley.com/cgi-bin/mrwhome/107610747/HOME.

Lipsky, "Systemic lupus erythematosus: an autoimmune disease of B cell hyperactivity," Nat Immunol., 2001, 2(9):761-6.

Liu et al., "Inhibition of the mitotic kinesin Eg5 up-regulates Hsp70 through the phosphatidylinositol 3-kinase/Akt pathway in multiple myeloma cells," J Biol Chem., 2006, 281(26):18090-18097.

Liu et al., "mTOR mediated anti-cancer drug discovery," Drug Discovery Today: Therapeutic Stategies, 2009, 6:47-55.

Lovric et al., "Rituximab as rescue therapy in anti-neutrophil cytoplasmic antibody-associated vasculitis: a single-centre expereince with 15 patients," Nephrol Dial Transplant, 2009, 24: 179-185.

Lucas, et al., "Rauwolfia alkaloids. XXXI. The synthesis and activity of some reserpine analogs," *Journal of the American Chemical Society* (1959), 81, 1928-32.

Luo et al., "Principles of Cancer Therapy: Oncogene and Non-oncogene Addiction," Cell, 2009, 36:823-837.

Ma, et al., "Bromophenols Coupled with Nucleoside Bases and Brominated Tetrahydroisoquinolines from the Red Alga Rhodomela confervoides", Journal of Natural Products (2007), 70(3), 337-341.

Ma, et al., "Two new constituents from Artemisia capillaris Thunb", Molecules (2008), 13(2), 267-271.

Mahboobi, et al., "Bis(1H-2-indolyl)methanones as a Novel Class of Inhibitors of the Platelet-Derived Growth Factor Receptor Kinase," Journal of Medicinal Chemistry (2002), 45(5):1002-1018.

Martelli et al., "Targeting the PI3K/AKT/mTOR signaling network in acute myelogenous leukemia," Expert Opin Investig Drugs. Sep. 2009;18(9):1333-49.

Matsumoto, et al., "Pyrido[2,3-d]pyrimidine antibacterial agents. 3. 8-Alkyl- and 8-vinyl-5,8-dihydro-5-oxo-2-(1-piperazinyl)pyrido[2,3-d]pyrimidine-6-carboxylic acids and their derivatives", *J Medicinal Chem* (1975), 18(1), 74-9.

McDermott and Settleman, "Personalized Cancer Theraphy with Selective Kinase Inhibitors: An Emerging Paradigm in Medical Oncology," J Clinical Oncol., 2009,27:5650-5659.

McLean, et al., "Discovery of covalent inhibitors for MIF tautomerase via cocrystal structures with phantom hits from virtual screening," *Bioorganic & Medicinal Chemistry Letters* (2009), 19(23), 6717-6720.

McMahon, G., "VEGF Receptor Signaling in Tumor Angiogenesis," The Oncologist, 5(1):3-10, 2000.

Meade, et al., "Anxiolytic activity of analogs of 4-benzylamino-2-methyl-7H-pyrrolo[2,3-d]pyrimidines," *European Journal of Medicinal Chemistry* (1998), 33(5), 363-374.

MedicineNet.com' [online]. "Definition of Cancer," Sep. 18, 2004, retrieved on Sep. 16, 2005. Retrieved from the Internet: http://www.medterms.com, 1 page.

Medpagetoday.com' [online] "Current Role of Rituximab in Systematic Lupus," Jan. 2015, [retrieved Apr. 23, 2015]. Retrieved from the Internet: URL <http://www.medpagetoday.com/Rheumatology/Lupus/49398#./49398?&_suid=14297429843880910545130428968­4>. 10 pages.

Meijer et al., "Treatment of primary Sjögren syndrome with rituximab: extended follow-up, safety and efficacy of retreatment," Ann. Rheum. Dis., 68(2):284-285, 2009.

Medeot et al., "Rituximab therapy in adult patients with relapsed or refractory immune thrombocytopenic purpura: long-term follow-up results," European Journal of Haematology, 2008, 81: 165-169.

Merrill, "Efficacy and safety of rituximab in moderately-to-severely active systemic lupus erythematosus: The randomized, double-blind, phase ii/iii systemic lupus erythematosus evaluation of rituximab trial," Arthritis & Rheumatism, 2010, 61(1):222-233.

Miki, et al., "Reaction of 1-benzylindole-2,3-dicarboxylic anhydride with with 3-bromo-4-lithiopyridine: formal synthesis of ellipticine," *Heterocycles* (1998), 48(8), 1593-1597.

Miki, et al., "Reaction of indole-2,3-dicarboxylic anhydride with (3-bromo-4-pyridyl)triisopropoxytitanium: synthesis of ellipticine," *Tetrahedron Letters* (1996), 37(43), 7753-7754.

Miki, et al., "Synthesis of caulersin and its isomers by reaction of indole-2,3-dicarboxylic anhydrides with methyl indoleacetates," *Tetrahedron Letters* (2006), 47(29), 5215-5218, CODEN: TELEAY; ISSN: 0040-4039.

Miki, et al., "Sythesis of ellipticine by reaction of 1-(4-methoxybenzyl)indole-2,3-dicarboxylic anhydride with (3-bromo-4-pyridyl)triisopropoxytitanium," *Journal of the Chemical Society*, Perkin Transactions 1 (2001), (18), 2213-2216.

Mishra et al., "Decanuclear Copper Framework Supported by a Tripodal Adenine Ligand," *Inorganic Chemistry* (Washington, DC, United States), (2010), 49(8), 3691-3693.

Mizoguchi, et al., "Genetic Alterations of Phosphoinositide 3-kinase Subunit Genes in Human Glioblastomas," Brain Pathol. 2004, 14(4):372-7.

Moffett, "Antiulcer agents. p-Aminobenzamido aromatic compounds", Journal of Medicinial Chemistry (1971), 14(10), 963-8.

Mohammadizadeh, et al., "A Novel and expedient synthesis of 7-pyrimidinylpyrimido[4,5-d]pyrimidinones,"*Helvetica Chimica Acta* (2010), 93(1), 153-157.

Morrison, et al., "Pyrimido[4,5-c]pyridazines. 1. Cyclizations with α-keto esters", *Journal of Organic Chemistry* (1978), 43(25), 4844-9.

Mukhopadhyay, et al., "An ionic liquid {[secbmim]+Br-} as a "dual reagent catalyst" for the multicomponent synthesis of (quinolinyl- and isoquinolinyl-amino) alkylnaphthols, their bis-analogs and a facile route to naphthoxazines," ARKIVOC (Gainesville, FL, United States) (2010), (10), 291-304.

Musmuca, et al., "Small-Molecule Interferon Inducers. Toward the Comprehension of the Molecular Determinants through Ligand-Based Approaches", Journal of Chemical Information and Modeling (2009),49(7),1777-1786.

Najiwara, et al., "Behavior of naphthoyloxyl and methoxynaphthoyloxyl radicals generated from the photocleavage of dinaphthoyl peroxides and 1-(napthoyloxy)-2-pyridones," *Bulletin of the Chemical Society of Japan* (2003), 76(3), 575-585.

Najiwara, et al., Generation and behavior of naphthoyloxyl radicals in photocleavage of 1-(naphthoyloxy)-2-pyridones, *Chemistry Letters* (2001), (10), 1064-1065.

Nettekoven, M., "A combinatorial approach towards 2-acyl-3-amino-indole derivatives," *Tetrahedron Letters* (2000), 41(43), 8251-8254.

Norman, P., "Selective PI3Kδ inhibitors, a review of the patent literature", Expert Opinion on Therapeutic Patents, Informa Healthcare, 21(11):1773-1790, 2011.

Oki, et al., "Reactivities of Stable Rotamers. XLII. Generation and Fates of Rotameric [1-(9-Fluorenyl)-2-naphtyl]methyl Radicals," *Bulletin of the Chemical Society of Japan* (1999), 72(10), 2327-2336.

Okkenhaug, et al., "Impaired B and T Cell Antigen Receptor Signaling in p110δ PI 3-Kinase Mutant Mice," Science, 2002, 297(5583):1031-4).

Park et al., Analytical Biochemistry 1999, 269, 94-104.

(56) References Cited

OTHER PUBLICATIONS

Park et al., "Phosphoinositide 3-kinase δ inhibitor as a novel therapeutic agent in asthma," Respirology, 13:764-771, 2008.
Phillips, et al., "The Reaction of anils with 8-quinolinol," *Journal of Organic Chemistry* (1954), 19, 907-9 CODEN: JOCEAH; ISSN: 0022-3263.
Pinedo and Slamon, "Translational Research: The Role of VEGF in Tumor Angiogenesis," The Oncologist, 5(1):1-2, 2000.
Platts, et al., "A concise synthesis of HIV integrase inhibitors bearing the dipyridone acid motif," *Tetrahedron Letters* (2011), 52(4), 512-514.
Portnaya, et al., "Azomethine dyes. IV. Indoaniline dyes derived from heterocyclic N-Substituted 1-hydroxy-2-naphthamides," *Ts. Vses. Nauchn.-Issled. Kinofotinst.* (1960), (No. 40), 106-18 (with English abstract).
Prezent, et al., STN Abstract, Accession No. 2004:358794, "Boron chelates as intermediates in the synthesis of new functionalized pyridines and pyramidines from α,α-dioxoketene aminals," *Boron Chemistry at the Beginning of the 21st Century*, [*Proceedings of the International Conference on the Chemistry of Boron*], 11th, Moscow, Russian Federation, Jul. 28-Aug. 1, 2002 (2003), Meeting Date 2002, 91-93. Editor(s): Bubnov, Yu. N. A. N. Nesmeyanov Institute of Organoelement Compounds, Russian Academy of Sciences: Moscow, Russia.
Puri and Gold, "Selective inhibitors of phosphoinositide 3-kinase delta: modulators of B-cell function with potential for treating autoimmune inflammatory diseases and B-cell malignancies," Frontiers in Immunology, 3(256):1-16, 2012.
Ramos-Casals et al., "Rituximab in systemic lupus erythematosus; A systematic review of off-label use in 188 cases," Lupus, 18:767-776, 2009.
Randis, et al., "Role of PI3Kδ PI3Kγ in inflammatory arthritis and tissue localization of neutrophils," Eur. J. Immunol., 2008, 38(5):1215-24.
Reich, et al., "Preparation of a,b-unsaturated carbonyl compounds and nitriles by selenoxied elemination," *Organic Reactions* (Hoboken, NJ, United States) (1993), 44, No pp. given.
Remington's Pharmaceutical Sciences, 17th ed., Mack Publishing Company, Easton, Pa., 1985, p. 1418.
Ringshausen et al., "Constitutively Actived phosphatidylinositol-3-kinase (PI-3K) is involved in the defect of apoptosis is B-CLL: assocaite with protein kinase C delta," Blood, 2002, 100:3741-3748.
Roxas-Duncan, et al., "Identification and biochemical charaterization of small-molecule inhibitors of Clostridium botulinum neurotoxin serotype A," *Antimicrobial Agents and Chemotherapy* (2009), 53(8), 3478-3486.
Sahoo, et al., "Antispasmodic compounds. IV," Journal of the Indian Chemical Society (1959), 36, 421-4.
Sako, M., "Product class 19: pyridopyrimidines," *Science of Synthesis* (2004), 16, 1155-1267.
Samuels and Ericson, "Concogenic PI3K and its role in cancer," Curr Opin Oncol., 2006, 18(1):77-82.
Samuels, et al., "High Frequency of Mutations of the PIK3CA Gene in Human Cancers," Science, 2004, 304(5670):554.
Sasaki, et al., "Function of PI3Kγ in Thymocyte Development, T Cell Activation, and Neutrophil Migration," Science, 2000, 287(5455):1040-6.
Sawyers, "The cancer biomarker problem," Nature, 2008, 542:548-552.
Saxena, et al., "Pharmacophore-based virtual screening and docking studies on Hsp90 inhibitors", SAR and QSAR in Environmental Research (2010), 21(5-6), 445-462.
Schafer and Kolkhof, "Failure is an option: learning from unsuccessful proof-of-concept trials," Drug Discovery Today, Nov. 2008, 13(21/22):913-916.
Schell, et al., "Versatile Solid-Phase Synthesis of Trissubstituted 1H-Pyrido[2,3-d]pyrimidin-4-ones and Rekated Heterocycles," *Journal of Combinatorial Chemistry* (2005), 7(1), 96-98.

Selig et al., "The applicaiton of Stille cross-coupling reactions with multiple nitrogen containing heterocycles," Tetrahedron, Sep. 2011, 67(47): 9204-9213.
Segarra et al., "Successful treatment of membranous glomerulonephritis with rituximab in calcineurin inhibitor-dependent patients," Clin J Am Soc Nephrol., 2009, 4(6):1083-8.
Sen, et al., "Reaction of aldehydes and amines with 8-hydroxyquinaldine and 8-quinolinol. II," *Journal of the Indian Chemical Society* (1960), 37, 640-2.
Shi, et al., "Synthesis and preliminary cytotoxic evaluation of substituted indoles as potential anticancer agents," *Chinese Chemical Letters* (2007), 18(8), 899-901, CODEN:CCLEE7; ISSN: 1001-8417.
Shuttleworth et al., "Progress in the Preclinical Discovery and Clinical Development of Class 1 and Dual Class I/IV Phosphoinositide 3-Kinase (PI3K) Inhibitors", Current Meicinal Chemistry, 18(1):2686-2714, 2011.
Silverman, R. B., "The organic Chemistry of Drugs Design and Drug Action." Elsevier. Northwestern University. Second Edition. Evanstons Illinois. 2004. pp. 29 and table 2.2 *Too Voluminous to Provide.
Singh et al., "Application of Nazarov cyclization to access [6-5-6] and [6-5-5]tricyclic core embedded new heterocycles: an easy entry to structures related to Taiwaniaquinoids," *Organic & Biomolecular Chemistry* (2009), 7(9), 1858-1867, CODEN: OBCRAK; ISSN: 1477-0520.
Steliou, et al., "Does diatomic sulfur(S2) react as a free species?", *Journal of the American Chemical Society* (1992), 1456-62.
Stüve et al., "Long-term B-lymphocyte Depletion with Rituximab in Patients With Relapsing-Remitting Multiple Sclerosis," Arch. Neurol., 66(2):259-261, 2009.
Sujobert, et al., "Essential role for the p110δ isofrom in phosphoinositide 3-kinase activation and cell proliferation in acute myeloid leukemia," Blood, 2005, 106(3):1063-6.
Szuecova, et al., "Synthesis, characterization and biological activity of ring-substituted 6-benzylamino-9-tetrahydropyran-2-yl and 9-tetrahydrofuran-2-ylpurine derivatives," *Bioorganic & Medicinal Chemistry* (2009), 17(5), 1938-1947.
Terrier, et al., "Tolerance and efficacy of Rituximab (RTX) in Systemic Lupus Erythematosus (SLE): data of 104 Patients From the AIR (Auto-immunity and Rituximab) Registry," Presented at 73th Annual Scientific Meeting of the American College of Rheumatology, Oct. 2009; Philadelphia, PA.
Thomas, et al., "Airway inflammation: chemokine-induced neutrophilia and the class I phosphoinositide 3-kinases," Eur J Immunol. 2005, 35(4):1283-91.
Travnickek, et al., "2-Chloro-6-[(4-hydroxy-3,5-dimethoxybenzyl)amino]-9-isopropylpurine," *Acta Crystallographica*, Section E: Structure Reports Online (2007), E63(2), o728-o730 CODEN: ACSEBH; ISSN: 1600-5368 URL: http://journals.iucr.org/e/issues/2007/02/00/lh2285/lh2285
Umar, A., "Future directions in cancer prevention," Nature Reviews Cancer, 12.12 (2012): 835-848.
Uddin et al., "Role of phosphatidylinositol 3'-kinase/AKT pathway in diffues large B-cell lymphomas survival," Blood, 2006, 108:4178-4186.
Vanhaesebroeck et al., "Signalling by PI3K isoforms: insights from gene-targeted mice," Trends Bichem Sci., 2005, 30(4):194-204.
Vail'ev, et al, "Chelate synthesis of 1-alkyl-5-trifluoromethyl)-1,6-napthyridin-4(1H)-ones", Izvestiya Akademii Nauk, Seriya Khimicheskaya (1994),(8), 1510-11 (with English abstract).
Venet et al., "Lymphocytes in the Development of Lung Inflammation: A role of Regulatory CD4+ T Cells in Indirect Pulmonary Lung Injury," J Immunol., 183:6472-3480.
Wallin, J.J., "GDC-0980 is a novel class I PI3K/mTOR kinase inhibitor with robust activity in cancer models driven by the PI3K pathway," Molecular cancer therapeutics 10.12 (2011): 2426-2436.
Walsh and Jayne, "Rituximab in the treatment of anti-neutrophil cytoplasm antibody associated vasculitis and systemic lupus erthematosis: past, present and future," Kidney International, 2007, 72: 676-682.
WebMD. Arthritis Health Center: What is Inflammation? Jul. 6, 2012, www.webmd.com/arthritis/about-inflammation?page=2, 4 pages.

(56) References Cited

OTHER PUBLICATIONS

WebMD. Bladder Cancer Health Center: Bladder Cancer—Prevention, Apr. 30, 2013, www.webmd.com/cancer/bladder-cancer/bladder-cancer-prevention, 1 pages.
WebMD. Lung Disease & Respiratory Health Center: ARDS, May 21, 2014, www.webmd.com/lung/ards-acute-respiratory-dostress-syndrome?page=2, 4 pages.
WebMD. Lung Disease & Respiratory Health Center: Lung Disease Overview, May 23, 2014, www.webmd.com/lung/lung-diseases-overview, 3 pages.
WebMD. Osteoarthritis Health Center: Osteoarthritis—prevention, Apr. 9, 2013, www.webmd.com/osteoarthritis/tc/osteoarthritis-prevention, 2 pages.
WebMD. Psoriasis Health Center: Psoriasis—prevention, Jan. 9, 2012, www.webmd.com/skin-problems-and-treatments/psoriasis/psoriasis-prevention, 1 page.
Xu et al., "Activation of the PI3K/AKT/mTOR pathway in diffues large B cell lymphoma: clinical significance and inhibitory effect of rituximab," Ann Hematol., 2013, 92:1351-1358.
Yaguchi et al., "Antitumor Activity of ZSTK474, a new Phosphatidylinositol 3-Kinase Inhibitor," *J Natl. Cancer Inst.*, 2006, 98(8):545-556.
Yahay-Zadeh, "Synthesis of 9-Aryl-6-aminopurines from 5-Amino-1-aryl-1H-imidazole-4-carbonitriles", Russian Journal of Organic Chemistry (translation of Zhurnal Oranicheskoi Khimii) (2003), 39(11),1649-1651.
Yahyazadeh, et al., "Synthesis of 9-benzyl-6-aminopurines from 5-amino-1-benzyl-4-cyanoimidazoles", Bulletin of the Korean Chemical Society (2003), 24(12), 1723-1724.
Yamada et al., "Alpha-1 Adrenoceptors in Human Prostate: Characterization and Alteration in Benign Prostatic Hypertrophy," J Pharmacol Experimental Therapeutics, 1987, 242(1):326-330.
Yanni, A. S., "Synthesis of some new 5-iodo-7-substituted-aminomethyl-8-hydroxyquinoline," *Revue Roumaine de Chimie* (1994), 39(7), 833-6 CODEN: RRCHAX; ISSN: 0035-5930.
Yanni, et al., "Synthesis and biological activity of some 7-substituted ammomethyl-8-hydroxyquinoline-5-sulfonic acids," *Indian Journal of Chemistry, Section B: Organic Chemistry Inculding Medicinal Chemistry* (1982), 21B(7), 705-6.
Yoo, et al., "Synthesis and Evaluation of Antitumor activity of novel 2-[N-methyl-N-(4-methyl-1,3-benzothiazol-2-yl)aminomethyl]-5,8-diacyloxy-1,4-napthoquinones," *Archives of Pharmacal Research* (2008), 31(2), 142-147 CODEN: APHRDQ; ISSN: 0253-6269.
Yoon et al., "Impact of fluoroquinolones on the diagnosis of pulmonary tuberculosis initially treated as bacterial pneumonia," Int'l J Tuberculosis and Lung Dis, 2005, 9:1215-1219.
Yoshida, et al., "MexAB-OprM specific efflux pump inhibiots in Pseudomonas aeruginosa. Part 5: Carbon-Substituted analogues at the C-2 postition," *Bioorganic & Medicinal Chemistry* (2006), 14(6), 1993-2004.
Yuan, T.L., "PI3K pathway alteration in cancer: variations on a theme," Oncogene, 2008, 27.41:5497-551.
Zhang et al., "Advances in preclinical small molecules for the treatment of NSCLC", Expert Opinion on Therapeutic Patent, 19(6)731-751, 2009.
Zhao and Vogt, "Class I PI3K in oncogenic cellular transformation," Oncogene, 2008, 27:5486-5496.
Zhao, et al., "Synthesis and in vitro anti-hepatitis B virus activities of some ethyl 5-hydroxy-1H-indole-3-carboxylates," *Bioorganic & Medicinal Chemistry* (2006), 14(8), 2552-2558.
International Preliminary Report on Patentability dated Dec. 28, 2012 for International Appln. No. PCT/US2011/041202 (8 pgs.).
International Preliminary Report on Patentability dated Jul. 4, 2013 for International Appln. No. PCT/US2011/065743 (8 pgs).
International Preliminary Report on Patentability dated Jun. 19, 2012 for International Appln. No. PCT/US2010/061023 (6 pgs.).
International Preliminary Report on Patentability dated Jun. 19, 2012 for International Appln. No. PCT/US2010/060980 (8 pgs.).
International Preliminary Report on Patentability dated Oct. 16, 2012 for International Appln. No. PCT/US2011/032213 (6 pgs.).
International Preliminary Report on Patentability for PCT/US2010/040150 dated Jul. 5, 2011 (24pgs.).
International Preliminary Report on Patenetability for PCT/US2012/030310 dated Oct. 1, 2013 (7pgs.).
International Preliminary Report on Patentability for PCT/US2012/028915 dated Sep. 17, 2013 (6pgs.).
International Preliminary Report on Patentability for PCT/US2012/053398, dated Mar. 4, 2014 (6 pgs.).
International Search Report dated Jul. 11, 2013 for International Appln. No. PCT/US2013/034803 (15 pgs.).
International Search Report dated Dec. 21, 2012 for International Appln. No. PCT/US2012/053398 (11 pgs.).
International Seaerch Report dated Feb. 28, 2012 for International Appln. No. PCT/US2011/065743 (13 pgs.).
International Search Report dated May 11, 2012 for International Appln. No. PCT/US2012/030310 (11 pgs.).
International Search Report dated May 31, 2012 for International Appln. No. PCT/US2012/028915 (11 pgs.).
International Search Report dated Sep. 23, 2011 for International Appln. No. PCT/US2011/041202 (12 pgs.).
International Search Report for PCT/US2010/040150 dated Nov. 8, 2010 (19 pgs.).
International Search Report for PCT/US2010/060980 dated Mar, 15, 2011 (12 pgs.)
International Search Report for PCT/US2010/061023 dated Feb. 16, 2011 (10 pgs.).
International Search Report for PCT/US2011/032213 dated Jun. 14, 2011 (11 pgs.).
STN Search Report, conducted Dec. 1, 2010, 132 pages.
STN Search Report, conducted Dec. 16, 2009, 72 pages.
STN Search Report, conducted prior to Jun. 21, 2011, 224 pages.
STN Search Report, conducted Apr. 5, 2010, 513 pages.
STN Search Report, conducted Apr. 24, 2009, 43 pages.
STN Search Report, conducted Dec. 7, 2010, 213 pages.
STN Search Report, dated Aug. 29, 2011, 181 pages.
STN Search Report, dated May 27, 2009, 2 pages.
STN Search Report, dated May 28, 2009, 81 pages.
STN Search Report, dated Apr. 2, 2010, 141 pages.
STN Search Report, dated Aug. 30, 2011, 61 pages.
Office Action in CO Application No. 11-179.464, dated Mar. 14, 2014, 17 pages.
Office Action in JP Application No. 2012-518563, dated Jul. 8, 2014, 6 pages (with English translation).
Office Action in JP Application No. 2013-546274, dated Sep. 15, 2015, 7 pages (with English Translation).
Office Action in JP Application No. 2014-223540, dated Jul. 21, 2015, 5 pages (with English Translation).
International Search Report and Written Opinion in International Application No. PCT/US2016/031606, dated Jun. 20, 2016, 10 pages.
International Search Report and Written Opinion in International Application No. PCT/US2016/031611, dated Jun. 20, 2016, 10 pages.
International Search Report and Written Opinion in International Application No. PCT/US2016/031603, dated Jun. 22, 2016, 11 pages.
International Search Report and Written Opinion in International Application No. PCT/US2015/035046, dated Aug. 27, 2015, 9 pages.
International Search Report and Written Opinion in International Application No. PCT/US2016/019741, dated Aug. 2, 2016, 16 pages.
International Preliminary Report on Patentability in International Application No. PCT/US2015/035046, dated Dec. 22, 2016, 7 pages.
Malaysian Office Action in Malaysian Application No. PI 2011006255, dated Mar. 15, 2017, 2 pages.
European Search Report in European Application No. 16199883.6, dated Jun. 4, 2017, 7 pages.
Vietnamese Office Action in Vietnamese Application No. 2012-00241, dated May 9, 2017, 3 pages (English Translation).

(56) References Cited

OTHER PUBLICATIONS

International Preliminary Report on Patentability in International Application No. PCT/US2016/019741, dated Aug. 29, 2017, 10 pages.
Vietnamese Office Action in Vietnamese Application No. 2017-03601, dated Nov. 27, 2017, 2 pages (English Translation).
International Preliminary Report on Patentability in International Application No. PCT/US2016/031606, dated Nov. 23, 2017, 7 pages.
International Preliminary Report on Patentability in International Application No. PCT/US2016/031611, dated Nov. 23, 2017, 7 pages.
International Preliminary Report on Patentability in International Application No. PCT/US2016/031603, dated Nov. 23, 2017, 7 pages.
Australian Office Action in Australian Application No. 2017206260, dated Mar. 20, 2018, 4 pages.
Peru Office Action in Peru Application No. 287.14, dated Dec. 14, 2017, 16 pages (English Translation).
Taiwan Office Action in Taiwan Application No. 105111882, dated Mar. 8, 2017, 6 pages (English Translation).

XRPD Form I

DSC Form I

TGA Form I

DVS Form I

Cycle 1

Cycle 2

TGA Form II

DSC of Form III
Cycle 1

Cycle 2

TGA of Form III

DSC of Form IV
Cycle 1

Cycle 2

TGA of Form IV

DSC of Form V
Cycle 1

Cycle 2

TGA of Form V

DSC Form VI
Cycle 1

Cycle 2

TGA Form VI

TGA of Form VII

DSC of Form VII
Cycle 1

Cycle 2

DSC of Form VIII

Cycle 1

Cycle 2

TGA of Form VIII

DSC of Form IX

TGA of Form IX

DSC of Form X

TGA of Form X

XRPD for Form XI

DSC of Form XI
Cycle 1

Cycle 2

XRPD for Form XII

DSC for Form XII

XRPD of Form XIII

DSC of Form XIII

CRYSTALLINE FORMS OF A PI3K INHIBITOR

FIELD OF THE INVENTION

The present invention is related to crystalline forms of (S)-7-(1-(9H-purin-6-ylamino)ethyl)-6-(3-fluorophenyl)-3-methyl-5H-thiazolo[3,2-a]pyrimidin-5-one which is a PI3K inhibitor useful in the treatment of cancer and other diseases.

BACKGROUND OF THE INVENTION

The compound (S)-7-(1-(9H-purin-6-ylamino)ethyl)-6-(3-fluorophenyl)-3-methyl-5H-thiazolo[3,2-a]pyrimidin-5-one having Formula I:

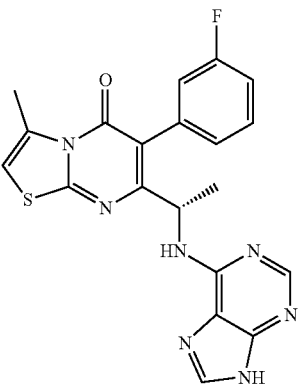

I is a phosphoinositide 3-kinase (PI3K) inhibitor useful in the treatment of various diseases including cancer. The compound of Formula I, as well as its preparation and use, have been described in US Pat. App. Pub. No. 2011/0015212, which is incorporated herein by reference in its entirety. For the development of a drug, it is typically advantageous to employ a form of the drug having desirable properties with respect to its preparation, purification, reproducibility, stability, bioavailability, and other characteristics. Accordingly, the crystalline forms of the compound of Formula I provided herein help satisfy the ongoing need for the development of PI3K inhibitors for the treatment of serious diseases.

SUMMARY OF THE INVENTION

The present invention provides a crystalline form of the compound of Formula I:

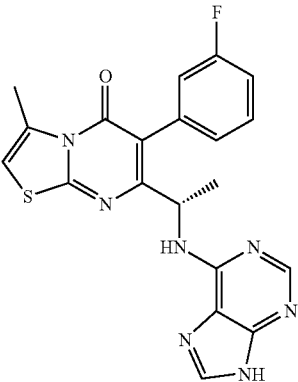

I which is any one of Forms I, II, III, IV, V, VI, VII, VIII, IX, X, XI, XII, and XIII described herein.

The present invention further provides a crystalline form of the compound of Formula I which is hydrated.

The present invention further provides a crystalline form of the compound of Formula I which is a hemihydrate.

The present invention further provides a composition comprising a crystalline form of the invention and at least one pharmaceutically acceptable carrier.

The present invention further provides a process for preparing a crystalline form of the invention.

The present invention further provides a method of treating a disease associated with abnormal expression or activity of a PI3K kinase in a patient, comprising administering to the patient a therapeutically effective amount of a crystalline form of the invention.

DETAILED DESCRIPTION

Figure 1:
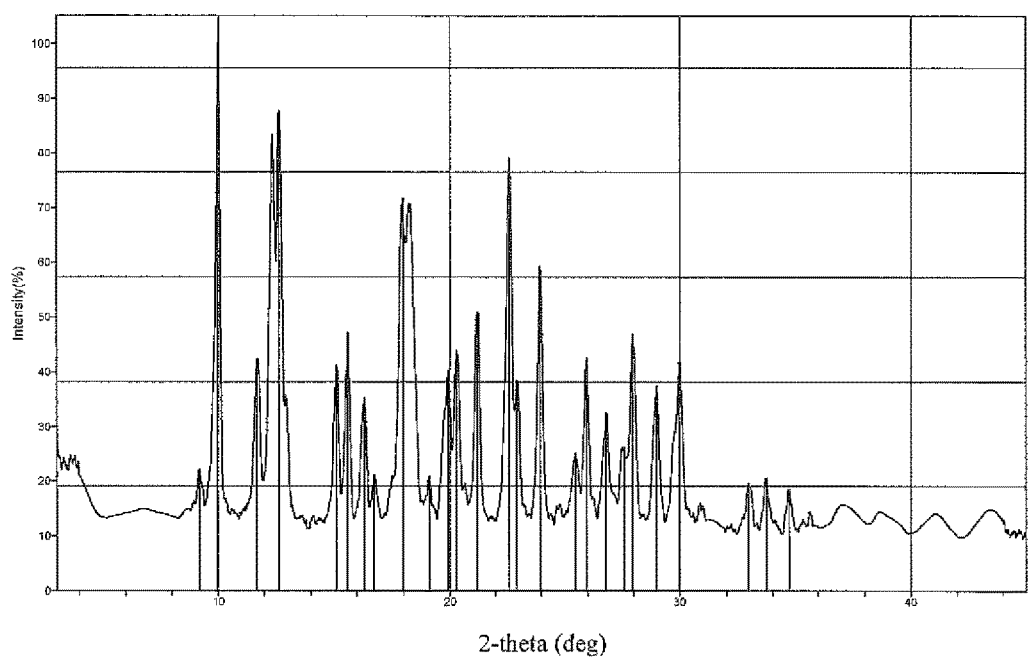
FIG. 1 shows an XRPD pattern for Form I.

The present invention relates to, inter alia, crystalline forms of the PI3K inhibitor (S)-7-(1-(9H-purin-6-ylamino)ethyl)-6-(3-fluorophenyl)-3-methyl-5H-thiazolo[3,2-a]pyrimidin-5-one having Formula I:

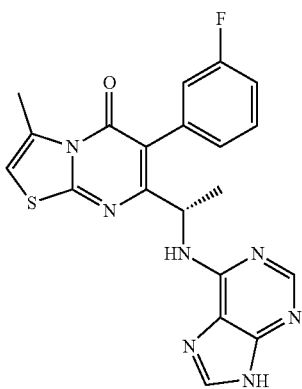

which are useful, for example, in the preparation of solid dosage forms of the above compound for the treatment of various diseases, including cancer.

Typically, different crystalline forms of the same substance have different bulk properties relating to, for example, hygroscopicity, solubility, stability, and the like. Forms with high melting points often have good thermodynamic stability which is advantageous in prolonging shelf-life drug formulations containing the solid form. Forms with lower melting points often are less thermodynamically stable, but are advantageous in that they have increased water solubility, translating to increased drug bioavailability. Forms that are weakly hygroscopic are desirable for their stability to heat and humidity and are resistant to degradation during long storage. Anhydrous forms are often desirable because they can be consistently made without concern for variation in weight or composition due to varying solvent or water content. On the other hand, hydrated or solvated forms can be advantageous in that they are less likely to be hygroscopic and may show improved stability to humidity under storage conditions.

As used herein, "crystalline form" is meant to refer to a certain lattice configuration of a crystalline substance. Different crystalline forms of the same substance typically have different crystalline lattices (e.g., unit cells) which are attributed to different physical properties that are characteristic of each of the crystalline forms. In some instances, different lattice configurations have different water or solvent content. The different crystalline lattices can be identified by solid state characterization methods such as by X-ray powder diffraction (XRPD). Other characterization methods such as differential scanning calorimetry (DSC), thermogravimetric analysis (TGA), dynamic vapor sorption (DVS), solid state NMR, and the like further help identify the crystalline form as well as help determine stability and solvent/water content.

Crystalline forms of a substance include both solvated (e.g., hydrated) and non-solvated (e.g., anhydrous) forms. A hydrated form is a crystalline form that includes water in the crystalline lattice. Hydrated forms can be stoichiometric hydrates, where the water is present in the lattice in a certain water/molecule ratio such as for hemihydrates, monohydrates, dihydrates, etc. Hydrated forms can also be non-stoichiometric, where the water content is variable and dependent on external conditions such as humidity.

Crystalline forms are most commonly characterized by XRPD. An XRPD pattern of reflections (peaks) is typically considered a fingerprint of a particular crystalline form. It is well known that the relative intensities of the XRPD peaks can widely vary depending on, inter alia, the sample preparation technique, crystal size distribution, filters, the sample mounting procedure, and the particular instrument employed. In some instances, new peaks may be observed or existing peaks may disappear, depending on the type of instrument or the settings (for example, whether a Ni filter is used or not). As used herein, the term "peak" refers to a reflection having a relative height/intensity of at least about 4% of the maximum peak height/intensity. Moreover, instrument variation and other factors can affect the 2-theta values. Thus, peak assignments, such as those reported herein, can vary by plus or minus about 0.2° (2-theta), and the term "substantially" as used in the context of XRPD herein is meant to encompass the above-mentioned variations.

In the same way, temperature readings in connection with DSC, TGA, or other thermal experiments can vary about ±4° C. depending on the instrument, particular settings, sample preparation, etc. For example, with DSC it is known that the temperatures observed will depend on the rate of the temperature change as well as the sample preparation technique and the particular instrument employed. Thus, the values reported herein related to DSC thermograms can vary, as indicated above, by ±4° C. Accordingly, a crystalline form reported herein having a DSC thermogram "substantially" as shown in any of the Figures is understood to accommodate such variation.

The compound of Formula I can be isolated in numerous crystalline forms, including crystalline forms which are anhydrous, hydrated, non-solvated, or solvated. Example hydrates include hemihydrates, monohydrates, dihydrates, and the like. In some embodiments, the crystalline forms of the compound of Formula I are anhydrous and non-solvated. By "anhydrous" is meant that the crystalline form of the compound of Formula I contains essentially no bound water in the crystal lattice structure, i.e., the compound does not form a crystalline hydrate.

In some embodiments, the crystalline forms of the invention are substantially isolated. By "substantially isolated" is meant that a particular crystalline form of the compound of Formula I is at least partially isolated from impurities. For example, in some embodiments a crystalline form of the invention comprises less than about 50%, less than about 40%, less than about 30%, less than about 20%, less than about 15%, less than about 10%, less than about 5%, less than about 2.5%, less than about 1%, or less than about 0.5% of impurities. Impurities generally include anything that is not the substantially isolated crystalline form including, for example, other crystalline forms and other substances.

In some embodiments, a crystalline form of the compound of Formula I is substantially free of other crystalline forms. The phrase "substantially free of other crystalline forms" means that a particular crystalline form of the compound of Formula I comprises greater than about 80%, greater than about 90%, greater than about 95%, greater than about 98%, greater than about 99% or greater than about 99.5% by weight of the particular crystalline form.

Crystalline Form I

In some embodiments, the crystalline form of the compound of Formula I is Form I. This crystalline form can be generally prepared as described in Example 1.

Crystalline Form I can be identified by unique signatures with respect to, for example, X-ray powder diffraction (XRPD), differential scanning calorimetry (DSC), thermogravimetric analysis (TGA), and dynamic vapor sorption (DVS). In some embodiments, crystalline Form I is characterized by an XRPD pattern substantially as shown in FIG. 1. Peaks from the XRPD pattern are listed in Table 1.

In some embodiments, crystalline Form I is characterized by an XRPD pattern comprising a peak, in terms of 2θ, at 10.0°±0.2°. In some embodiments, crystalline Form I has an XRPD pattern comprising the following peaks, in terms of 2θ: 10.0°±0.2°; 12.6°±0.2°; 15.6°±0.2°; and 18.0°±0.2°. In some embodiments, crystalline Form I has an XRPD pattern comprising 2 or more, 3 or more, or 4 or more of the following peaks, in terms of 2θ: 10.0°±0.2°; 11.7°±0.2°; 12.6°±0.2°; 15.1°±0.2°; 15.6°±0.2°; 18.0°±0.2°; 21.2°±0.2°; 22.6°±0.2°; 24.0°±0.2°; and 28.0°±0.2°.

Figure 2:
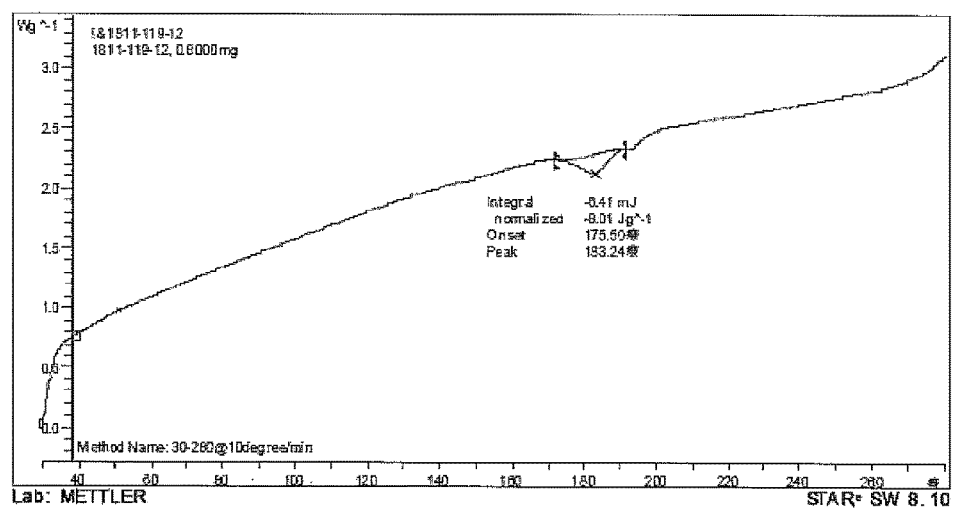
FIG. 2 shows the results of a DSC experiment for Form I.

In some embodiments, Form I is characterized by a DSC thermogram comprising an endothermic peak having a maximum at about 183° C. In some embodiments, crystalline Form I has a DSC thermogram substantially as shown in FIG. 2.

Figure 3:
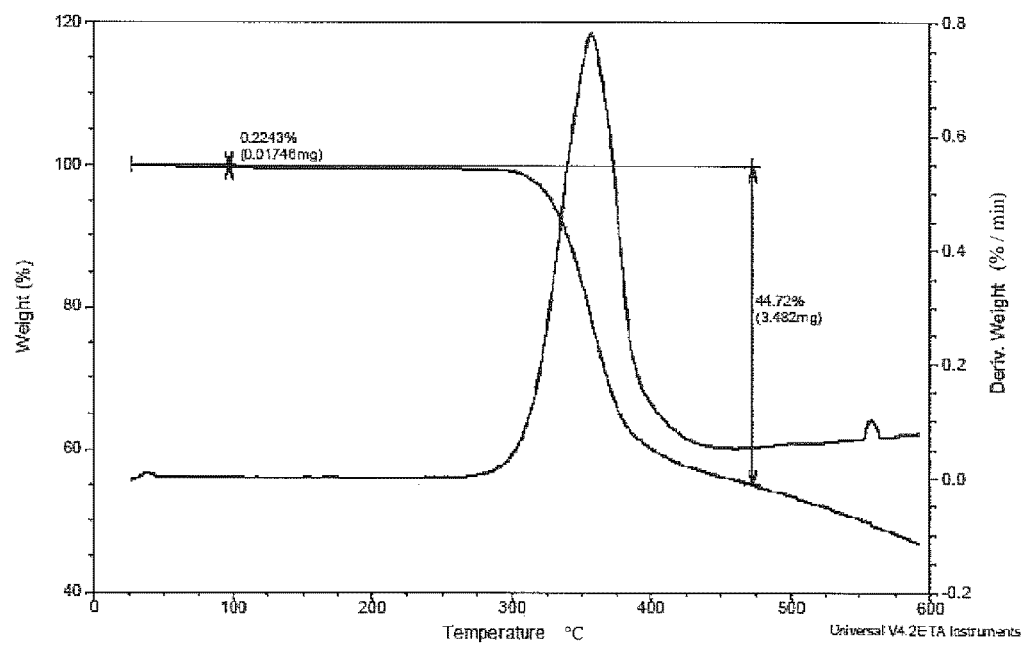
FIG. 3 shows the results of a TGA experiment for Form I.

In some embodiments, crystalline Form I has a TGA trace substantially as shown in FIG. 3.

Figure 4:
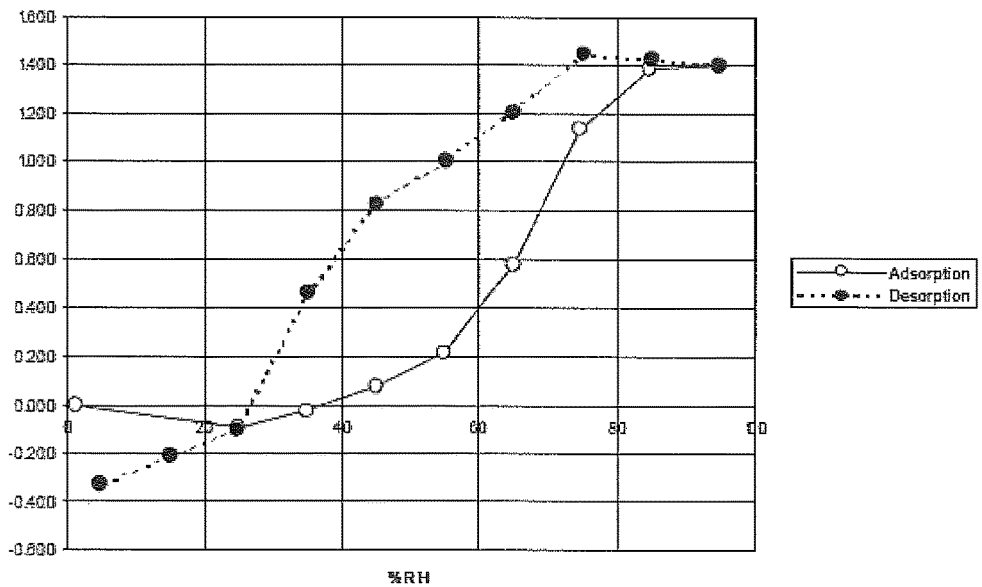
FIG. 4 shows the results of a DVS experiment for Form I; first cycle is shown in the upper panel and second cycle is shown in the lower panel.
Figure 4:
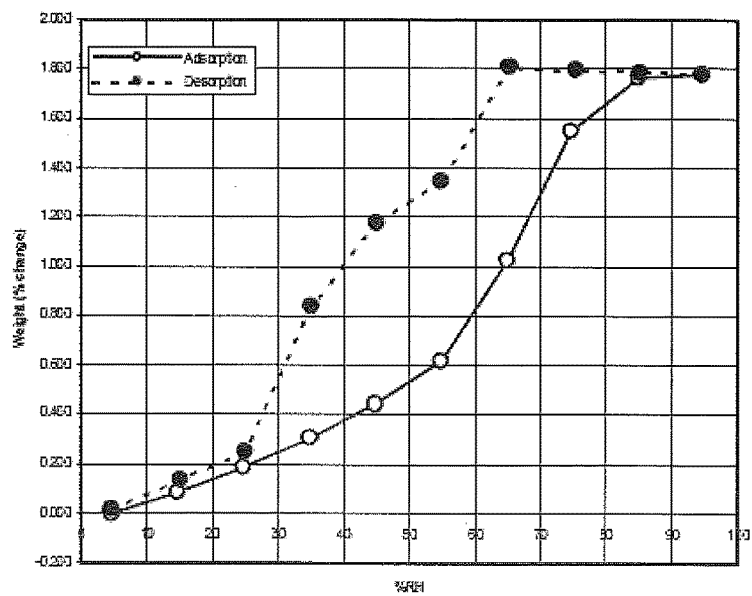

In some embodiments, crystalline Form I has a DVS trace substantially as shown in FIG. 4.

Crystalline Form II

In some embodiments, the crystalline form of the compound of Formula I is Form II. Crystalline Form II can be prepared by combining Form I with an alcohol such as isopropyl alcohol and optionally heating the resulting mixture.

Figure 5:
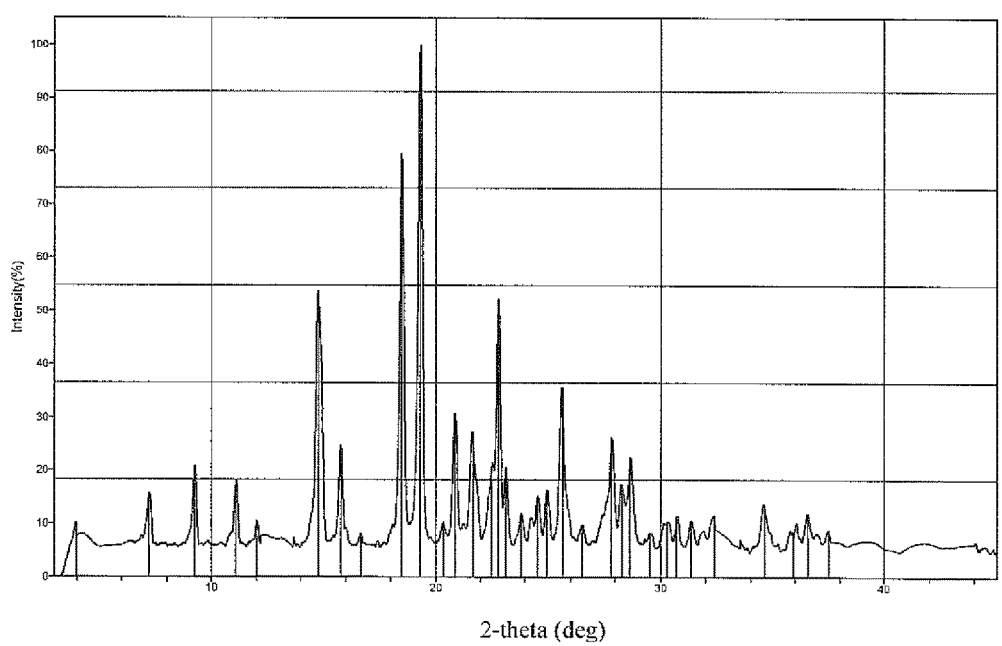
FIG. 5 shows an XRPD pattern for Form II.

Crystalline Form II can be identified by unique signatures with respect to, for example, XRPD, DSC, and TGA. In some embodiments, crystalline Form II is characterized by an XRPD pattern substantially as shown in FIG. 5. Peaks from the XRPD pattern are listed in Table 11.

In some embodiments, crystalline Form II is characterized by an XRPD pattern comprising a peak, in terms of 2θ, at 9.2°±0.2°. In some embodiments, crystalline Form II has an XRPD pattern comprising the following peaks, in terms of 2θ: 14.8°±0.2°; 18.5°±0.2°; 19.3°±0.2°; and 22.8°±0.2°. In some embodiments, crystalline Form II has an XRPD pattern comprising 2 or more, 3 or more, or 4 or more of the following peaks, in terms of 2θ: 9.2°±0.2°; 11.1°±0.2°; 14.8°±0.2°; 15.8°±0.2°; 19.3°±0.2°; 20.8°±0.2°; 21.7°±0.2°; 22.8°±0.2°; and 25.6°±0.2°.

Figure 6:
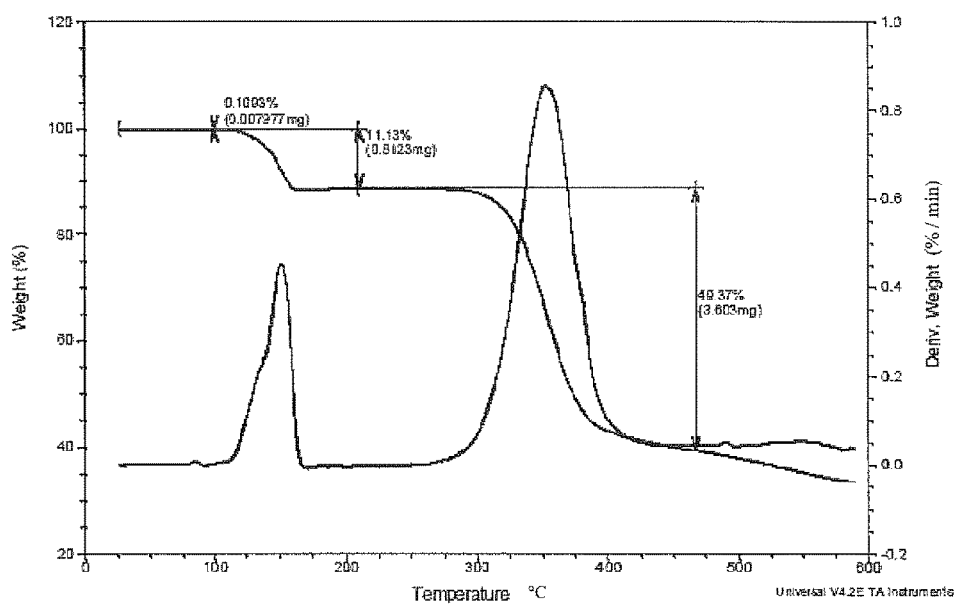
FIG. 6 shows the results of a TGA experiment for Form II.

In some embodiments, crystalline Form II of the compound of Formula I has a TGA trace substantially as shown in FIG. 6.

Crystalline Form III

In some embodiments, the crystalline form of the compound of Formula I is Form III. Crystalline Form III can be prepared by combining Form I with isopropyl acetate. The resulting mixture can be optionally heated.

Figure 7:
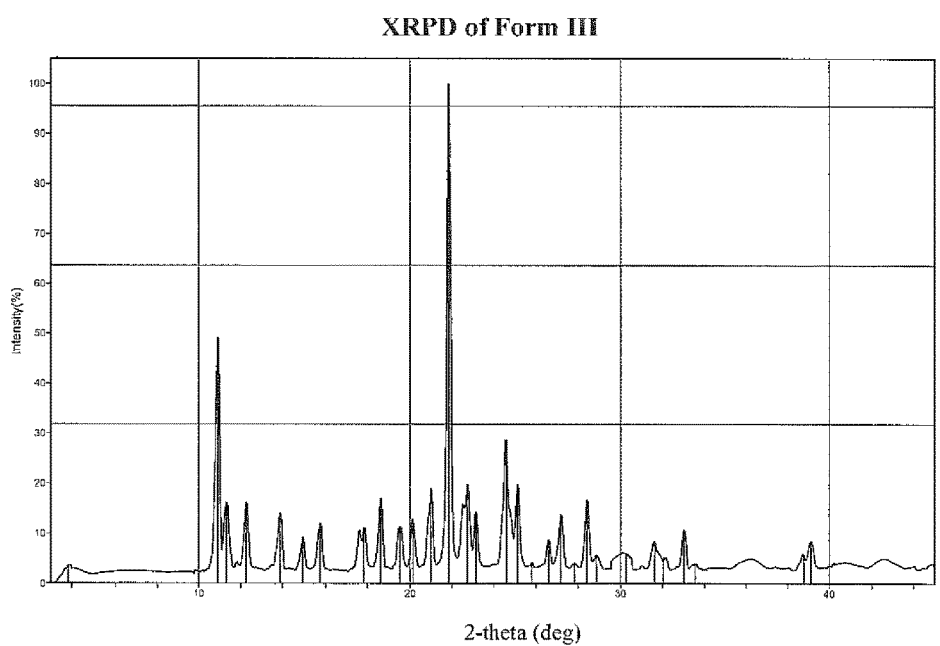
FIG. 7 shows an XRPD pattern for Form III.

Crystalline Form III can be identified by unique signatures with respect to, for example, XRPD, DSC, and TGA. For example, crystalline Form III is characterized by an XRPD pattern substantially as shown in FIG. 7. Peaks from the XRPD pattern are listed in Table 12.

In some embodiments, crystalline Form III is characterized by an XRPD pattern comprising a peak, in terms of 2θ, at 10.9°±0.2°. In some embodiments, crystalline Form III has an XRPD pattern comprising the following peaks, in terms of 2θ: 10.9°±0.2°; and 21.8°±0.2°. In some embodiments, crystalline Form III has an XRPD pattern comprising 2 or more, 3 or more, or 4 or more of the following peaks, in terms of 2θ: 10.9°±0.2°; 11.3°±0.2°; 12.3°±0.2°; 13.9°±0.2°; 18.6°±0.2°; 21.0°±0.2°; 21.8°±0.2°; 24.6°±0.2°; and 28.4°±0.2°.

Figure 8:
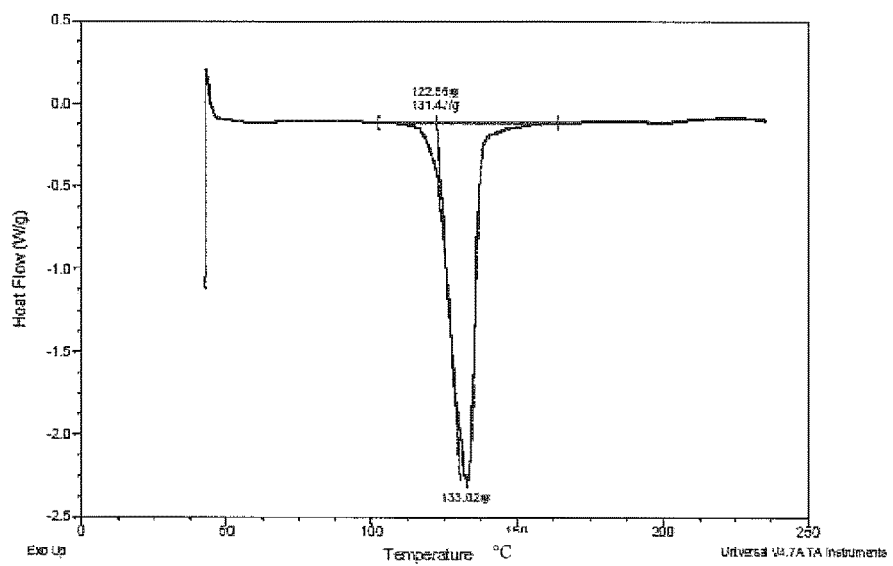
FIG. 8 shows the results of a DSC experiment for Form III; first cycle is shown in the upper panel and second cycle is shown in the lower panel.
Figure 8:
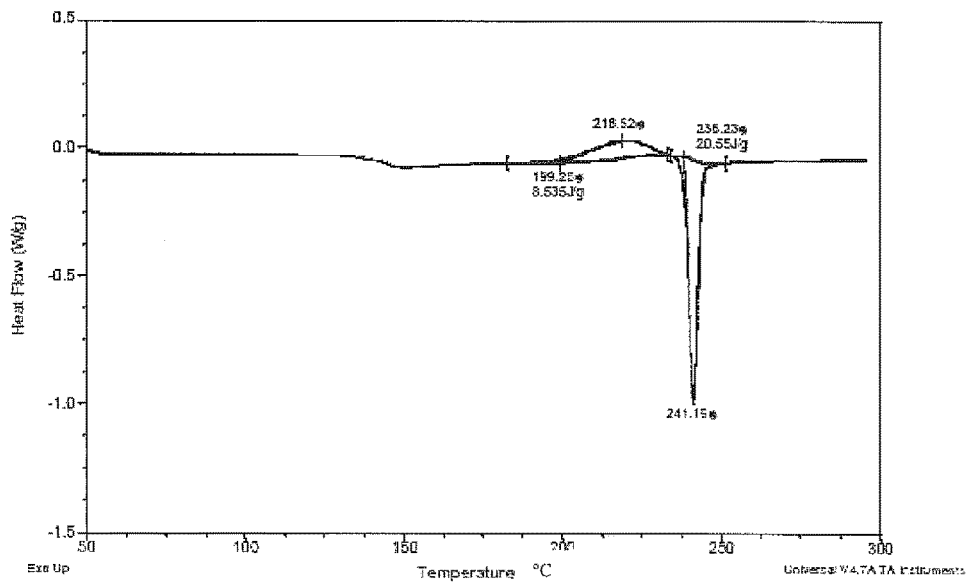

In some embodiments, Form III is characterized by a DSC thermogram comprising an endothermic peak having a maximum at about 133° C. In some embodiments, crystalline Form III has a DSC thermogram substantially as shown in FIG. 8 (upper).

Figure 9:
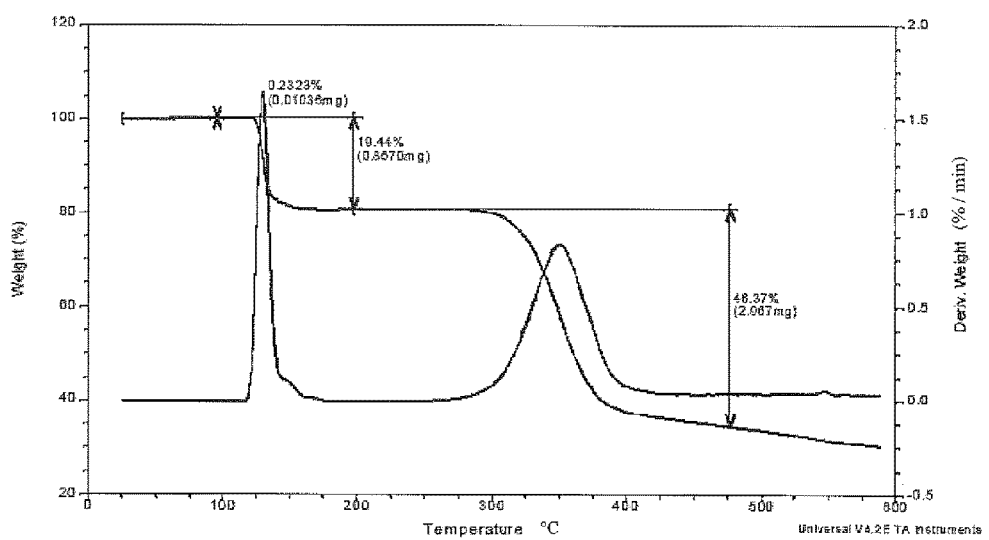
FIG. 9 shows the results of a TGA experiment for Form III.

In some embodiments, crystalline Form III has a TGA trace substantially as shown in FIG. 9.

Crystalline Form IV

In some embodiments, the crystalline form of the compound of Formula I is Form IV. Crystalline Form IV can be prepared by combining Form I with toluene. The resulting mixture can be optionally heated.

Figure 10:
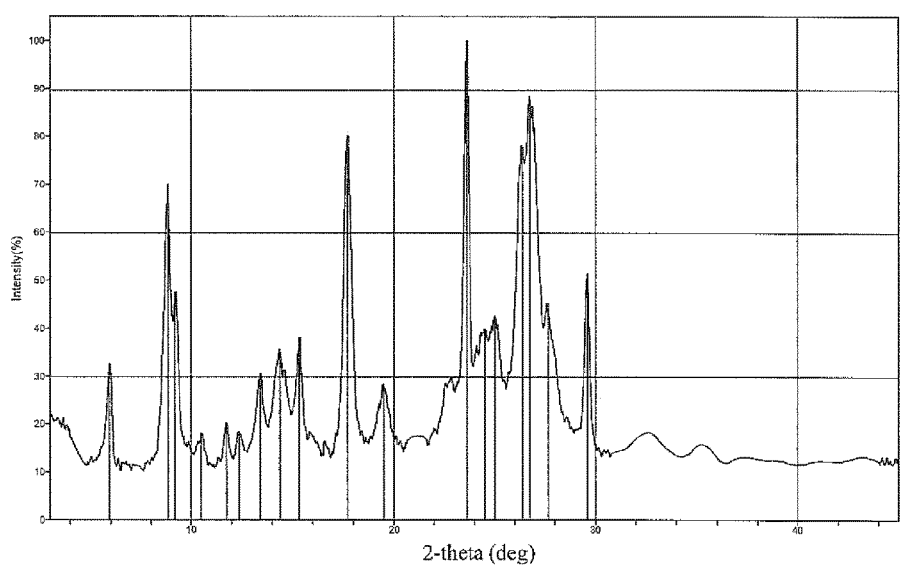
FIG. 10 shows an XRPD pattern for Form IV.

Crystalline Form IV of the compound of Formula I can be identified by unique signatures with respect to, for example, XRPD, DSC, and TGA. In some embodiments, crystalline Form IV is characterized by an XRPD pattern substantially as shown in FIG. 10.

In some embodiments, crystalline Form IV is characterized by an XRPD pattern comprising a peak, in terms of 2θ, at 8.8°±0.2°. In some embodiments, crystalline Form IV of the compound of Formula I has an XRPD pattern comprising the following peaks, in terms of 2θ: 5.9°±0.2°; 8.8°±0.2°; 17.7°±0.2°; and 23.6°±0.2°. In some embodiments, crystalline Form IV of the compound of Formula I has an XRPD pattern comprising 2 or more, 3 or more, or 4 or more of the following peaks, in terms of 2θ: 5.9°±0.2°; 8.8°±0.2°; 9.1°±0.2°; 17.7°±0.2°; 23.6°±0.2°; 26.4°±0.2°; 26.8°±0.2°; and 29.6°±0.2°.

Figure 11:
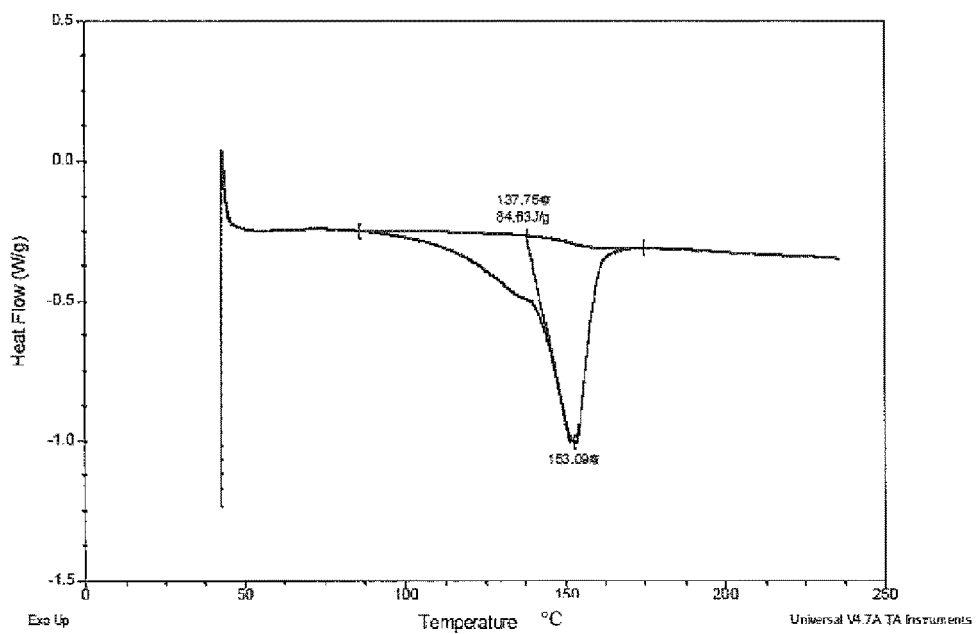
FIG. 11 shows the results of a DSC experiment for Form IV; first cycle is shown in the upper panel and second cycle is shown in the lower panel.
Figure 11:
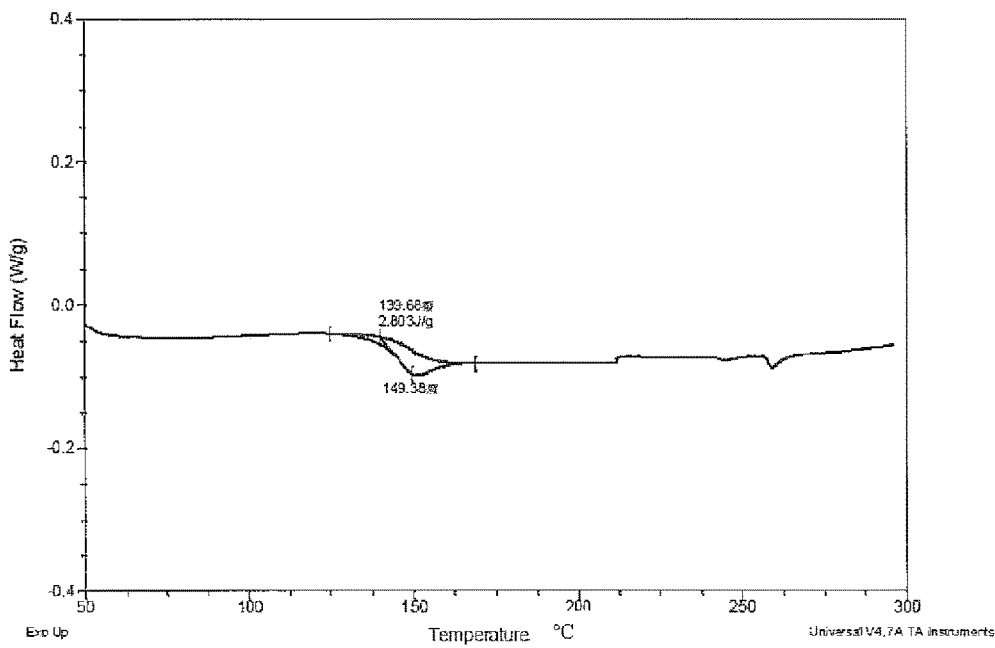

In some embodiments, Form IV characterized by a DSC thermogram comprising an endothermic peak having a maximum at about 153° C. In some embodiments, crystalline Form IV has a DSC thermogram substantially as shown in FIG. 11.

Figure 12:
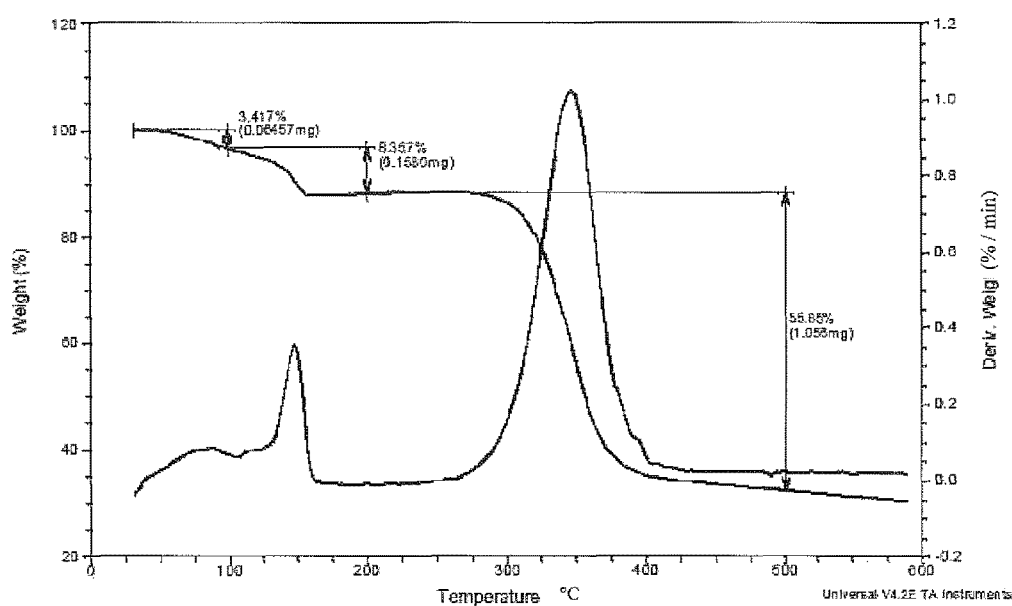
FIG. 12 shows the results of a TGA experiment for Form IV.

In some embodiments, crystalline Form IV has a TGA trace substantially as shown in FIG. 12.

Crystalline Form V

In some embodiments, the crystalline form of the compound of Formula I is Form V. Crystalline Form V can be prepared by combining Form I with isobutyl acetate. The resulting mixture can be optionally heated.

Figure 13:
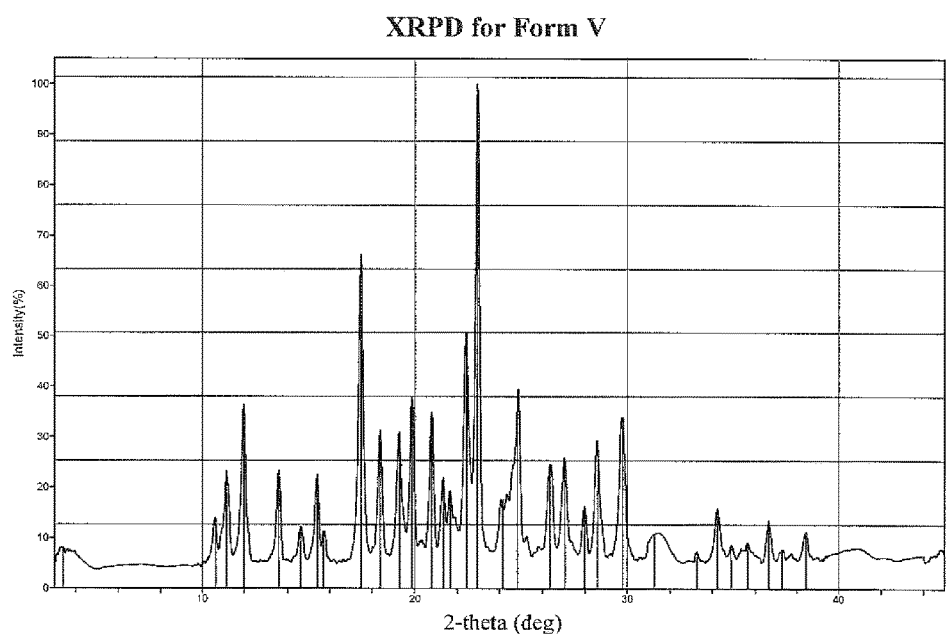
FIG. 13 shows an XRPD pattern for Form V.

Crystalline Form V can be identified by unique signatures with respect to, for example, XRPD, DSC, and TGA. In some embodiments, crystalline Form V is characterized by an XRPD pattern substantially as shown in FIG. 13. Peaks from the XRPD pattern are listed in Table 14.

In some embodiments, crystalline Form V is characterized by an XRPD pattern comprising a peak, in terms of 2θ, at 12.0°±0.2°. In some embodiments, crystalline Form V has an XRPD pattern comprising the following peaks, in terms of 2θ: 12.0°±0.2°; 13.6°±0.2°; 17.5°±0.2°; and 22.9°±0.2°. In some embodiments, crystalline Form V has an XRPD pattern comprising 2 or more, 3 or more, or 4 or more of the following peaks, in terms of 2θ: 11.1°±0.2°; 12.0°±0.2°; 13.6°±0.2°; 15.4°±0.2°; 17.5°±0.2°; 19.9°±0.2°; 22.4°±0.2°; 22.9°±0.2°; and 24.8°±0.2°.

Figure 14:
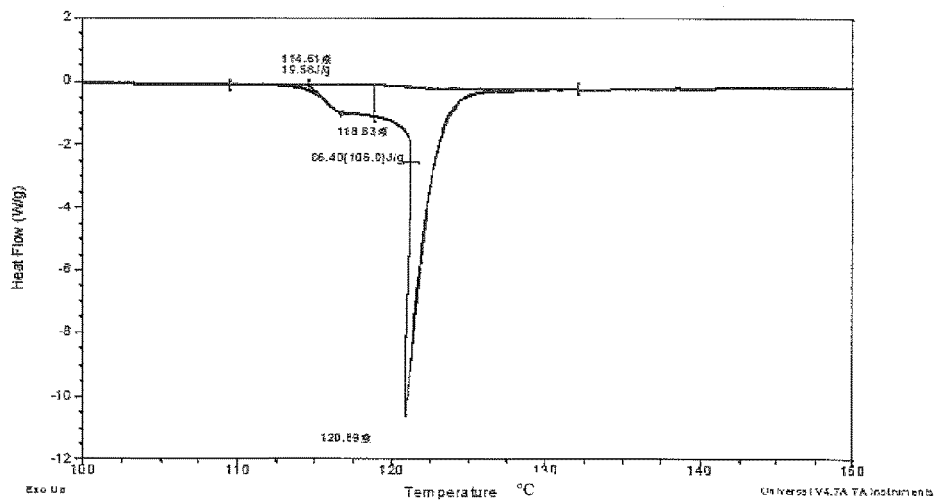
FIG. 14 shows the results of a DSC experiment for Form V; first cycle is shown in the upper panel and second cycle is shown in the lower panel.
Figure 14:
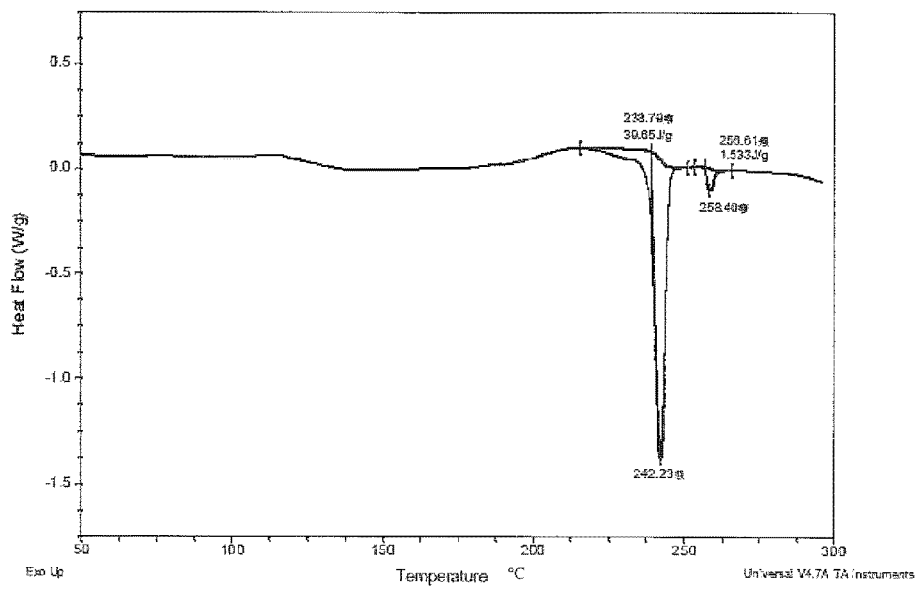

In some embodiments, Form V is characterized by a DSC thermogram comprising an endothermic peak having a maximum at about 153° C. In some embodiments, crystalline Form V of the compound of Formula I is characterized by the DSC thermogram substantially as shown in FIG. 14 (upper).

Figure 15:
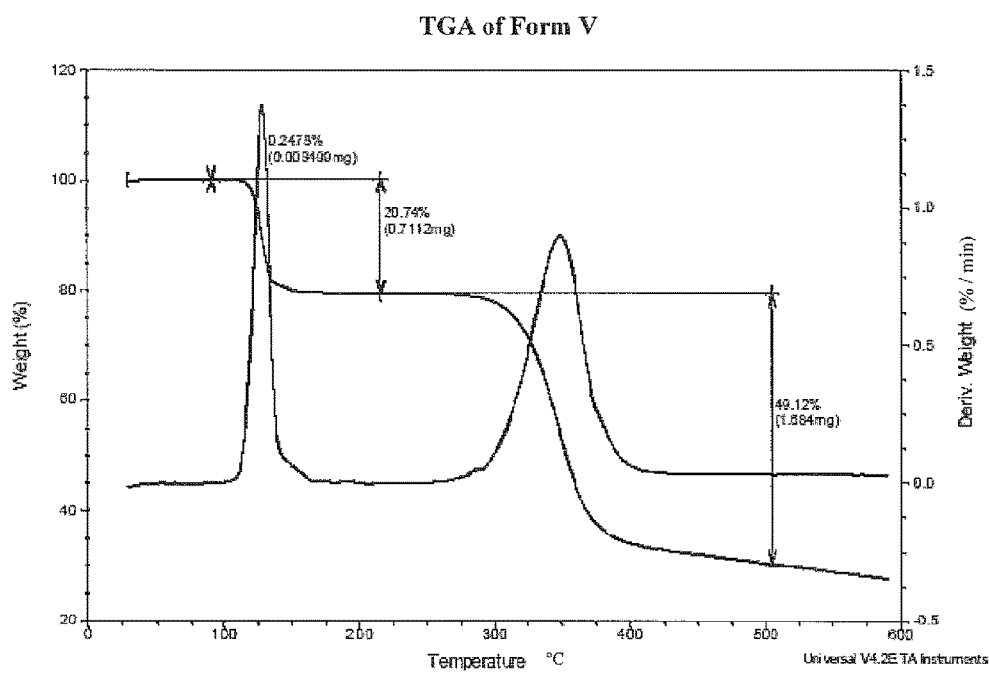
FIG. 15 shows the results of a TGA experiment for Form V.

In some embodiments, crystalline Form V has a TGA trace substantially as shown in FIG. 15.

Crystalline Form VI

In some embodiments, the crystalline form of the compound of Formula I is crystalline Form VI. This crystalline form appears to be hydrated, e.g., a hemihydrate based on, for example, TGA data supplied herein.

In some embodiments, the invention provides a process for preparing crystalline Form VI comprising combining crystalline Form I with water. In some embodiments, the process further comprises heating the mixture resulting from the combining of crystalline Form I and water. In some embodiments, the mixture can be heated to between about 30 and about 70° C., between about 40 and about 60° C., or at about 50° C. to yield Form VI.

Figure 16:
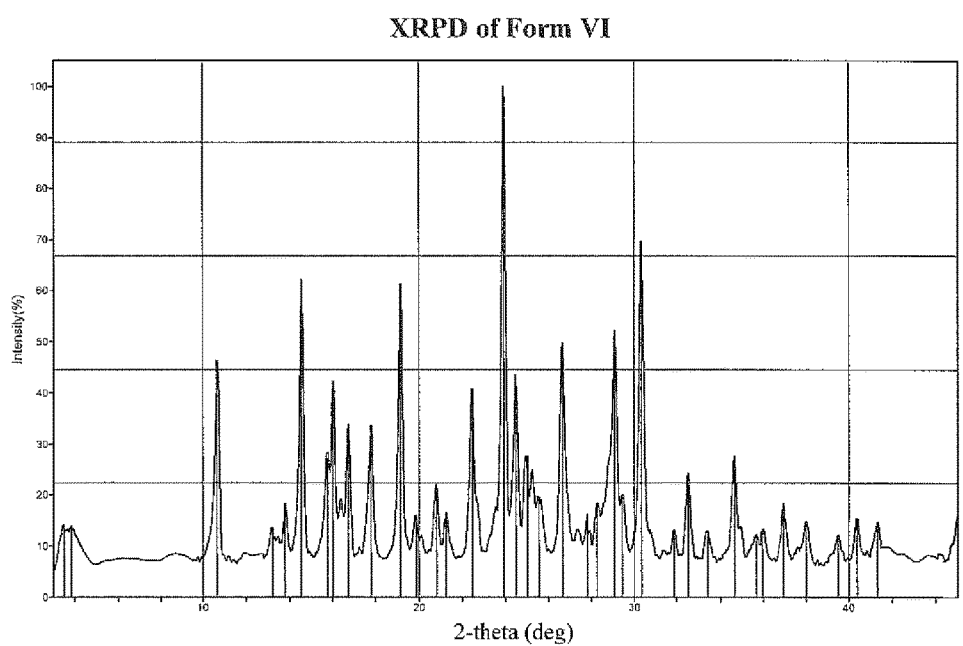
FIG. 16 shows an XRPD pattern for Form VI.

In some embodiments, crystalline Form VI can be identified by unique signatures with respect to, for example, XRPD, DSC, and TGA. In some embodiments, crystalline Form VI is characterized by an XRPD pattern substantially as shown in FIG. 16. Peaks from the XRPD pattern are listed in Table 15.

In some embodiments, crystalline Form VI is characterized by an XRPD pattern comprising a peak, in terms of 2θ, at 10.7°±0.2°. In some embodiments, crystalline Form VI has an XRPD pattern comprising the following peaks, in terms of 2θ: 10.7°±0.2°; 14.6°±0.2°; 19.1°±0.2°; and 23.9°±0.2°. In some embodiments, crystalline Form VI has an XRPD pattern comprising 2 or more, 3 or more, or 4 or more of the following peaks, in terms of 2θ: 10.7°±0.2°; 14.6°±0.2°; 16.0°±0.2°; 19.1°±0.2°; 22.4°±0.2°; 23.9°±0.2°; 24.5°±0.2°; 26.7°±0.2°; 29.1°±0.2°; 30.3°±0.2°; and 34.7°±0.2°.

Figure 17:
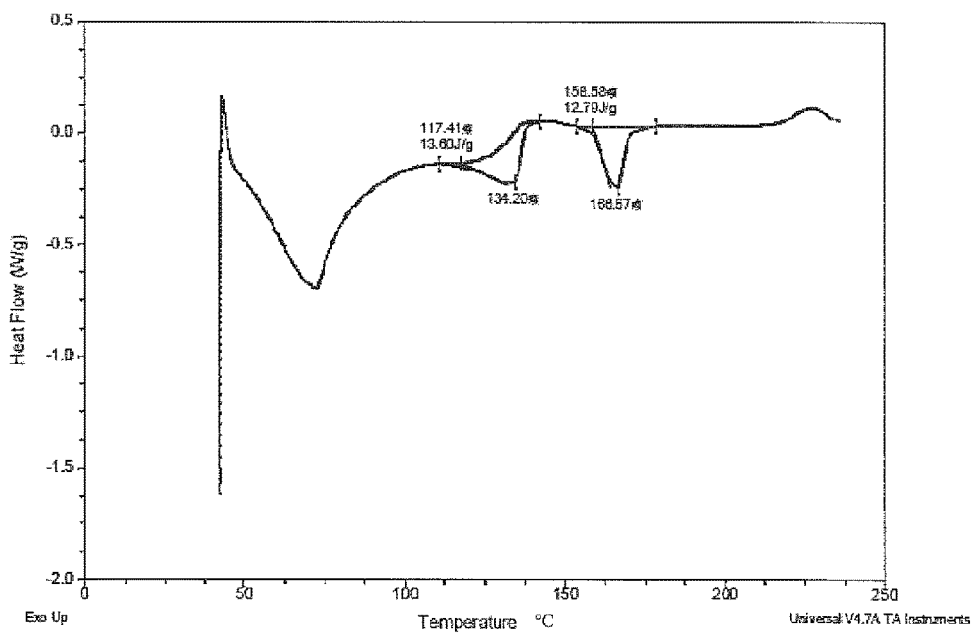
FIG. 17 shows the results of a DSC experiment for Form VI; first cycle is shown in the upper panel and second cycle is shown in the lower panel.
Figure 17:
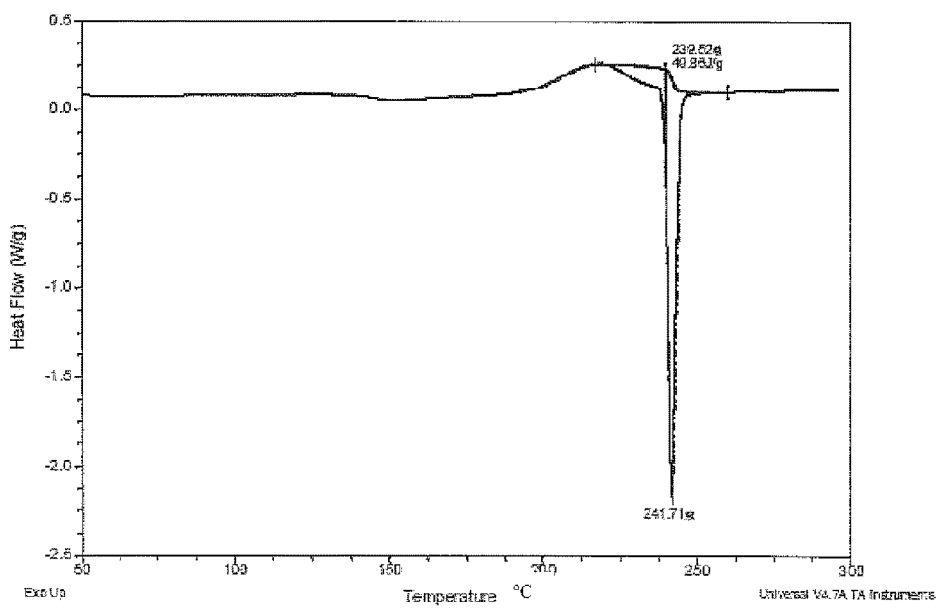

In some embodiments, crystalline Form VI is characterized by the DSC thermogram substantially as shown in FIG. 17 (upper).

Figure 18:
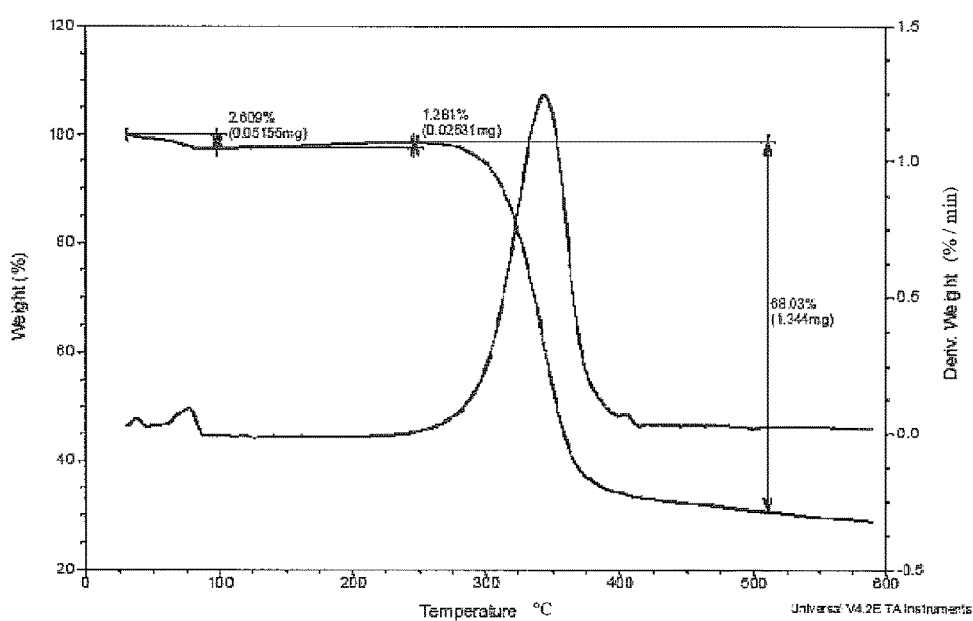
FIG. 18 shows the results of a TGA experiment for Form VI.

In some embodiments, crystalline Form VI has a TGA trace substantially as shown in FIG. 18. In some embodiments, the Form VI has a TGA trace showing about 2.6% weight loss up to about 100° C.

Crystalline Form VII

In some embodiments, the crystalline form of the compound of Formula I is Form VII. Crystalline Form VII of the compound of Formula I can be prepared by combining Form I with 1,4-dioxane, methyl isobutyl ketone, or water, or mixtures of any of the aforementioned. The resulting mixture can be optionally heated.

Figure 19:
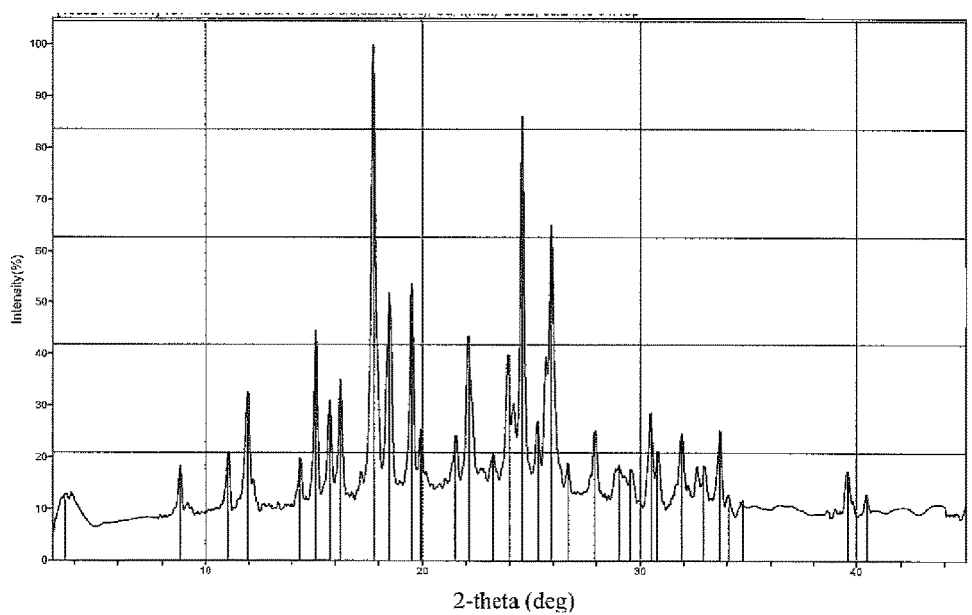
FIG. 19 shows an XRPD pattern for Form VII.

Crystalline Form VII can be identified by unique signatures with respect to, for example, XRPD, DSC, and TGA. In some embodiments, crystalline Form VII of the compound of Formula I is characterized by an XRPD pattern substantially as shown in FIG. 19. Peaks from the XRPD pattern are listed in Table 16.

In some embodiments, crystalline Form VII is characterized by an XRPD comprising a peak, in terms of 2θ, at 12.0°±0.2°. In some embodiments, crystalline Form VII has an XRPD pattern comprising the following peaks, in terms of 2θ: 12.0°±0.2°; 15.1°±0.2°; 17.8°±0.2°; and 24.6°±0.2°. In some embodiments, crystalline Form VII of the compound of Formula I has an XRPD pattern comprising 2 or more, 3 or more, or 4 or more of the following peaks, in terms of 2θ: 8.8°±0.2°; 11.0°±0.2°; 12.0°±0.2°; 15.1°±0.2°; 15.8°±0.2°; 16.2°±0.2°; 17.8°±0.2°; 18.5°±0.2°; 19.5°±0.2°; 22.1°±0.2°; 24.6°±0.2°; and 25.9°±0.2°.

Figure 21:
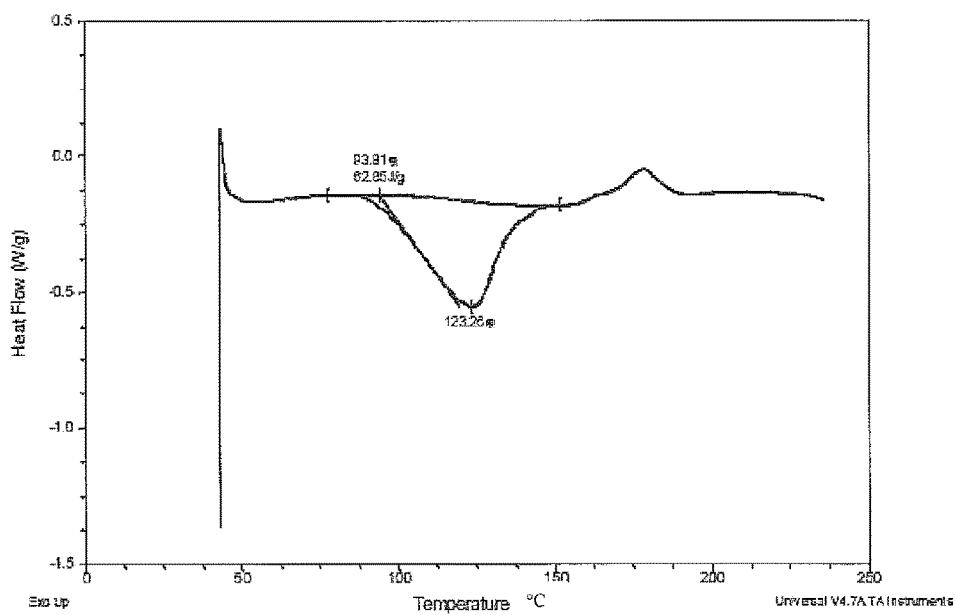
FIG. 21 shows the results of a DSC experiment for Form VII; first cycle is shown in the upper panel and second cycle is shown in the lower panel.
Figure 21:
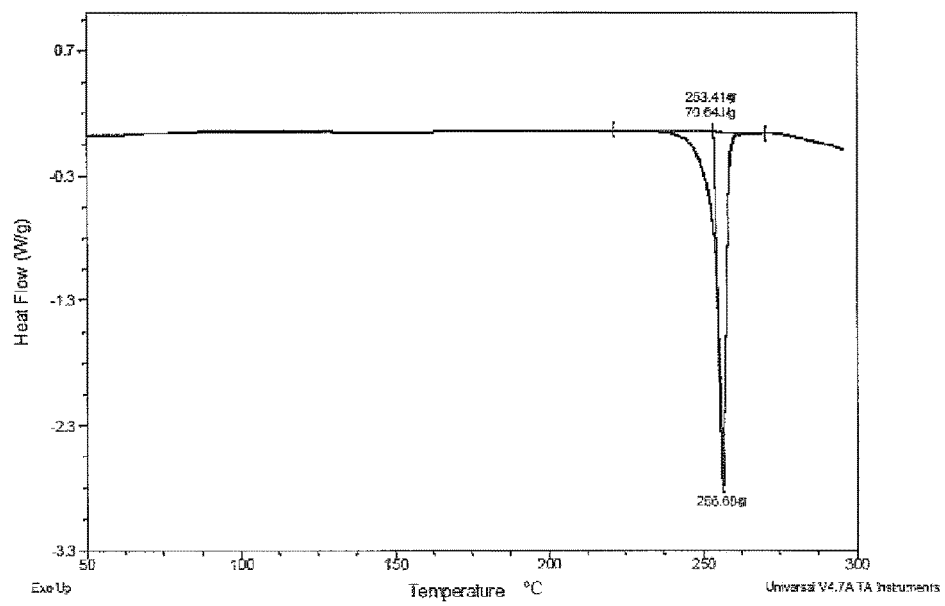

In some embodiments, Form VII is characterized by a DSC thermogram comprising an endothermic peak having a maximum at about 123° C. In some embodiments, crystalline Form VII is characterized by the DSC thermogram substantially as shown in FIG. 21 (upper).

Figure 20:
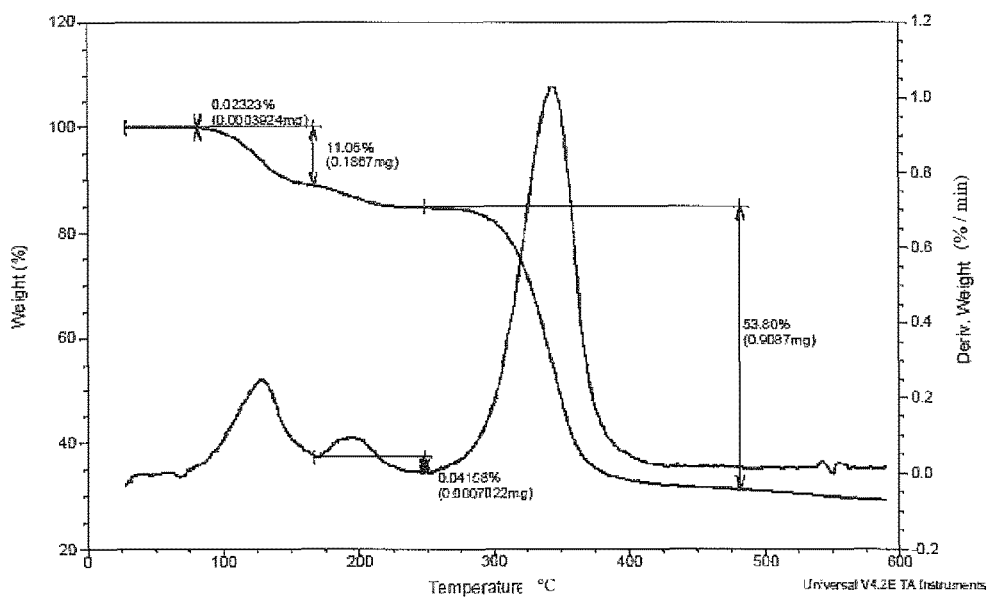
FIG. 20 shows the results of a TGA experiment for Form VII.

In some embodiments, crystalline Form VII has a TGA trace substantially as shown in FIG. 20.

Crystalline Form VIII

In some embodiments, the crystalline form of the compound of Formula I is Form VIII. Crystalline Form VIII can be prepared by combining Form I with n-butyl alcohol. The resulting mixture can be optionally heated.

Figure 22:
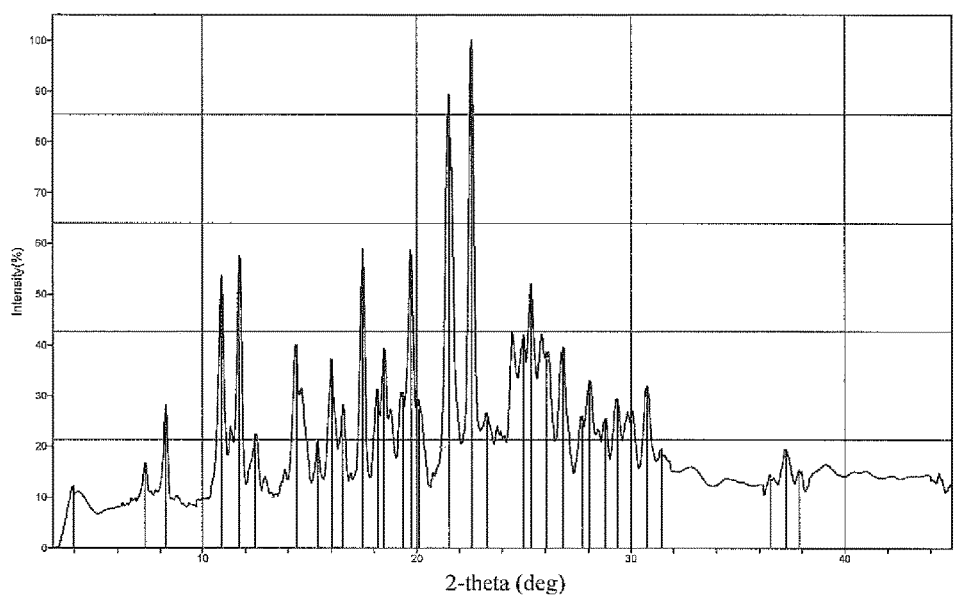
FIG. 22 shows an XRPD pattern for Form VIII.

Crystalline Form VIII can be identified by unique signatures with respect to, for example, XRPD, DSC, and TGA. In some embodiments, crystalline Form VIII is characterized by an XRPD pattern substantially as shown in FIG. 22. Peaks from the XRPD pattern are listed in Table 17.

In some embodiments, crystalline Form VIII is characterized by an XRPD pattern comprising a peak, in terms of 2θ, at 10.9°±0.2°. In some embodiments, crystalline Form VIII has an XRPD pattern comprising the following peaks, in terms of 2θ: 10.9°±0.2°; 11.7°±0.2°; 21.5°±0.2°; and 22.6°±0.2°. In some embodiments, crystalline Form VIII has an XRPD pattern comprising 2 or more, 3 or more, or 4 or more of the following peaks, in terms of 2θ: 3.9°±0.2°; 8.2°±0.2°; 10.9°±0.2°; 11.7°±0.2°; 14.4°±0.2°; 16.1°±0.2°; 17.5°±0.2°; 19.7°±0.2°; 21.5°±0.2°; 22.6°±0.2°; and 25°0.3±0.2°.

Figure 23:
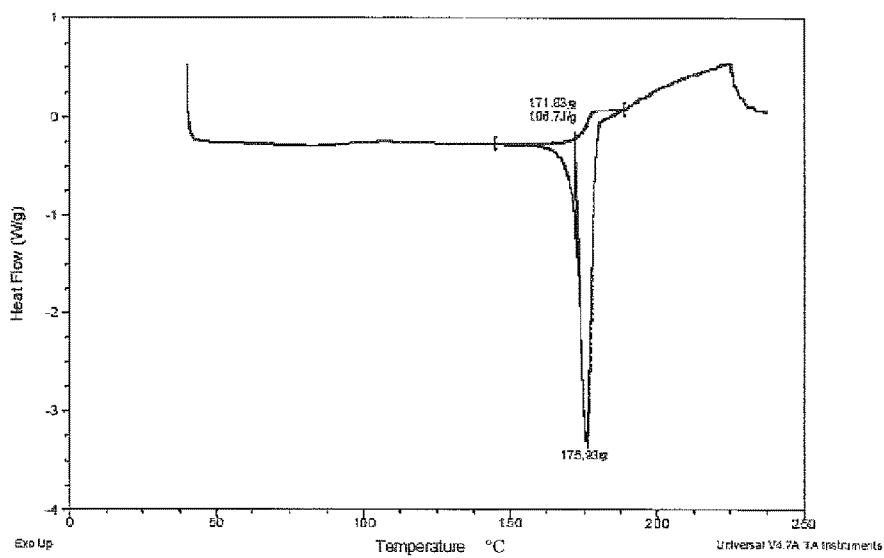
FIG. 23 shows the results of a DSC experiment for Form VIII; first cycle is shown in the upper panel and second cycle is shown in the lower panel.
Figure 23:
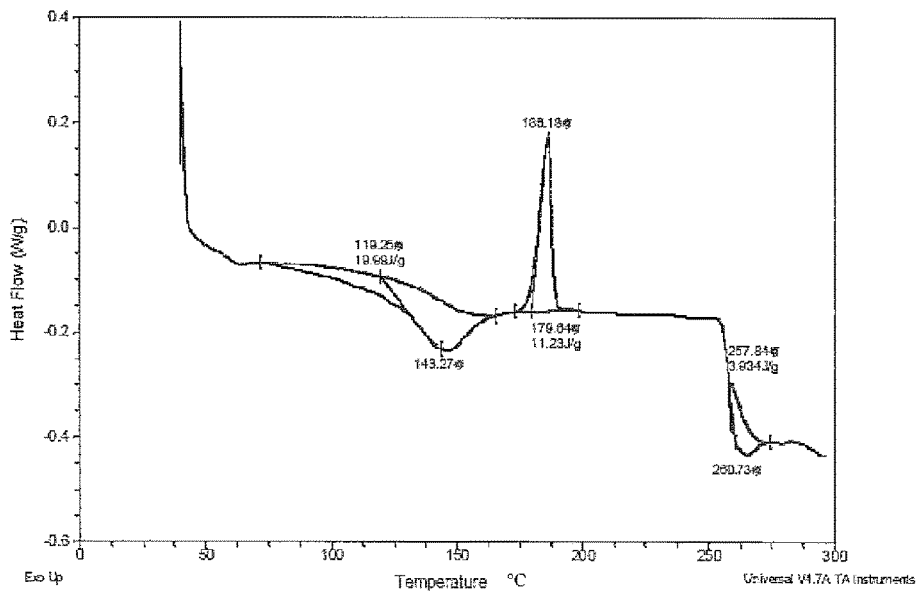

In some embodiments, Form VIII is characterized by a DSC thermogram comprising an endothermic peak having a maximum at about 176° C. In some embodiments, crystalline Form VIII characterized by the DSC thermogram substantially as shown in FIG. 23 (upper).

Figure 24:
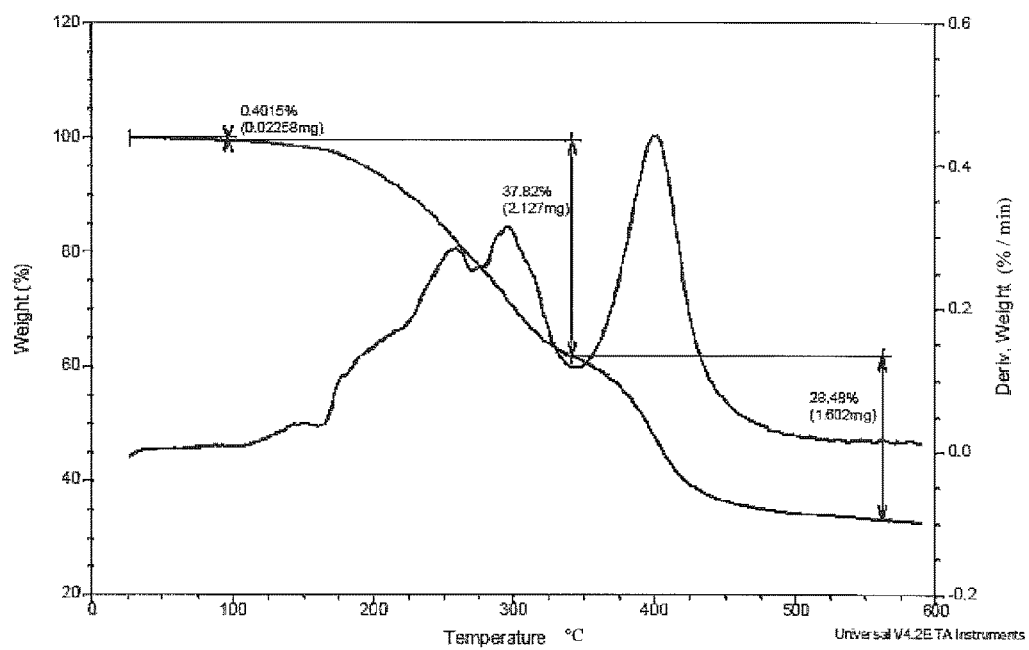
FIG. 24 shows the results of a TGA experiment for Form VIII.

In some embodiments, crystalline Form VIII has a TGA trace substantially as shown in FIG. 24.

Crystalline Form IX

In some embodiments, the crystalline form of the compound of Formula I is Form IX. Crystalline Form IX can be prepared by combining Form I with methyl isobutyl ketone. The resulting mixture can be optionally heated.

Figure 25:
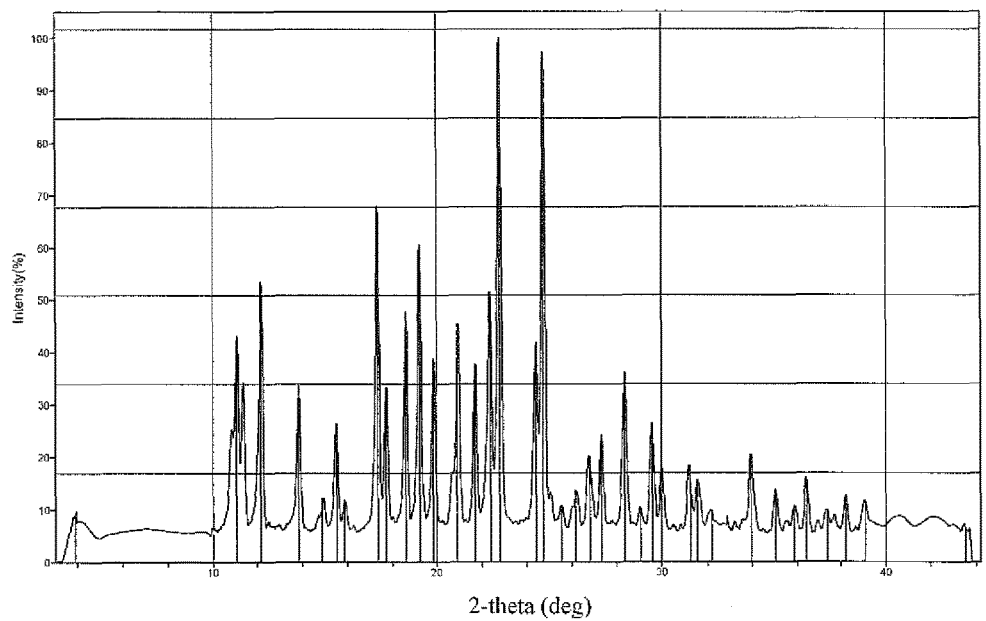
FIG. 25 shows an XRPD pattern for Form IX.

Crystalline Form IX can be identified by unique signatures with respect to, for example, XRPD, DSC, and TGA. In some embodiments, crystalline Form IX of the compound of Formula I is characterized by an XRPD pattern substantially as shown in FIG. 25. Peaks from the XRPD pattern are listed in Table 18.

In some embodiments, crystalline Form IX is characterized by an XRPD pattern comprising a peak, in terms of 2θ, at 13.8°±0.2°. In some embodiments, crystalline Form IX has an XRPD pattern comprising the following peaks, in terms of 2θ: 13.8°±0.2°; 17.4°±0.2°; 22.8°±0.2°; and 24.8°±0.2°. In some embodiments, crystalline Form IX has an XRPD pattern comprising 2 or more, 3 or more, or 4 or more of the following peaks, in terms of 2θ: 11.1°±0.2°; 12.2°±0.2°; 13.8°±0.2°; 15.5°±0.2°; 17.4°±0.2°; 19.3°±0.2°; 20.9°±0.2°; 22.4°±0.2°; 22.8°±0.2°; and 24.8°±0.2°.

Figure 26:
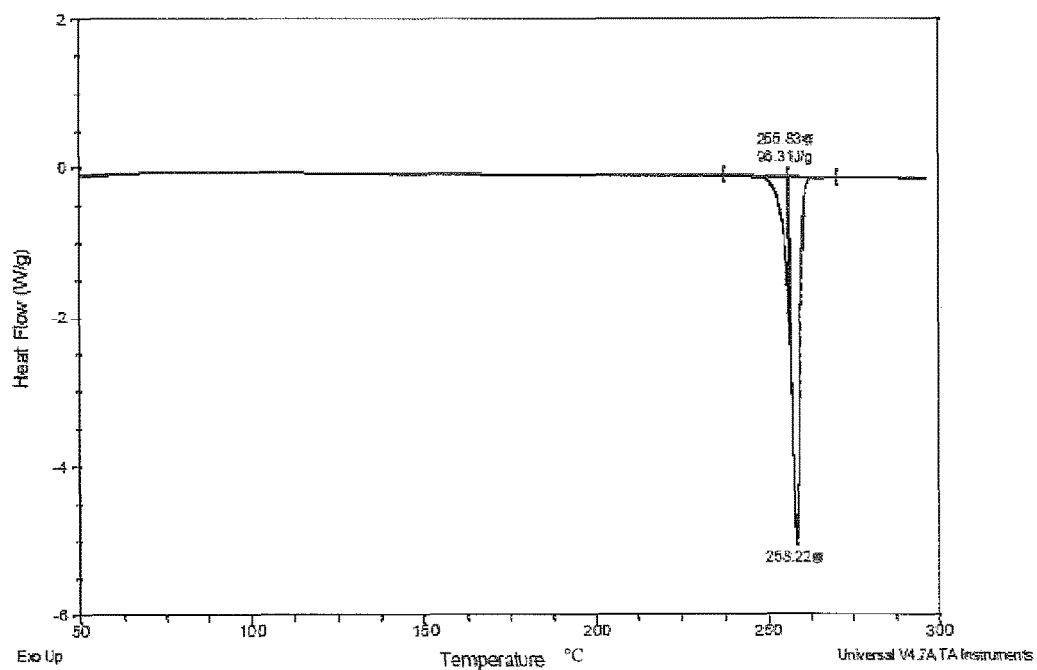
FIG. 26 shows the results of a DSC experiment for Form IX.

In some embodiments, Form IX is characterized by a DSC thermogram comprising an endothermic peak having a maximum at about 256° C. In some embodiments, crystalline Form IX is characterized by the DSC thermogram substantially as shown in FIG. 26.

Figure 27:
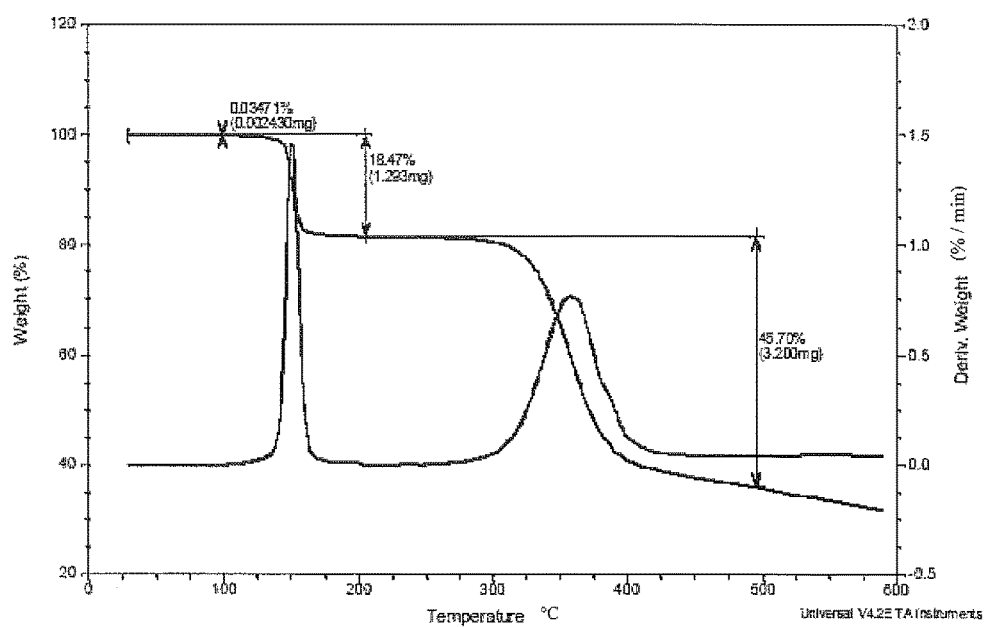
FIG. 27 shows the results of a TGA experiment for Form IX.

In some embodiments, crystalline Form IX has a TGA trace substantially as shown in FIG. 27.

Crystalline Form X

In some embodiments, the crystalline form of the compound of Formula I is Form X. In some embodiments, Form X can be prepared by a process comprising combining Form I with acetone. In some embodiments, the process further comprises heating the mixture resulting from the combining of crystalline Form I and acetone. In some embodiments, the mixture is heated to about 30 to about 70° C., about 40 to about 60° C., or about 50° C. to yield Form X.

Figure 28:
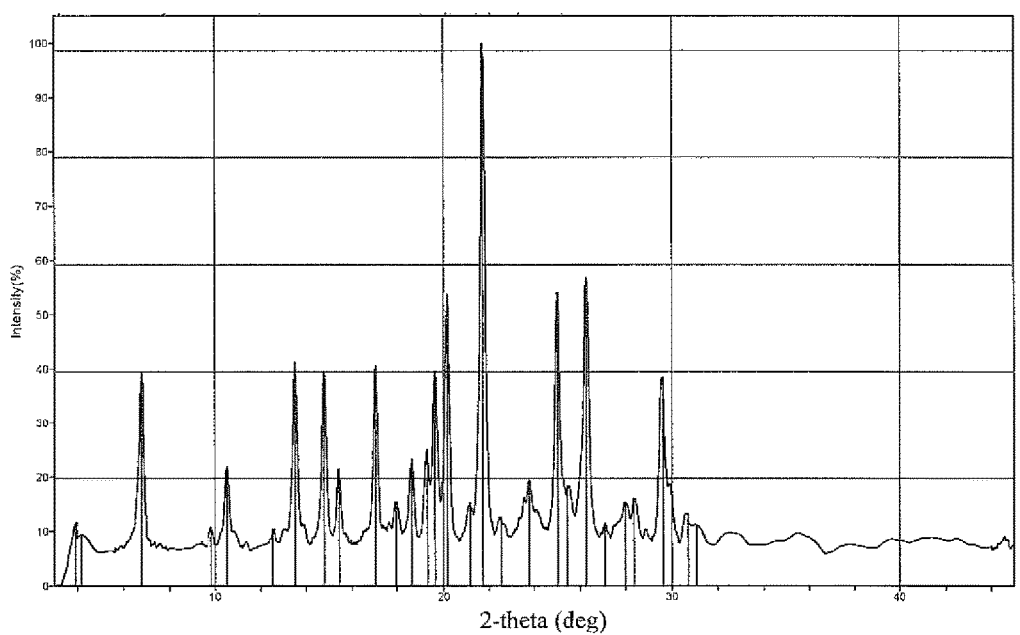
FIG. 28 shows an XRPD pattern for Form X.

Crystalline Form X can be identified by unique signatures with respect to, for example, XRPD, DSC, and TGA. In some embodiments, crystalline Form X is characterized by an XRPD pattern substantially as shown in FIG. 28. Peaks from the XRPD pattern are listed in Table 19.

In some embodiments, crystalline Form X is characterized by an XRPD pattern comprising a peak, in terms of 2θ, at 6.8°±0.2°. In some embodiments, crystalline Form X has an XRPD pattern comprising the following peaks, in terms of 2θ: 6.8°±0.2°; 13.5°±0.2°; 14.8°±0.2°; and 17.0°±0.2°. In some embodiments, crystalline Form X has an XRPD pattern comprising 2 or more, 3 or more, or 4 or more of the following peaks, in terms of 2θ: 6.8°±0.2°; 13.5°±0.2°; 14.8°±0.2°; 17.0°±0.2°; 19.6°±0.2°; 20.2°±0.2°; 21.7°±0.2°; 25.0°±0.2°; and 26.3°±0.2°.

Figure 29:
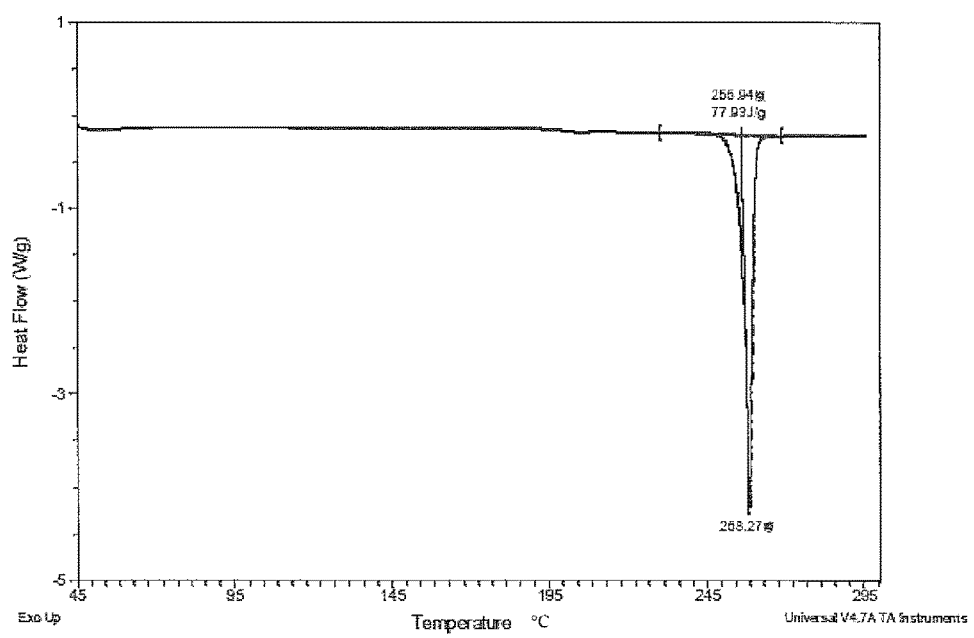
FIG. 29 shows the results of a DSC experiment for Form X.

In some embodiments, Form X is characterized by a DSC thermogram comprising an endothermic peak having a maximum at about 258° C. In some embodiments, crystalline Form X is characterized by the DSC thermogram substantially as shown in FIG. 29.

Figure 30:
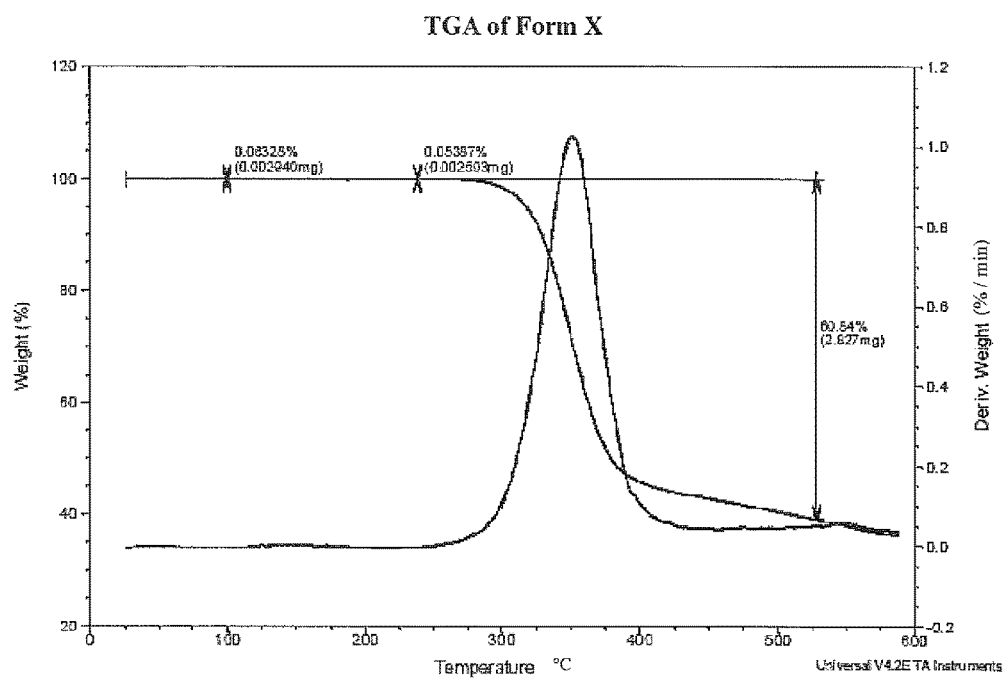
FIG. 30 shows the results of a TGA experiment for Form X.

In some embodiments, crystalline Form X has a TGA trace substantially as shown in FIG. 30.

Crystalline Form XI

In some embodiments, the crystalline form of the compound of Formula I is Form XI. Crystalline Form XI can be prepared by combining Form I with tetrahydrofuran or isobutyl acetate. The resulting mixture can be optionally heated.

Figure 31:
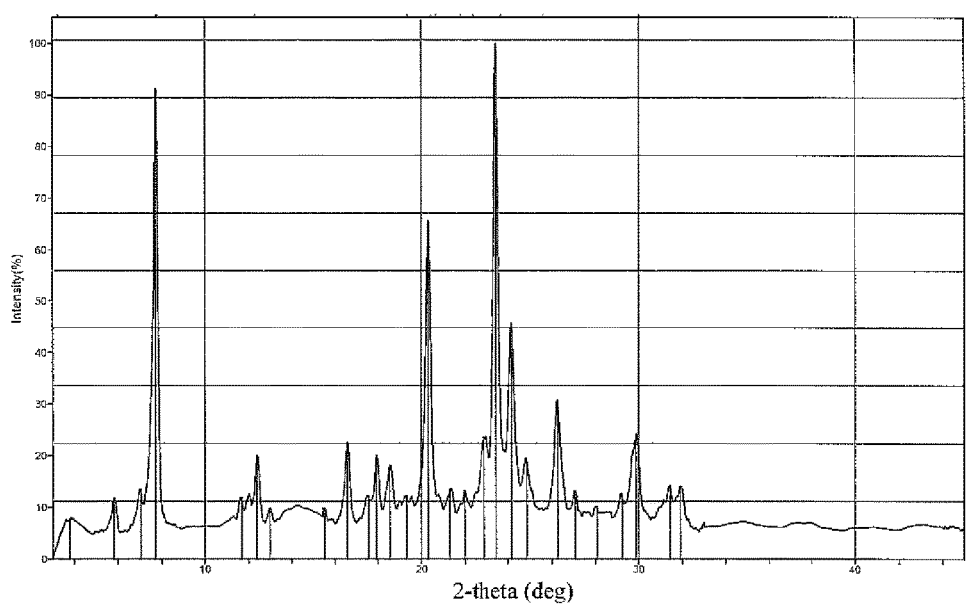
FIG. 31 shows an XRPD pattern for Form XI.

Crystalline Form XI can be identified by unique signatures with respect to, for example, XRPD and DSC. In some embodiments, crystalline Form XI is characterized by an XRPD pattern substantially as shown in FIG. 31. Peaks from the XRPD pattern are listed in Table 20.

In some embodiments, crystalline Form XI is characterized by an XRPD pattern comprising a peak, in terms of 2θ, at 7.7°±0.2°. In some embodiments, crystalline Form XI has an XRPD pattern comprising the following peaks, in terms of 2θ: 7.7°±0.2°; 20.3°±0.2°; and 23.4°±0.2°. In some embodiments, crystalline Form XI has an XRPD pattern comprising 2 or more, 3 or more, or 4 or more of the following peaks, in terms of 2θ: 7.7°±0.2°; 12.4°±0.2°; 16.6°±0.2°; 20.3°±0.2°; 23.4°±0.2°; 24.2°±0.2°; 26.3°±0.2°; and 29.9°±0.2°.

Figure 32:
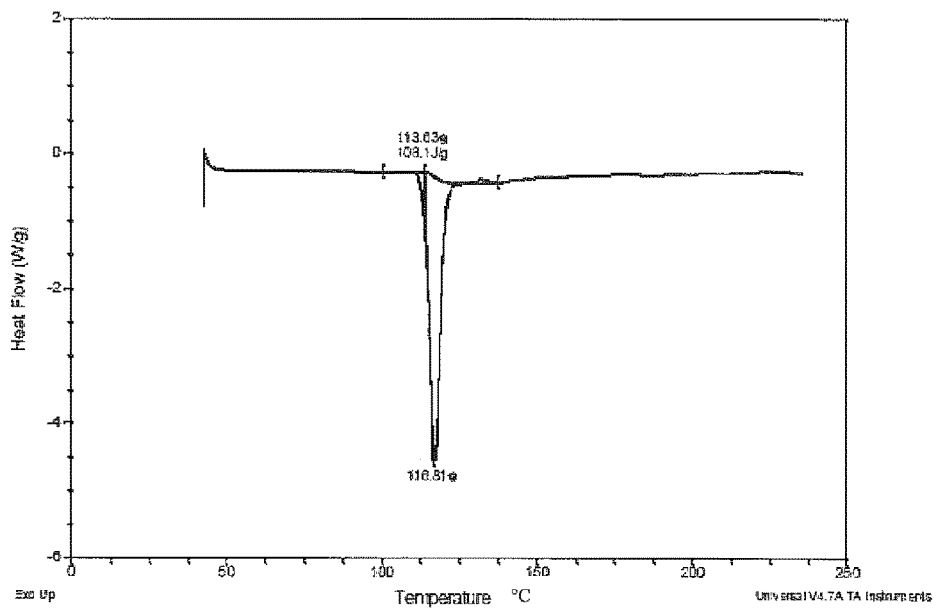
FIG. 32 shows the results of a DSC experiment for Form XI; first cycle is shown in the upper panel and second cycle is shown in the lower panel.
Figure 32:
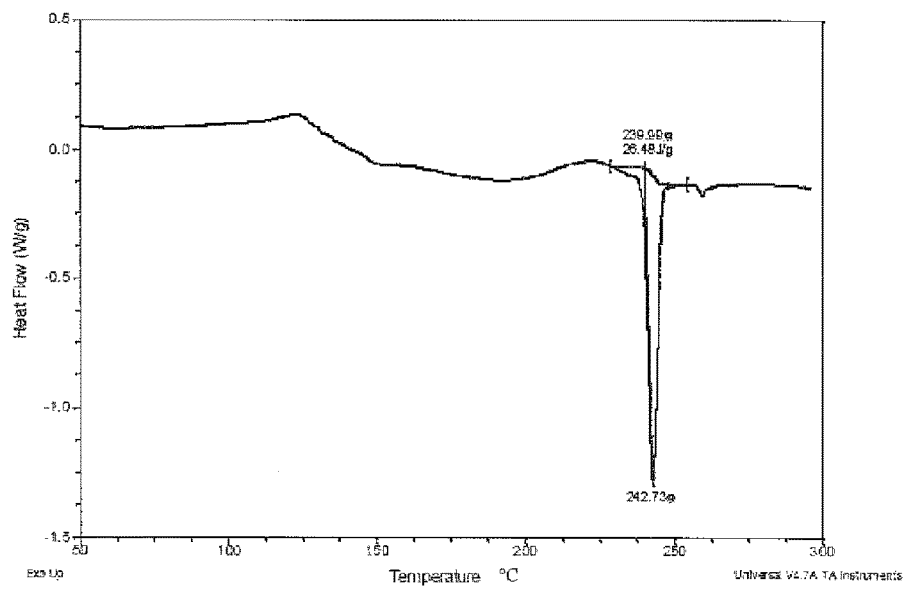

In some embodiments, Form IX is characterized by a DSC thermogram comprising an endothermic peak having a maximum at about 117° C. In some embodiments, crystalline Form XI is characterized by the DSC thermogram substantially as shown in FIG. 32 (upper).

Crystalline Form XII

In some embodiments, the crystalline form of the compound of Formula I is Form XII. Crystalline Form XII can be prepared by combining Form I with methyl t-butyl ether. The preparation method can optionally further comprise heating the resulting mixture.

Figure 33:
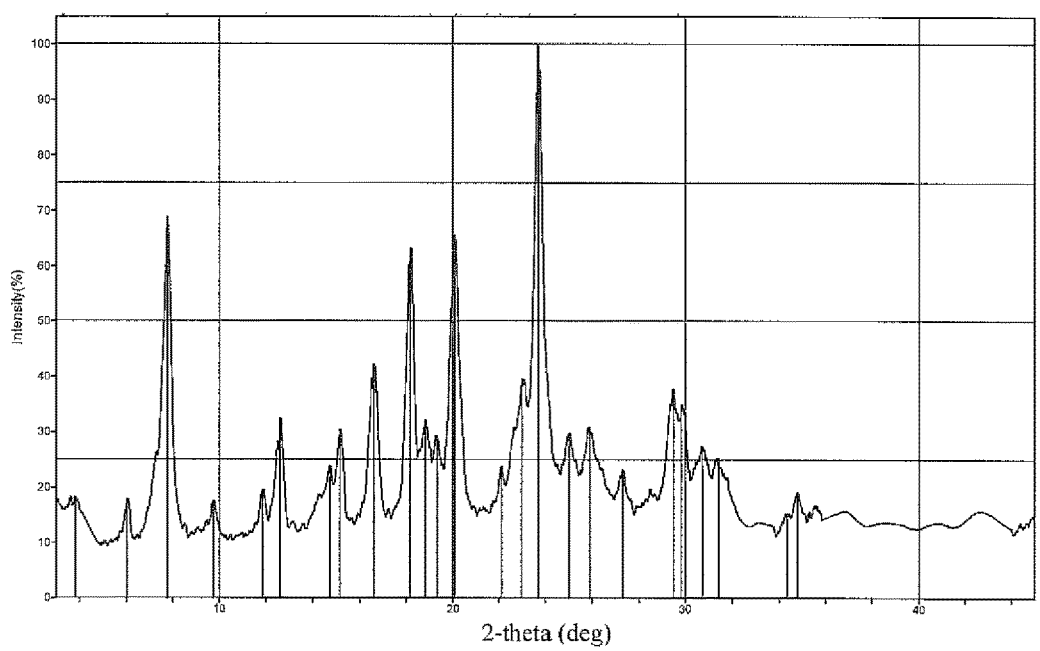
FIG. 33 shows an XRPD pattern for Form XII.

Crystalline Form XII can be identified by unique signatures with respect to, for example, XRPD and DSC. In some embodiments, crystalline Form XII is characterized by an XRPD pattern substantially as shown in FIG. 33. Peaks from the XRPD pattern are listed in Table 21.

In some embodiments, crystalline Form XII is characterized by an XRPD pattern comprising a peak, in terms of 2θ, at 7.8°±0.2°. In some embodiments, crystalline Form XII has an XRPD pattern comprising the following peaks, in terms of 2θ: 7.8°±0.2°; 18.2°±0.2°; 20.1°±0.2°; and 23.7°±0.2°. In some embodiments, crystalline Form XII has an XRPD pattern comprising 4 or more of the following peaks, in terms of 2θ: 7.8°±0.2°; 12.6°±0.2°; 16.6°±0.2°; 18.2°±0.2°; 20.1°±0.2°; and 23.7°±0.2°.

Figure 34:
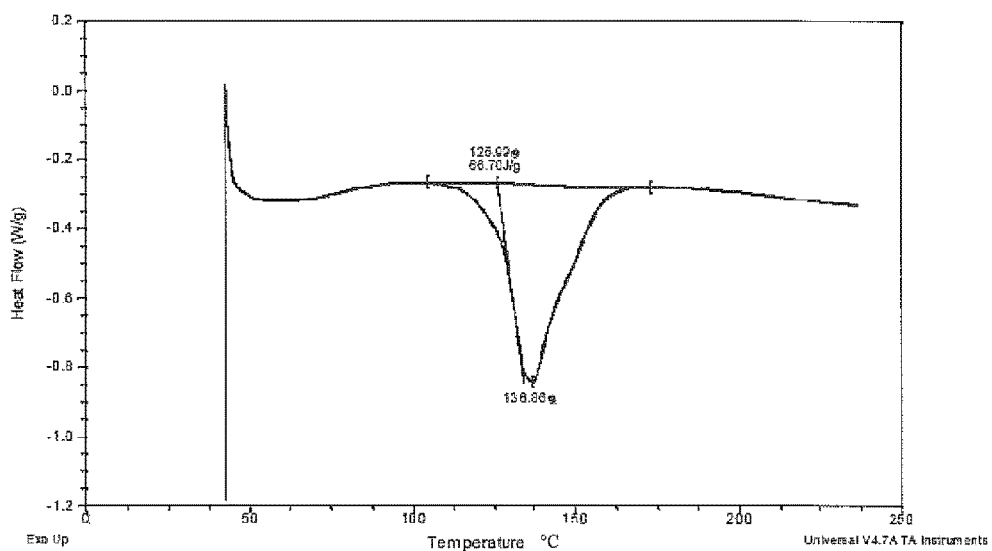
FIG. 34 shows the results of a DSC experiment for Form XII.

In some embodiments, Form XII is characterized by a DSC thermogram comprising an endothermic peak having a maximum at about 137° C. In some embodiments, crystalline Form XII is characterized by the DSC trace substantially as shown in FIG. 34.

Crystalline Form XIII

In some embodiments, the crystalline form of the compound of Formula I is Form XIII. Crystalline Form XIII of the compound of Formula I can be prepared by combining Form I with ethanol or 2-methoxyethanol, or mixtures thereof. The preparation method can optionally further comprise heating the resulting mixture.

Figure 35:
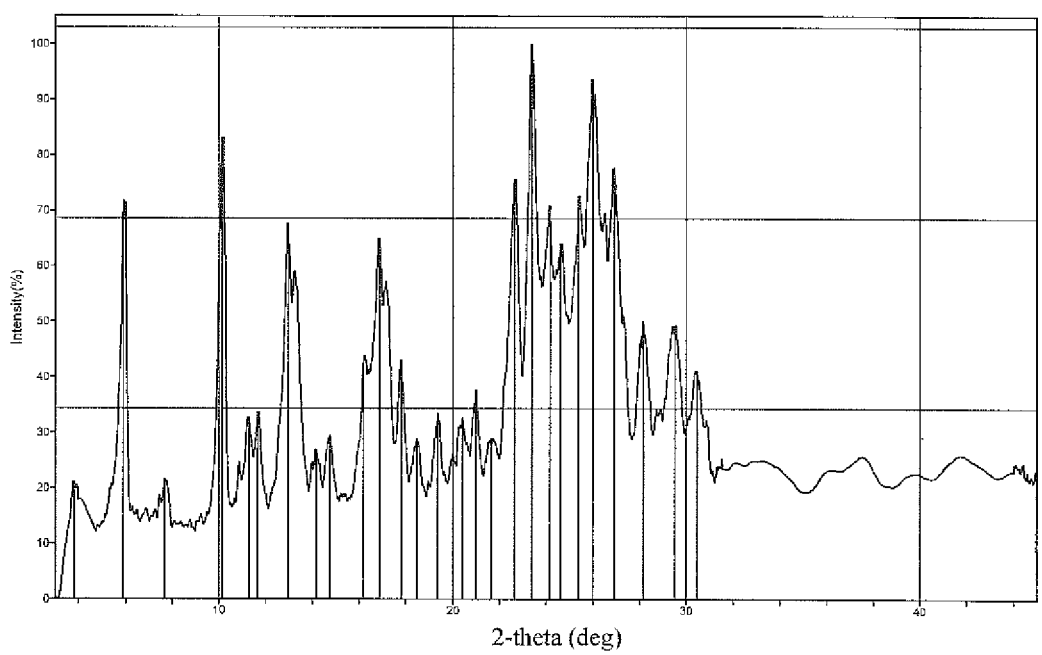
FIG. 35 shows an XRPD pattern for Form XIII.

Crystalline Form XIII can be identified by unique signatures with respect to, for example, XRPD and DSC. For example, in some embodiments, crystalline Form XIII is characterized by an XRPD pattern substantially as shown in FIG. 35. Peaks from the XRPD pattern are listed in Table 22.

In some embodiments, crystalline Form XIII is characterized by an XRPD pattern comprising a peak, in terms of 2θ, at 5.9°±0.2°. In some embodiments, crystalline Form XIII has an XRPD pattern comprising the following peaks, in terms of 2θ: 5.9°±0.2°; 10.1°±0.2°; 13.0°±0.2°; and 16.9°±0.2°. In some embodiments, crystalline Form XIII has an XRPD pattern comprising 2 or more, 3 or more, or 4 or more of the following peaks, in terms of 2θ: 3.8°±0.2°; 5.9°±0.2°; 10.1°±0.2°; 13.0°±0.2°; 16.9°±0.2°; 23.4°±0.2°; 26.0°±0.2°; and 26.9°±0.2°.

Figure 36:
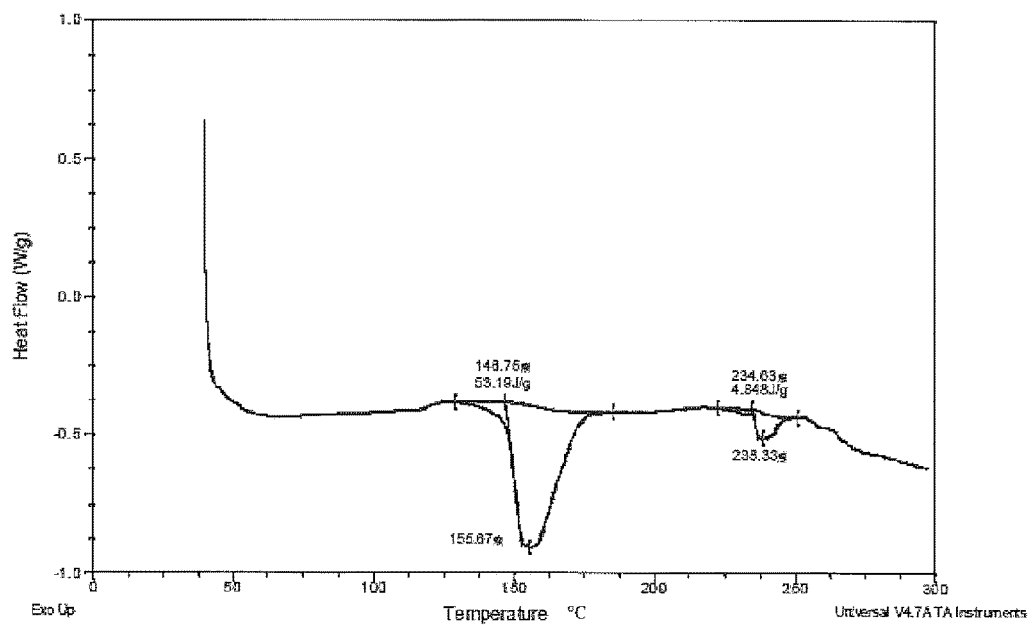
FIG. 36 shows the results of a DSC experiment for Form XIII.

In some embodiments, crystalline Form XIII is characterized by the DSC thermogram substantially as shown in FIG. 36.

Methods

The crystalline forms of the invention can modulate activity of one or more of various kinases including, for example, phosphoinositide 3-kinases (PI3Ks). The term "modulate" is meant to refer to an ability to increase or decrease the activity of one or more members of the PI3K family. Accordingly, the crystalline forms of the invention can be used in methods of modulating a PI3K by contacting the PI3K with any one or more of the crystalline forms or compositions described herein. In some embodiments, crystalline forms of the present invention can act as inhibitors of one or more PI3Ks. In further embodiments, the compounds of the invention can be used to modulate activity of a PI3K in an individual in need of modulation of the receptor by administering a modulating amount of a crystalline form of the invention, or a pharmaceutically acceptable salt thereof. In some embodiments, modulating is inhibiting.

Given that cancer cell growth and survival is impacted by multiple signaling pathways, the present invention is useful for treating disease states characterized by drug resistant kinase mutants. In addition, different kinase inhibitors, exhibiting different preferences in the kinases which they modulate the activities of, may be used in combination. This approach could prove highly efficient in treating disease states by targeting multiple signaling pathways, reduce the likelihood of drug-resistance arising in a cell, and reduce the toxicity of treatments for disease.

Kinases to which the present crystalline forms bind and/or modulate (e.g., inhibit) include any member of the PI3K family. In some embodiments, the PI3K is PI3Kα, PI3Kβ, PI3Kγ, or PI3Kδ. In some embodiments, the PI3K is PI3Kγ or PI3Kδ. In some embodiments, the PI3K is PI3Kγ. In some embodiments, the PI3K is PI3Kδ. In some embodiments, the PI3K includes a mutation. A mutation can be a replacement of one amino acid for another, or a deletion of one or more amino acids. In such embodiments, the mutation can be present in the kinase domain of the PI3K.

In some embodiments, more than one crystalline form of the invention is used to inhibit the activity of one kinase (e.g., PI3Kγ or PI3Kδ).

In some embodiments, more than one crystalline form of the invention is used to inhibit more than one kinase, such as at least two kinases (e.g., PI3Kγ and PI3Kδ).

In some embodiments, one or more of the crystalline forms is used in combination with another kinase inhibitor to inhibit the activity of one kinase (e.g., PI3Kγ or PI3Kδ).

In some embodiments, one or more of the crystalline forms is used in combination with another kinase inhibitor to inhibit the activities of more than one kinase (e.g., PI3Kγ or PI3Kδ), such as at least two kinases.

Another aspect of the present invention pertains to methods of treating a kinase (such as PI3K)-associated disease or disorder in an individual (e.g., patient) by administering to the individual in need of such treatment a therapeutically effective amount or dose of one or more crystalline forms of the present invention or a pharmaceutical composition thereof. A PI3K-associated disease can include any disease, disorder or condition that is directly or indirectly linked to expression or activity of the PI3K, including overexpression and/or abnormal activity levels. In some embodiments, the disease can be linked to Akt (protein kinase B), mammalian target of rapamycin (mTOR), or phosphoinositide-dependent kinase 1 (PDK1). In some embodiments, the mTOR-related disease can be inflammation, atherosclerosis, psoriasis, restenosis, benign prostatic hypertrophy, bone disorders, pancreatitis, angiogenesis, diabetic retinopathy, arthritis, immunological disorders, kidney disease, or cancer. A PI3K-associated disease can also include any disease, disorder or condition that can be prevented, ameliorated, or cured by modulating PI3K activity. In some embodiments, the disease is characterized by the abnormal activity of PI3K. In some embodiments, the disease is characterized by mutant PI3K. In such embodiments, the mutation can be present in the kinase domain of the PI3K.

Examples of PI3K-associated diseases include immune-based diseases involving the system including, for example, rheumatoid arthritis, allergy, asthma, glomerulonephritis, lupus, or inflammation related to any of the above.

Further examples of PI3K-associated diseases include cancers such as breast, prostate, colon, endometrial, brain, bladder, skin, uterus, ovary, lung, pancreatic, renal, gastric, or hematological cancer.

In some embodiments, the hematological cancer is acute myeloblastic leukemia (AML) or chronic myeloid leukemia (CML), or B cell lymphoma.

Further examples of PI3K-associated diseases include lung diseases such as acute lung injury (ALI) and adult respiratory distress syndrome (ARDS).

Further examples of PI3K-associated diseases include osteoarthritis, restenosis, atherosclerosis, bone disorders, arthritis, diabetic retinopathy, psoriasis, benign prostatic hypertrophy, inflammation, angiogenesis, pancreatitis, kidney disease, inflammatory bowel disease, myasthenia gravis, multiple sclerosis, or Sjoegren's syndrome, and the like.

Further examples of PI3K-associated diseases include idiopathic thrombocytopenic purpura (ITP), autoimmune hemolytic anemia (AIHA), vasculitis, systemic lupus erythematosus, lupus nephritis, pemphigus, membranous nephropathy, chronic lymphocytic leukemia (CLL), Non-Hodgkin lymphoma, hairy cell leukemia, Mantle cell lymphoma, Burkitt lymphoma, small lymphocytic lymphoma, follicular lymphoma, lymphoplasmacytic lymphoma, extranodal marginal zone lymphoma, activated B-cell like (ABC) diffuse large B cell lymphoma, or germinal center B cell (GCB) diffuse large B cell lymphoma.

In some embodiments, the present application provides a method of treating pemphigus, membranous nephropathy, Hodgkin's lymphoma, Waldenstrom's macroglobulinemia, prolymphocytic leukemia, acute lymphoblastic leukemia, myelofibrosis, mucosa-associated lymphatic tissue (MALT) lymphoma, mediastinal (thymic) large B-cell lymphoma, lymphomatoid granulomatosis, splenic marginal zone lymphoma, primary effusion lymphoma, intravascular large B-cell lymphoma, plasma cell leukemia, extramedullary plasmacytoma, smouldering myeloma (aka asymptomatic myeloma), or monoclonal gammopathy of undetermined significance (MGUS).

In some embodiments, the present application provides a method of treating osteoarthritis, restenosis, atherosclerosis, bone disorders, arthritis, diabetic retinopathy, psoriasis, benign prostatic hypertrophy, inflammation, angiogenesis, pancreatitis, kidney disease, inflammatory bowel disease, myasthenia gravis, multiple sclerosis, or Sjögren's syndrome.

In some embodiments, the disease is idiopathic thrombocytopenic purpura (ITP), autoimmune hemolytic anemia (AIHA), vasculitis, pemphigus, or membranous nephropathy.

In some embodiments, the idiopathic thrombocytopenic purpura (ITP) is selected from relapsed ITP and refractory ITP.

In some embodiments, the vasculitis is selected from Behçet's disease, Cogan's syndrome, giant cell arteritis, polymyalgia rheumatica (PMR), Takayasu's arteritis, Buerger's disease (thromboangiitis obliterans), central nervous system vasculitis, Kawasaki disease, polyarteritis nodosa, Churg-Strauss syndrome, mixed cryoglobulinemia vasculitis (essential or hepatitis C virus (HCV)-induced), Henoch-Schönlein purpura (HSP), hypersensitivity vasculitis, microscopic polyangiitis, Wegener's granulomatosis, and anti-neutrophil cytoplasm antibody associated (ANCA) systemic vasculitis (AASV).

In some embodiments, the present application provides methods of treating an immune-based disease, cancer, or lung disease in a patient.

In some embodiments, the immune-based disease is systemic lupus erythematosus or lupus nephritis.

In some embodiments, the cancer is breast cancer, prostate cancer, colon cancer, endometrial cancer, brain cancer, bladder cancer, skin cancer, cancer of the uterus, cancer of the ovary, lung cancer, pancreatic cancer, renal cancer, gastric cancer, or a hematological cancer.

In some embodiments, the hematological cancer is acute myeloblastic leukemia, chronic myeloid leukemia, B cell lymphoma, chronic lymphocytic leukemia (CLL), Non- Hodgkins lymphoma, hairy cell leukemia, Mantle cell lymphoma, Burkitt lymphoma, small lymphocytic lymphoma, follicular lymphoma, lymphoplasmacytic lymphoma, extranodal marginal zone lymphoma, activated B-cell like (ABC) diffuse large B cell lymphoma, or germinal center B cell (GCB) diffuse large B cell lymphoma.

In some embodiments, the non-Hodgkin lymphoma (NHL) is selected from relapsed NHL, refractory NHL, and recurrent follicular NHL.

In some embodiments, the lung disease is acute lung injury (ALI) or adult respiratory distress syndrome (ARDS).

As used herein, the term "contacting" refers to the bringing together of indicated moieties in an in vitro system or an in vivo system. For example, "contacting" a PI3K with a crystalline form of the invention includes the administration of a crystalline form of the present invention to an individual or patient, such as a human, having a PI3K, as well as, for example, introducing a crystalline form of the invention into a sample containing a cellular or purified preparation containing the PI3K.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active crystalline form or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder (i.e., arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapies One or more additional pharmaceutical agents such as, for example, chemotherapeutics, anti-inflammatory agents, steroids, immunosuppressants, as well as Bcr-Abl, Flt-3, EGFR, HER2, JAK (e.g., JAK1 or JAK2), c-MET, VEGFR, PDGFR, cKit, IGF-1R, RAF, FAK, Akt mTOR, PIM, and AKT (e.g., AKT1, AKT2, or AKT3) kinase inhibitors such as, for example, those described in WO 2006/056399, or other agents such as, therapeutic antibodies can be used in combination with the crystalline forms of the present invention for treatment of PI3K-associated diseases, disorders or conditions. The one or more additional pharmaceutical agents can be administered to a patient simultaneously or sequentially.

In some embodiments, the additional pharmaceutical agent is a JAK1 and/or JAK2 inhibitor. In some embodiments, the present application provides a method of treating a disease described herein (e.g., a B cell malignancy, such as diffuse B-cell lymphoma) in a patient comprising administering to the patient a compound described herein, or a pharmaceutically acceptable salt thereof, and a JAK1 and/or JAK2 inhibitor. The B cell malignancies can include those described herein and in U.S. Ser. No. 61/976,815, filed Apr. 8, 2014. In some embodiments, the inhibitor of JAK1 and/or JAK2 is 3-cyclopentyl-3-[4-(7H-pyrrolo[2,3-d]pyrimidin-4-yl)-1H-pyrazol-1-yl]propanenitrile. In some embodiments, the inhibitor of JAK1 and/or JAK2 is (3R)-3-cyclopentyl-3-[4-(7H-pyrrolo[2,3-d]pyrimidin-4-yl)-1H-pyrazol-1-yl]propanenitrile (ruxolitinib; also known as INCB018424). Ruxolitinib has an $IC_{50}$ of less than 10 nM at 1 mM ATP (Assay D) at JAK1 and JAK2. 3-Cyclopentyl-3-[4-(7H-pyrrolo[2,3-d]pyrimidin-4-yl)-1H-pyrazol-1-yl]propanenitrile and ruxolitinib can be made by the procedure described in U.S. Pat. No. 7,598,257 (Example 67), filed Dec. 12, 2006, which is incorporated herein by reference in its entirety. In some embodiments, the inhibitor of JAK1 and/or JAK2 is (3R)-3-cyclopentyl-3-[4-(7H-pyrrolo[2,3-d]pyrimidin-4-yl)-1H-pyrazol-1-yl]propanenitrile phosphoric acid salt.

In some embodiments, the inhibitor of JAK1 and/or JAK2 is a compound of Table A, or a pharmaceutically acceptable salt thereof. The compounds in Table A are selective JAK1 inhibitors (selective over JAK2, JAK3, and TYK2). The $IC_{50}$s obtained by the method of Assay D at 1 mM ATP are shown in Table A.

TABLE A

| # | Name/Reference | Structure | JAK1 $IC_{50}$ (nM) | JAK2/ JAK1 |
|---|---|---|---|---|
| 1 | ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile U.S. 2014/0121198, Example 20 | 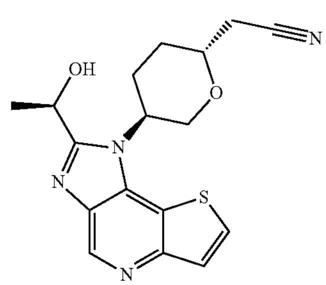 [SMILES: C[C@@H](O)c1nc2cnc3ccsc3c2n1[C@H]1CC[C@H](CC#N)OC1] | ++ | >10 |

TABLE A-continued

| # | Name/Reference | Structure | JAK1 IC$_{50}$ (nM) | JAK2/ JAK1 |
|---|---|---|---|---|
| 2 | 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide U.S. 2014/0343030, Example 7 | 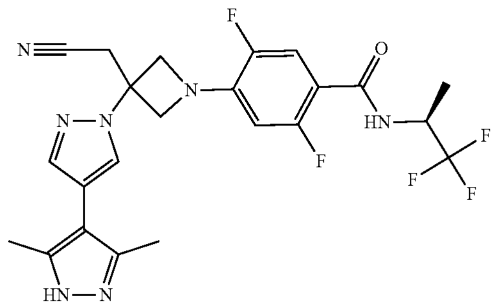 [SMILES: Cc1n[nH]c(C)c1-c1cnn(C2(CC#N)CN(c3cc(F)c(C(=O)N[C@@H](C)C(F)(F)F)cc3F)C2)c1] | +++ | >10 |
| 3 | 3-[1-(6-chloropyridin-2-yl)pyrrolidin-3-yl]-3-[4-(7H-pyrrolo[2,3-d]pyrimidin-4-yl)-1H-pyrazol-1-yl]propanenitrile U.S. 2010/0298334 Example 2$^a$ | 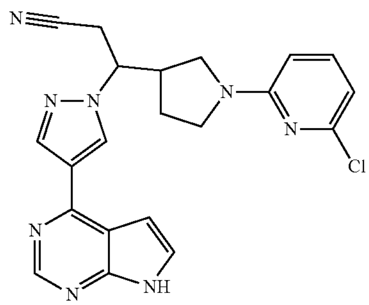 [SMILES: N#CCC(C1CCN(c2cccc(Cl)n2)C1)n1cc(-c2ncnc3[nH]ccc23)cn1] | + | >10 |
| 4 | 3-(1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile U.S. 2010/0298334 (Example 13c) | 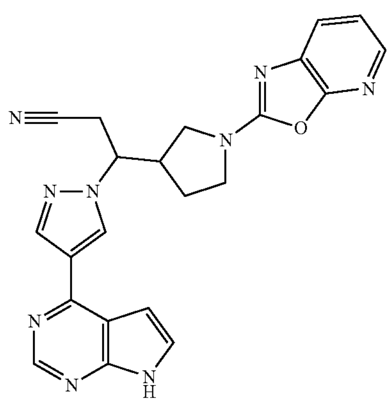 [SMILES: N#CCC(C1CCN(c2nc3cccnc3o2)C1)n1cc(-c2ncnc3[nH]ccc23)cn1] | + | >10 |
| 5 | 4-[(4-{3-cyano-2-[4-(7H-pyrrolo[2,3-d]pyrimidin-4-yl)-1H-pyrazol-1-yl]propyl}piperazin-1-yl)carbonyl]-3-fluorobenzonitrile U.S. 2011/0059951 (Example 12) | 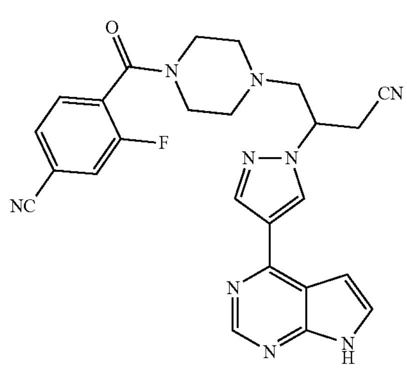 [SMILES: N#CCC(CN1CCN(C(=O)c2ccc(C#N)cc2F)CC1)n1cc(-c2ncnc3[nH]ccc23)cn1] | + | >10 |

TABLE A-continued

| # | Name/Reference | Structure | JAK1 IC$_{50}$ (nM) | JAK2/JAK1 |
|---|---|---|---|---|
| 6 | 4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile U.S. 2011/0059951 (Example 13) | 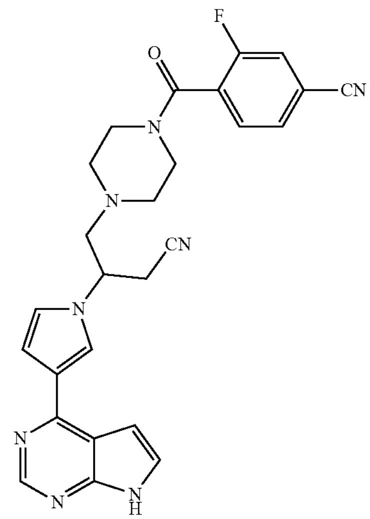 [SMILES: N#CCC(CN1CCN(C(=O)c2ccc(C#N)cc2F)CC1)n1ccc(-c2ncnc3[nH]ccc23)c1] | + | >10 |
| 7 | {1-{1-[3-Fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile U.S. 2011/0224190 (Example 1) | 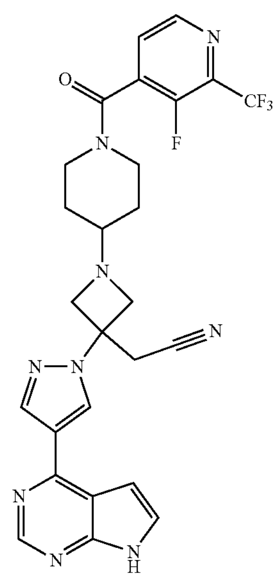 [SMILES: N#CCC1(n2cc(-c3ncnc4[nH]ccc34)cn2)CN(C2CCN(C(=O)c3ccnc(C(F)(F)F)c3F)CC2)C1] | + | >10 |

TABLE A-continued

| # | Name/Reference | Structure | JAK1 IC$_{50}$ (nM) | JAK2/ JAK1 |
|---|---|---|---|---|
| 8 | 4-{3-(Cyanomethyl)-3-[4-(7H-pyrrolo[2,3-d]pyrimidin-4-yl)-1H-pyrazol-1-yl]azetidin-1-yl}-N-[4-fluoro-2-(trifluoromethyl)phenyl]piperidine-1-carboxamide<br>U.S. 2011/0224190 (Example 154) | 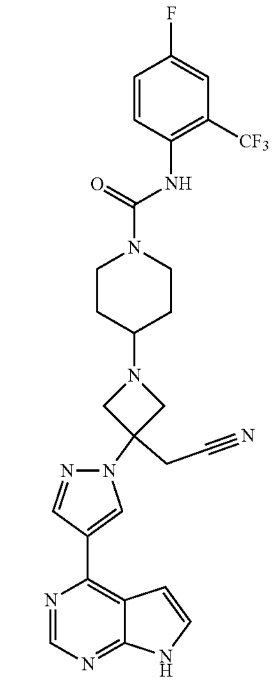 [SMILES: N#CCC1(n2cc(-c3ncnc4[nH]ccc34)cn2)CN(C2CCN(C(=O)Nc3ccc(F)cc3C(F)(F)F)CC2)C1] | + | >10 |
| 9 | [3-[4-(7H-pyrrolo[2,3-d]pyrimidin-4-yl)-1H-pyrazol-1-yl]-1-(1-{[2-(trifluoromethyl)pyrimidin-4-yl]carbonyl}piperidin-4-yl)azetidin-3-yl]acetonitrile<br>U.S. 2011/0224190 (Example 85) | 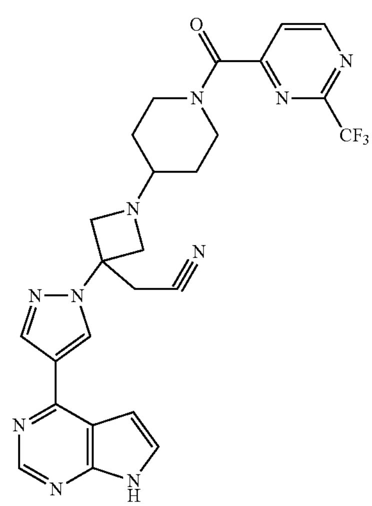 [SMILES: N#CCC1(n2cc(-c3ncnc4[nH]ccc34)cn2)CN(C2CCN(C(=O)c3ccnc(C(F)(F)F)n3)CC2)C1] | + | >10 |

TABLE A-continued

| # | Name/Reference | Structure | JAK1 IC$_{50}$ (nM) | JAK2/JAK1 |
|---|---|---|---|---|
| 10 | [trans-1-[4-(7H-pyrrolo[2,3-d]pyrimidin-4-yl)-1H-pyrazol-1-yl]-3-(4-{[2-(trifluoromethyl)pyrimidin-4-yl]carbonyl}piperazin-1-yl)cyclobutyl]acetonitrile<br>U.S. 2012/0149681 (Example 7b) | 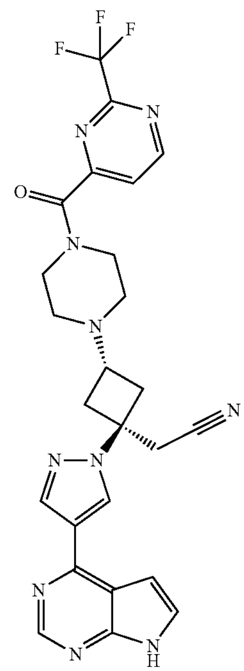 [SMILES: N#CC[C@]1(n2cc(-c3ncnc4[nH]ccc34)cn2)C[C@H](N2CCN(C(=O)c3ccnc(C(F)(F)F)n3)CC2)C1] | + | >10 |
| 11 | {trans-3-(4-{[4-[(3-hydroxyazetidin-1-yl)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile<br>U.S. 2012/0149681 (Example 157) | 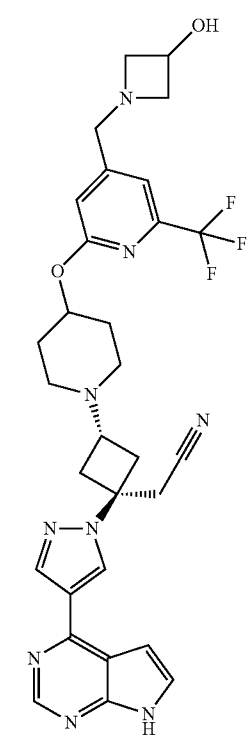 [SMILES: N#CC[C@]1(n2cc(-c3ncnc4[nH]ccc34)cn2)C[C@H](N2CCC(Oc3cc(CN4CC(O)C4)cc(C(F)(F)F)n3)CC2)C1] | + | >10 |

TABLE A-continued

| # | Name/Reference | Structure | JAK1 IC$_{50}$ (nM) | JAK2/JAK1 |
|---|---|---|---|---|
| 12 | {trans-3-(4-{[4-{[(2S)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile U.S. 2012/0149681 (Example 161) | 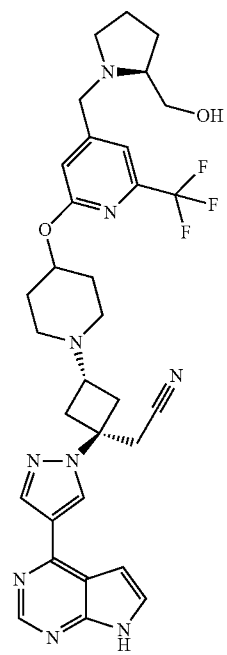 [SMILES: N#CC[C@]1(n2cc(-c3ncnc4[nH]ccc34)cn2)C[C@H](N2CCC(Oc3cc(CN4CCC[C@H]4CO)cc(C(F)(F)F)n3)CC2)C1] | + | >10 |
| 13 | {trans-3-(4-{[4-{[(2R)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile U.S. 2012/0149681 (Example 162) | 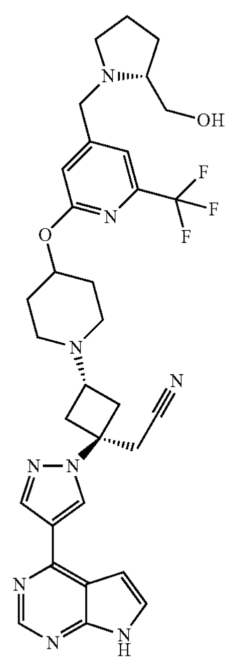 [SMILES: N#CC[C@]1(n2cc(-c3ncnc4[nH]ccc34)cn2)C[C@H](N2CCC(Oc3cc(CN4CCC[C@@H]4CO)cc(C(F)(F)F)n3)CC2)C1] | + | >10 |

TABLE A-continued

| # | Name/Reference | Structure | JAK1 IC$_{50}$ (nM) | JAK2/ JAK1 |
|---|---|---|---|---|
| 14 | 4-(4-{3-[(dimethylamino)methyl]-5-fluorophenoxy}piperidin-1-yl)-3-[4-(7H-pyrrolo[2,3-d]pyrimidin-4-yl)-1H-pyrazol-1-yl]butanenitrile U.S. 2012/0149682 (Example 20)[b] | 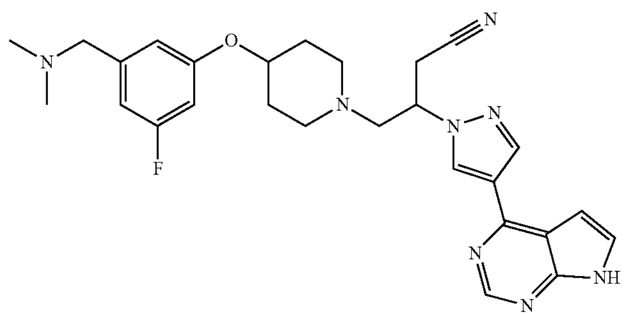 [SMILES: CN(C)Cc1cc(F)cc(OC2CCN(CC(CC#N)n3cc(-c4ncnc5[nH]ccc45)cn3)CC2)c1] | + | >10 |
| 15 | 5-{3-(cyanomethyl)-3-[4-(7H-pyrrolo[2,3-d]pyrimidin-4-yl)-1H-pyrazol-1-yl]azetidin-1-yl}-N-isopropylpyrazine-2-carboxamide U.S. 2013/0018034 (Example 18) | 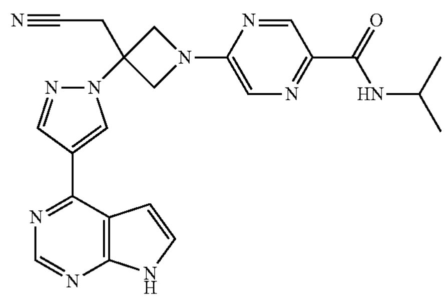 [SMILES: CC(C)NC(=O)c1cnc(N2CC(CC#N)(n3cc(-c4ncnc5[nH]ccc45)cn3)C2)cn1] | + | >10 |
| 16 | 4-{3-(cyanomethyl)-3-[4-(7H-pyrrolo[2,3-d]pyrimidin-4-yl)-1H-pyrazol-1-yl]azetidin-1-yl}-2,5-difluoro-N-[(1S)-2,2,2-trifluoro-1-methylethyl]benzamide U.S. 2013/0018034 (Example 28) | 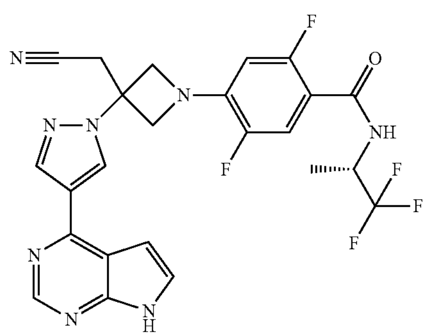 [SMILES: C[C@H](NC(=O)c1cc(F)c(N2CC(CC#N)(n3cc(-c4ncnc5[nH]ccc45)cn3)C2)cc1F)C(F)(F)F] | + | >10 |
| 17 | 5-{3-(cyanomethyl)-3-[4-(1H-pyrrolo[2,3-b]pyridin-4-yl)-1H-pyrazol-1-yl]azetidin-1-yl}-N-isopropylpyrazine-2-carboxamide U.S. 2013/0018034 (Example 34) | 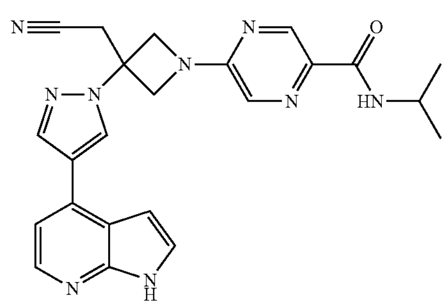 [SMILES: CC(C)NC(=O)c1cnc(N2CC(CC#N)(n3cc(-c4ccnc5[nH]ccc45)cn3)C2)cn1] | + | >10 |

TABLE A-continued

| # | Name/Reference | Structure | JAK1 IC$_{50}$ (nM) | JAK2/ JAK1 |
|---|---|---|---|---|
| 18 | {1-(cis-4-{[6-(2-hydroxyethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile U.S. 2013/0045963 (Example 45) | 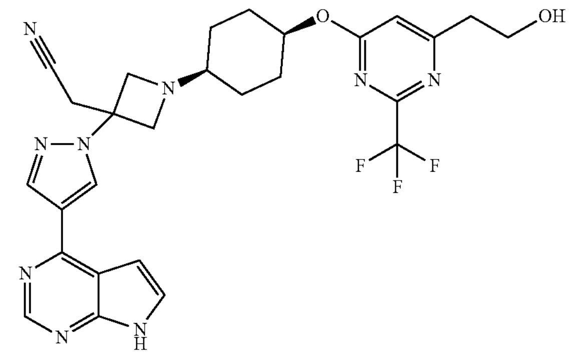 [SMILES: N#CCC1(n2cc(-c3ncnc4[nH]ccc34)cn2)CN([C@H]2CC[C@@H](Oc3cc(CCO)nc(C(F)(F)F)n3)CC2)C1] | + | >10 |
| 19 | {1-(cis-4-{[4-[(ethylamino)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile U.S. 2013/0045963 (Example 65) | 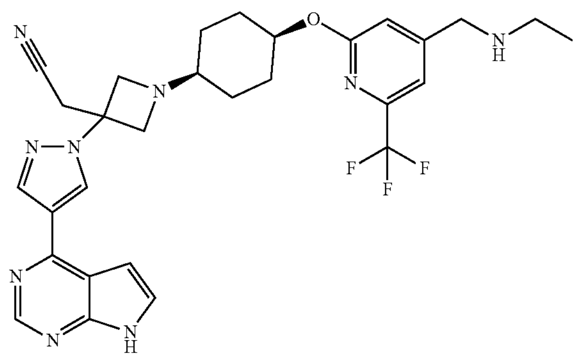 [SMILES: CCNCc1cc(O[C@H]2CC[C@@H](N3CC(CC#N)(n4cc(-c5ncnc6[nH]ccc56)cn4)C3)CC2)nc(C(F)(F)F)c1] | + | >10 |
| 20 | {1-(cis-4-{[4-(1-hydroxy-1-methylethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile U.S. 2013/0045963 (Example 69) | 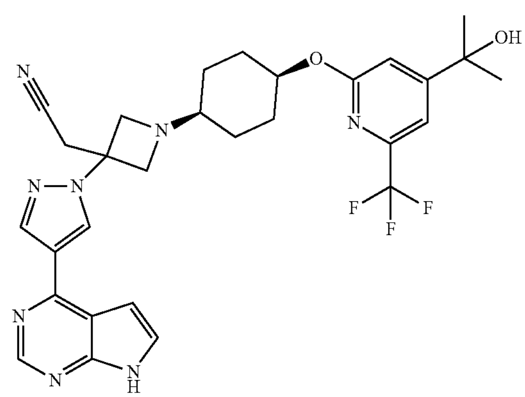 [SMILES: CC(C)(O)c1cc(O[C@H]2CC[C@@H](N3CC(CC#N)(n4cc(-c5ncnc6[nH]ccc56)cn4)C3)CC2)nc(C(F)(F)F)c1] | + | >10 |
| 21 | {1-(cis-4-{[4-{[(3R)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile U.S. 2013/0045963 (Example 95) | 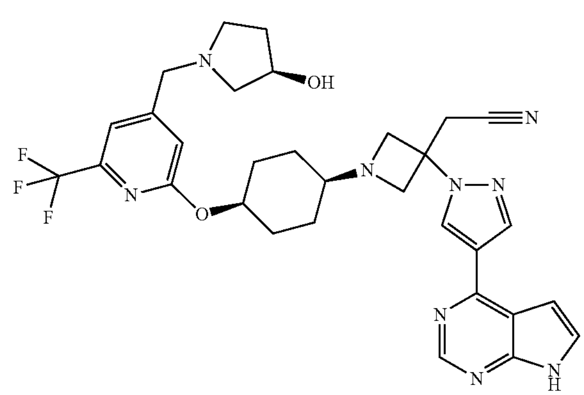 [SMILES: N#CCC1(n2cc(-c3ncnc4[nH]ccc34)cn2)CN([C@H]2CC[C@@H](Oc3cc(CN4CC[C@@H](O)C4)cc(C(F)(F)F)n3)CC2)C1] | + | >10 |

TABLE A-continued

| # | Name/Reference | Structure | JAK1 IC$_{50}$ (nM) | JAK2/ JAK1 |
|---|---|---|---|---|
| 22 | {1-(cis-4-{[4-{[(3S)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile U.S. 2013/0045963 (Example 95) | 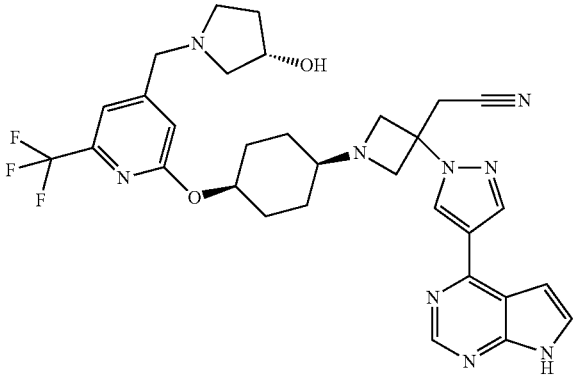 [SMILES: N#CCC1(n2cc(-c3ncnc4[nH]ccc34)cn2)CN([C@H]2CC[C@@H](Oc3cc(CN4CC[C@H](O)C4)cc(C(F)(F)F)n3)CC2)C1] | + | >10 |
| 23 | {trans-3-(4-{[4-({[(1S)-2-hydroxy-1-methylethyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile U.S. 2014/0005166 (Example 1) | 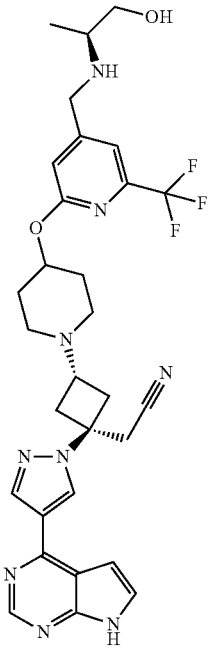 [SMILES: C[C@@H](CO)NCc1cc(OC2CCN([C@H]3C[C@](CC#N)(n4cc(-c5ncnc6[nH]ccc56)cn4)C3)CC2)nc(C(F)(F)F)c1] | + | >10 |

TABLE A-continued

| # | Name/Reference | Structure | JAK1 IC$_{50}$ (nM) | JAK2/ JAK1 |
|---|---|---|---|---|
| 24 | {trans-3-(4-{[4-({[(2R)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile U.S. 2014/0005166 (Example 14) | 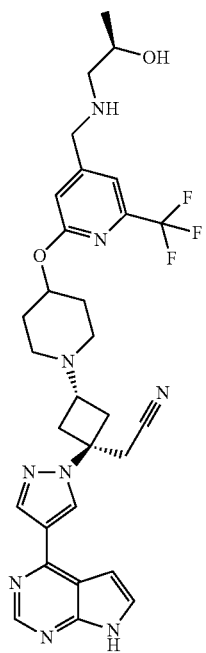 [SMILES: C[C@@H](O)CNCc1cc(OC2CCN([C@H]3C[C@](CC#N)(n4cc(-c5ncnc6[nH]ccc56)cn4)C3)CC2)nc(C(F)(F)F)c1] | + | >10 |
| 25 | {trans-3-(4-([4-({[(2S)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile U.S. 2014/0005166 (Example 15) | 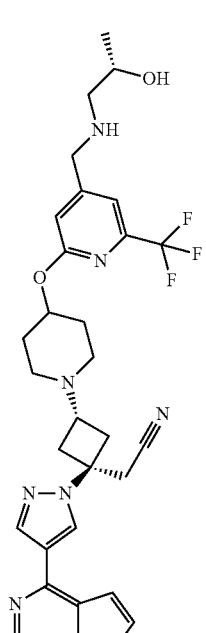 | + | >10 |

TABLE A-continued

| # | Name/Reference | Structure | JAK1 IC$_{50}$ (nM) | JAK2/ JAK1 |
|---|---|---|---|---|
| 26 | {trans-3-(4-{[4-(2-hydroxyethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile U.S. 2014/0005166 (Example 20) | 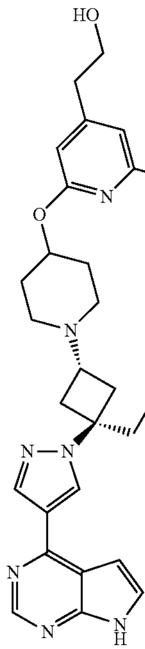 | + | >10 |

+ means <10 nM (see Example D for assay conditions)
++ means ≤100 nM (see Example D for assay conditions)
+++ means ≤300 nM (see Example D for assay conditions)
$^a$Data for enantiomer 1
$^b$Data for enantiomer 2

In some embodiments, the inhibitor of JAK1 and/or JAK2 is {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof.

In some embodiments, the inhibitor of JAK1 and/or JAK2 is {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile adipic acid salt.

In some embodiments, the inhibitor of JAK1 and/or JAK2 is 4-{3-(cyanomethyl)-3-[4-(7H-pyrrolo[2,3-d]pyrimidin-4-yl)-1H-pyrazol-1-yl]azetidin-1-yl}-2,5-difluoro-N-[(1S)-2,2,2-trifluoro-1-methylethyl]benzamide, or a pharmaceutically acceptable salt thereof.

In some embodiments, the inhibitor of JAK1 and/or JAK2 is selected from (R)-3-[1-(6-chloropyridin-2-yl)pyrrolidin-3-yl]-3-[4-(7H-pyrrolo[2,3-d]pyrimidin-4-yl)-1H-pyrazol-1-yl]propanenitrile, (R)-3-(1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile, (R)-4-[(4-{3-cyano-2-[4-(7H-pyrrolo[2,3-d]pyrimidin-4-yl)-1H-pyrazol-1-yl]propyl}piperazin-1-yl)carbonyl]-3-fluorobenzonitrile, (R)-4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile, or (R)-4-(4-{3-[(dimethylamino)methyl]-5-fluorophenoxy}piperidin-1-yl)-3-[4-(7H-pyrrolo[2,3-d]pyrimidin-4-yl)-1H-pyrazol-1-yl]butanenitrile, (S)-3-[1-(6-chloropyridin-2-yl)pyrrolidin-3-yl]-3-[4-(7H-pyrrolo[2,3-d]pyrimidin-4-yl)-1H-pyrazol-1-yl]propanenitrile, (S)-3-(1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile, (S)-4-[(4-{3-cyano-2-[4-(7H-pyrrolo[2,3-d]pyrimidin-4-yl)-1H-pyrazol-1-yl]propyl}piperazin-1-yl)carbonyl]-3-fluorobenzonitrile, (S)-4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile, (S)-4-(4-{3-[(dimethylamino)methyl]-5-fluorophenoxy}piperidin-1-yl)-3-[4-(7H-pyrrolo[2,3-d]pyrimidin-4-yl)-1H-pyrazol-1-yl]butanenitrile; and pharmaceutically acceptable salts of any of the aforementioned.

In some embodiments, the compounds of Table A are prepared by the synthetic procedures described in US Patent Publ. No. 2010/0298334, filed May 21, 2010, US Patent Publ. No. 2011/0059951, filed Aug. 31, 2010, US Patent Publ. No. 2011/0224190, filed Mar. 9, 2011, US Patent Publ. No. 2012/0149681, filed Nov. 18, 2011, US Patent Publ. No. 2012/0149682, filed Nov. 18, 2011, US Patent Publ. 2013/0018034, filed Jun. 19, 2012, US Patent Publ. No. 2013/0045963, filed Aug. 17, 2012, and US Patent Publ. No. 2014/0005166, filed May 17, 2013, each of which is incorporated herein by reference in its entirety.

In some embodiments, the inhibitor of JAK1 and/or JAK2 is selected from the compounds of US Patent Publ. No. 2010/0298334, filed May 21, 2010, US Patent Publ. No. 2011/0059951, filed Aug. 31, 2010, US Patent Publ. No. 2011/0224190, filed Mar. 9, 2011, US Patent Publ. No. 2012/0149681, filed Nov. 18, 2011, US Patent Publ. No. 2012/0149682, filed Nov. 18, 2011, US Patent Publ. 2013/0018034, filed Jun. 19, 2012, US Patent Publ. No. 2013/0045963, filed Aug. 17, 2012, and US Patent Publ. No. 2014/0005166, filed May 17, 2013, each of which is incorporated herein by reference in its entirety.

Example antibodies for use in combination therapy include but are not limited to Trastuzumab (e.g. anti-HER2), Ranibizumab (e.g. anti-VEGF-A), Bevacizumab (trade name Avastin, e.g. anti-VEGF, Panitumumab (e.g. anti-EGFR), Cetuximab (e.g. anti-EGFR), Rituxan (anti-CD20) and antibodies directed to c-MET.

One or more of the following agents may be used in combination with the crystalline forms of the present invention and are presented as a non limiting list: a cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, temozolomide, cyclophosphamide, SCH 66336, R115777, L778,123, BMS 214662, Iressa, Tarceva, antibodies to EGFR, Gleevec™, intron, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, ELOXATIN™, Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17.alpha.-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Fulvestrant, Ifosfomide, Rituximab, C225, Campath, Clofarabine, cladribine, aphidicolon, rituxan, sunitinib, dasatinib, tezacitabine, Sml1, fludarabine, pentostatin, triapine, didox, trimidox, amidox, 3-AP, MDL-101,731, bendamustine (Treanda), ofatumumab, and GS-1101 (also known as CAL-101).

Example chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include corticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include compounds, and their pharmaceutically acceptable salts, as disclosed in WO 03/037347, WO 03/099771, and WO 04/046120.

Example suitable RAF inhibitors include compounds, and their pharmaceutically acceptable salts, as disclosed in WO 00/09495 and WO 05/028444.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402.

Example suitable mTOR inhibitors include compounds, and their pharmaceutically acceptable salts, as disclosed in WO 2011/025889.

In some embodiments, the crystalline forms of the invention can be used in combination with one or more other kinase inhibitors including imatinib, particularly for treating patients resistant to imatinib or other kinase inhibitors.

In some embodiments, the crystalline forms of the invention can be used in combination with a chemotherapeutic in the treatment of cancer, such as multiple myeloma, and may improve the treatment response as compared to the response to the chemotherapeutic agent alone, without exacerbation of its toxic effects. Examples of additional pharmaceutical agents used in the treatment of multiple myeloma, for example, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. Additive or synergistic effects are desirable outcomes of combining a PI3K inhibitor of the present invention with an additional agent. Furthermore, resistance of multiple myeloma cells to agents such as dexamethasone may be reversible upon treatment with the PI3K inhibitor of the present invention. The agents can be combined with the present crystalline form in a single or continuous dosage form, or the agents can be administered simultaneously or sequentially as separate dosage forms.

In some embodiments, a corticosteroid such as dexamethasone is administered to a patient in combination with the crystalline forms of the invention where the dexamethasone is administered intermittently as opposed to continuously.

In some further embodiments, combinations of the crystalline forms of the invention with other therapeutic agents can be administered to a patient prior to, during, and/or after a bone marrow transplant or stem cell transplant.

Pharmaceutical Formulations and Dosage Forms

When employed as pharmaceuticals, the crystalline forms of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the crystalline form of the invention in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active crystalline form, soft and hard gelatin capsules, suppositories, sterile injectable solutions, and sterile packaged powders.

In preparing a formulation, the active crystalline form can be milled to provide the appropriate particle size prior to combining with the other ingredients. If the active crystalline form is substantially insoluble, it can be milled to a particle size of less than 200 mesh. If the active crystalline form is substantially water soluble, the particle size can be adjusted by milling to provide a substantially uniform distribution in the formulation, e.g. about 40 mesh.

The crystalline forms of the invention may be milled using known milling procedures such as wet milling to obtain a particle size appropriate for tablet formation and for other formulation types. Finely divided (nanoparticulate) preparations of the crystalline forms of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the crystalline forms or compositions of the invention contain from about 5 to about 50 mg of the active ingredient. One having ordinary skill in the art will appreciate that this embodies crystalline forms or compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the crystalline forms or compositions of the invention contain from about 50 to about 500 mg of the active ingredient. One having ordinary skill in the art will appreciate that this embodies crystalline forms or compositions containing about 50 to about 100, about 100 to about 150, about 150 to about 200, about 200 to about 250, about 250 to about 300, about 350 to about 400, or about 450 to about 500 mg of the active ingredient.

In some embodiments, the crystalline forms or compositions of the invention contain from about 500 to about 1000 mg of the active ingredient. One having ordinary skill in the art will appreciate that this embodies crystalline forms or compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the crystalline forms described herein in the methods and uses of the invention.

The active crystalline form can be effective over a wide dosage range and is generally administered in a pharmaceutically effective amount. It will be understood, however, that the amount of the crystalline form actually administered will usually be determined by a physician, according to the relevant circumstances, including the condition to be treated, the chosen route of administration, the actual crystalline form administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a crystalline form of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the crystalline forms and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the crystalline form of the invention. The topical formulations can be suitably packaged in tubes of, for example, 100 g which are optionally associated with instructions for the treatment of the select indication, e.g., psoriasis or other skin condition.

The amount of crystalline form or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the crystalline form preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a crystalline form of the present application can vary according to, for example, the particular use for which the treatment is made, the manner of administration of the crystalline form, the health and condition of the patient, and the judgment of the prescribing physician. The proportion or concentration of a crystalline form of the invention in a pharmaceutical composition can vary depending upon a number of factors including dosage, chemical characteristics (e.g., hydrophobicity), and the route of administration. For example, the crystalline forms of the invention can be provided in an aqueous physiological buffer solution containing about 0.1 to about 10% w/v of the crystalline form for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the crystalline form selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

Labeled Compounds and Assay Methods

Another aspect of the present invention relates to labeled crystalline forms of the invention (radio-labeled, fluorescent-labeled, etc.) that would be useful not only in imaging techniques but also in assays, both in vitro and in vivo, for localizing and quantitating PI3K in tissue samples, including human, and for identifying PI3K ligands by inhibition binding of a labeled compound. Accordingly, the present invention includes PI3K assays that contain such labeled compounds.

The present invention further includes isotopically-labeled crystalline forms of the invention. An "isotopically" or "radio-labeled" crystalline form is a crystalline form of the invention where one or more atoms are replaced or substituted by an atom having an atomic mass or mass number different from the atomic mass or mass number typically found in nature (i.e., naturally occurring). Suitable radionuclides that may be incorporated in crystalline forms of the present invention include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled crystalline form will depend on the specific application of that radio-labeled crystalline form. For example, for in vitro PI3K labeling and competition assays, crystalline forms that incorporate $^3$H, $^{14}$C, $^{82}$Br, $^{125}$I, $^{135}$S, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled" or "labeled compound" is a crystalline form that has incorporated at least one radionuclide. In some embodiments the radionuclide is selected from the group consisting of $^3$H, $^{14}$C, $^{125}$I, $^{35}$S and $^{82}$Br. In some embodiments, one or more H atoms for any crystalline form described herein is each replaced by a deuterium atom.

The present invention can further include synthetic methods for incorporating radio-isotopes into crystalline forms of the invention. Synthetic methods for incorporating radio-isotopes into organic compounds are well known in the art, and an ordinary skill in the art will readily recognize the methods applicable for the crystalline forms of invention.

A labeled crystalline form of the invention can be used in a screening assay to identify/evaluate compounds. For example, a newly synthesized or identified compound (i.e., test compound) which is labeled can be evaluated for its ability to bind a PI3K by monitoring its concentration variation when contacting with the PI3K, through tracking of the labeling. For example, a test compound (labeled) can be evaluated for its ability to reduce binding of another compound which is known to bind to a PI3K (i.e., standard compound). Accordingly, the ability of a test compound to compete with the standard compound for binding to the PI3K directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of PI3K-associated diseases or disorders, such as cancer, which include one or more containers containing a pharmaceutical composition comprising a therapeutically effective amount of a crystalline form of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

EXAMPLES

In the below examples, X-Ray Powder Diffraction analysis was carried out on a Rigaku MiniFlex X-ray Powder Diffractometer (XRPD) instrument with the following parameters: radiation source is Cu at 1.054056 Å with $K_\beta$ filter and X-ray power of 30 KV, 15 mA. The sample powder was dispersed on a zero-background sample holder. General measurement conditions were:
Start Angle—3°
Stop Angle—45°
Sampling—0.02 deg.
Scan speed—2 deg/min.

Differential Scanning calorimetry (DSC) was carried out on a TA Instrument Differential Scanning calorimetry, Model Q20 with autosampler. The general experimental conditions were: 30-260° C. at 10° C./min, nitrogen gas flow at 50 mL/min, using an aluminum sample pan.

Thermogravimetric analysis (TGA) was carried out on a TA Instrument Thermogravimetric Analyzer, Model Q500 with the following conditions: Ramp at 20° C./min. to 600° C.; nitrogen gas at 40 mL/min balance purge flow; 60 mL/min sample purge flow; and platinum sample pan.

Dynamic Vapor Sorption (DVS) was performed in an SGA-100 Symmetric Vapor Sorption Analyzer from VTI Corporation. The moisture uptake profile was completed in three cycles in 10% RH increments with the first adsorption from 25% to 95% RH, followed by desorption in 10% increments from 95% to 5% RH. The equilibration criteria were 0.0050 wt % in 5 minutes with a maximum equilibration time of 180 minutes. All adsorption and desorption were performed at room temperature (25° C.). No pre-drying step was applied for the sample.

Example 1

Preparation and Characterization of Form I

A solution of concentrated HCl (141 mL, 1.69 mol, 1.2 eq.) in 2-propanol (1.51 L) was added to a solution of (S)-7-(1-((9H-purin-6-yl)amino)ethyl)-6-(3-fluorophenyl)-3-methyl-5H-thiazolo[3,2-a]pyrimidin-5-one (648 g, 92 wt %, 1.41 mol, 1.0 eq., see US Pat. Pub. No. 2011/0015212) in 2-propanol (7.1 L) under a nitrogen atmosphere in a reactor. The reaction mixture was stirred at room temperature for about 25 minutes, then stirred at 79° C. for about 1.5 hours, and then stirred at room temperature for about 1 hour. The product was filtered, washed with 2-propanol (3×0.55 L), washed with heptanes (3×0.55 L), and dried under reduced pressure to afford (S)-7-(1-((9H-purin-6-yl)amino)ethyl)-6-(3-fluorophenyl)-3-methyl-5H-thiazolo[3,2-a]pyrimidin-5-one hydrochloride (550 g, 85% yield).

(S)-7-(1-(9H-purin-6-ylamino)ethyl)-6-(3-fluorophenyl)-3-methyl-5H-thiazolo[3,2-a]pyrimidin-5-one hydrochloride (325 g) and $CH_2Cl_2$ (3.5 L) were charged to a reactor under nitrogen. Aqueous $Na_2CO_3$ was charged until the pH was 12, and the reaction mixture was stirred for 40 minutes. The reaction mixture was filtered and the phases were separated. The aqueous phase and $CH_2Cl_2$ (2.0 L) and conc. HCl (20 mL) were charged to a reactor and stirred for 10 minutes until the pH was 2. Saturated aqueous $K_2CO_3$ (300 mL) was charged until the pH was 12. The phases were separated, and the aqueous phase was extracted with $CH_2Cl_2$ (500 mL). The phases were separated, and the organic phase was washed with brine (1000 mL) and dried over $MgSO_4$. The reaction mixture was filtered and the filter cake was washed with $CH_2Cl_2$ (2×300 mL). The combined organic phases were distilled under reduced pressure. Ethyl acetate (2.5 L) was charged to the reactor and the distillation was continued at atmospheric pressure until the temperature reached 68° C. The distillation was stopped, and the distillation residue was cooled to 62° C. A 3:2 (v/v) mixture of $MeOH/CH_2Cl_2$ (500 mL) was added and the reaction mixture was cooled to room temperature. The reaction mixture was filtered, and the filter cake was washed with chilled EtOAc (3×300 mL) and heptanes (3×300 mL) and dried under reduced pressure at 45-50° C. to afford (S)-7-(1-(9H-purin-6-ylamino)ethyl)-6-(3-fluorophenyl)-3-methyl-5H-thiazolo[3,2-a]pyrimidin-5-one (Form I).

Form I was confirmed as a crystalline solid according to XRPD analysis. The XRPD pattern of Form I is shown in FIG. 1 and the peak data is given below in Table 1.

TABLE 1

| XRPD Peak Data for Form I. | | |
|---|---|---|
| 2-Theta | Height | H% |
| 9.2 | 85 | 7.6 |
| 10.0 | 1108 | 100 |
| 11.7 | 308 | 27.8 |
| 12.6 | 924 | 83.3 |
| 15.1 | 369 | 33.3 |
| 15.6 | 440 | 39.7 |
| 16.3 | 285 | 25.7 |
| 16.7 | 100 | 9 |
| 18.0 | 745 | 67.2 |
| 19.1 | 72 | 6.5 |
| 19.9 | 319 | 28.8 |
| 20.3 | 372 | 33.6 |
| 21.2 | 467 | 42.1 |
| 22.6 | 857 | 77.3 |
| 22.9 | 300 | 27.1 |
| 24.0 | 599 | 54.1 |
| 25.5 | 152 | 13.7 |
| 25.9 | 374 | 33.7 |
| 26.8 | 228 | 20.6 |
| 27.6 | 157 | 14.2 |
| 28.0 | 420 | 37.9 |
| 29.0 | 319 | 28.8 |
| 30.0 | 376 | 33.9 |
| 32.9 | 111 | 10 |
| 33.7 | 118 | 10.7 |
| 34.7 | 99 | 8.9 |

DSC analysis of Form I revealed one peak with an onset temperature of 176° C. and a maximum at 183° C. The DSC thermogram is provided in FIG. 2.

TGA analysis of Form I revealed 0.2% weight loss up to 100° C. The TGA thermogram is provided in FIG. 3.

Moisture adsorption/desorption of Form I was analyzed by DVS. Results from two DVS cycles are shown in FIG. 4. The data indicate that Form I initially contained about 0.3% water, and water adsorption increased to 1.8% at 85% RH. The shapes of the isotherms indicate weak adsorbent-adsorbate interaction and a low moisture uptake at low vapor concentration. Additionally, the data indicate a strong increase in sorption at higher vapor concentration, with maximum adsorption at about 85% RH.

Example 2

Crystalline Form Screening Methods and Results

New crystalline forms of the compound of Formula I were obtained from the various screening methods described below. Form I, as described above in Example 1, was used as the starting material in the screens unless otherwise indicated.

Phase Equilibrium Screen at 25 and 50° C.

The compound of Formula I (from Example 1) was equilibrated in various solvents at 25+/−1° C. and 50+/−1° C. To 2 mL of saturated or cloudy solutions of the compound of Formula I prepared in various solvents, as listed below in Tables 2 and 3, was added about 30 mg of additional compound of Formula I followed by stirring at 25±1° C. and at 50±1° C. The temperature was controlled by a IKA® ETS-D5 temperature controller and a IKA® RCT basic safety control.

The supernatant was filtered and the excess solid phase was analyzed via XRPD to determine crystallinity and the identity of any new crystalline forms. Results of the screens are indicated below in Tables 2 and 3. The entry "N/A" means that either the sample contained only clear solution or the amount of solid was too small to be analyzed by XRPD.

TABLE 2

Phase Equilibrium Results at 25° C.

| Solvent | Form |
| --- | --- |
| Acetonitrile | Form I |
| Chloroform | N/A |
| Methylene chloride | N/A |
| Dimethyl formamide | N/A |
| 1,4-Dioxane | Form VII |
| Methanol | N/A |
| 2-Methoxyethanol | N/A |
| Methyl isobutyl ketone | Form IX |
| Toluene | Form IV |
| Hexane | Form I |
| Tetrahydrofuran | N/A |
| Acetone | Form I |
| n-Butyl alcohol | N/A |
| Methyl t-butyl ether | Amorphous |
| Dimethyl sulfoxide | N/A |
| Ethanol | N/A |
| Ethyl acetate | Form I |
| Ethyl formate | Form I |
| Heptane | Form I |
| Isobutyl acetate | Form V |
| Isopropyl acetate | Form III |
| 1-Propanol | N/A |
| Isopropyl alcohol | N/A |
| Water | Form VII |
| Methyl ethyl ketone | Form I |

TABLE 3

Phase Equilibrium Results at 50° C.

| Solvent | Form |
| --- | --- |
| Acetonitrile | Form I |
| Chloroform | N/A |

TABLE 3-continued

Phase Equilibrium Results at 50° C.

| Solvent | Form |
| --- | --- |
| Methylene chloride | N/A |
| Dimethyl formamide | N/A |
| 1,4-Dioxane | N/A |
| Methanol | N/A |
| 2-Methoxyethanol | N/A |
| Methyl isobutyl ketone | Form IX |
| Toluene | Form IV |
| Hexane | Form I |
| Tetrahydrofuran | N/A |
| Acetone | Form X |
| n-Butyl alcohol | N/A |
| Methyl t-butyl ether | Form XII |
| Dimethyl sulfoxide | N/A |
| Ethanol | N/A |
| Ethyl acetate | Form I |
| Ethyl formate | Form I |
| Heptane | Form I |
| Isobutyl acetate | Form X |
| Isopropyl acetate | Form III |
| 1-Propanol | N/A |
| Isopropyl alcohol | Form II |
| Water | Form VI (hemihydrate) |
| Methyl ethyl ketone | Form I |

Evaporation Screen at 25 and 50° C.

Evaporation studies were carried out to identify the predominant crystal form during uncontrolled precipitation. The compound of Formula I (from Example 1) was dissolved in a solvent and then the resulting solution was subject to evaporation. Specifically, approximately 2 mL of saturated solution of the compound of Formula I in various solvents (see Tables 4 and 5 below) were evaporated under air without stirring at 25±1° C. and at 50±1° C. controlled by a IKA® ETS-D5 temperature controller and a IKA® RCT basic safety control. Experiments not resulting in any particulate solids were not studied. XRPD was used to identify the crystalline forms obtained. Results of the screens are indicated below in Tables 4 and 5. The entry "N/A" means that either the sample contained only clear solution or the amount of solid was too small to be analyzed by XRPD.

TABLE 4

Evaporation Results at 25° C.

| Solvent | Form |
| --- | --- |
| Acetonitrile | Form I |
| Chloroform | Oil |
| Methylene chloride | Form I |
| Dimethyl formamide | N/A |
| 1,4-Dioxane | Amorphous + solid |
| Methanol | Amorphous + solid |
| 2-Methoxyethanol | N/A |
| Methyl isobutyl ketone | Form IX |
| Toluene | N/A |
| Hexane | N/A |
| Tetrahydrofuran | Oil |
| Acetone | Form I |
| n-Butyl alcohol | N/A |
| Methyl t-butyl ether | N/A |
| Dimethyl sulfoxide | N/A |
| Ethanol | Form XIII |
| Ethyl acetate | N/A |
| Ethyl formate | Amorphous |
| Heptane | N/A |
| Isobutyl acetate | N/A |
| Isopropyl acetate | Form III |
| 1-Propanol | Form II |

TABLE 4-continued

Evaporation Results at 25° C.

| Solvent | Form |
|---|---|
| Isopropyl alcohol | Form VI |
| Water | N/A |
| Methyl ethyl ketone | N/A |

TABLE 5

Evaporation Results at 50° C.

| Solvent | Form |
|---|---|
| Acetonitrile | Amorphous |
| Chloroform | Amorphous |
| Methylene chloride | N/A |
| Dimethyl formamide | Amorphous |
| 1,4-Dioxane | N/A |
| Methanol | Amorphous |
| 2-Methoxyethanol | Form XIII |
| Methyl isobutyl ketone | N/A |
| Toluene | Form IV |
| Hexane | N/A |
| Tetrahydrofuran | Amorphous + solid |
| Acetone | Form X |
| n-Butyl alcohol | Form VIII |
| Methyl t-butyl ether | N/A |
| Dimethyl sulfoxide | N/A |
| Ethanol | Amorphous + solid |
| Ethyl acetate | N/A |
| Ethyl formate | Amorphous |
| Heptane | N/A |
| Isobutyl acetate | N/A |
| Isopropyl acetate | Form III |
| 1-Propanol | Amorphous |
| Isopropyl alcohol | Form II |
| Water | N/A |
| Methyl ethyl ketone | Amorphous |

Antisolvent Addition Screen

Saturated solutions of the compound of Formula I (from Example 1) were prepared by adding the compound to a solvent at room temperature until no more solids were dissolved. An antisolvent was added to induce precipitation. Specifically, the antisolvent was added dropwise at 1-6 times volume of solvent. Experiments that did not produce any particulate solids were not studied further. The results are presented in Table 6 below. The entry "N/A" means that either the sample contained only clear solution or the amount of solid was too small to be analyzed by XRPD.

TABLE 6

Antisolvent Addition Results

| Solvent (mL) | Antisolvent (mL) | Form |
|---|---|---|
| Acetonitrile (1.0) | Water (1.5) | N/A |
| Chloroform (0.5) | Heptane (2.5) | amorphous |
| Chloroform (0.5) | Hexane (2.5) | amorphous |
| Chloroform (0.5) | Methyl t-butyl ether (3.0) | amorphous |
| Dimethyl formamide (0.4) | Water (1.5) | N/A |
| Methanol (1.0) | Water (3.5) | N/A |
| 2-Methoxyethanol | Water | N/A |
| Tetrahydrofuran (1.0) | Heptane (3.0) | amorphous |
| Tetrahydrofuran (1.0) | Hexane (2.5) | Form XI |
| Tetrahydrofuran (1.0) | Methyl t-butyl ether (3.0) | N/A |
| Tetrahydrofuran (1.0) | Water (2.5) | Form VI |
| Dimethyl sulfoxide | Water | N/A |
| Ethanol (0.6) | Heptane (3.0) | Form II + amorphous |
| Ethanol (0.6) | Hexane (3.0) | N/A |
| Ethanol (0.5) | Methyl t-butyl ether (2.5) | N/A |
| Ethanol (0.5) | Water (1.0) | N/A |
| Isopropyl alcohol (0.5) | Heptane (2.5) | Form II |
| Isopropyl alcohol (0.5) | Hexane (2.5) | Form II |
| Isopropyl alcohol (0.5) | Methyl t-butyl ether (3.0) | N/A |
| Isopropyl alcohol (0.5) | Water (2.0) | N/A |

Reverse Addition Screen

Saturated or near saturated solutions (0.5-1 mL) of the compound of Formula I (from Example I) in various solvents were added to a larger volume of antisolvent. In most cases, no precipitate was obtained. Results are shown in Table 8 below. The entry "N/A" means that either the sample contained only clear solution or the amount of solid was too small to be analyzed by XRPD.

TABLE 8

Reverse Addition Results.

| Solvent | Antisolvent | Form |
|---|---|---|
| Chloroform | Heptane | amorphous |
| Chloroform | Hexane | amorphous |
| Chloroform | Methyl t-butyl ether | amorphous |
| 1,4-Dioxane | Heptane | N/A |
| 1,4-Dioxane | Hexane | N/A |
| 1,4-Dioxane | Methyl t-butyl ether | N/A |
| Dimethyl formamide | Water | Form VI |
| Methanol | Water | N/A |
| 2-Methoxyethanol | Water | N/A |
| Tetrahydrofuran | Heptane | Form VI |
| Tetrahydrofuran | Hexane | amorphous |
| Tetrahydrofuran | Methyl t-butyl ether | N/A |
| Tetrahydrofuran | Water | Form VI |
| Dimethyl sulfoxide | Water | N/A |
| Ethanol | Heptane | N/A |
| Ethanol | Hexane | N/A |
| Ethanol | Methyl t-butyl ether | N/A |
| Ethanol | Water | Form VI |
| Isopropyl alcohol | Heptane | Form II |
| Isopropyl alcohol | Hexane | Form II |
| Isopropyl alcohol | Methyl t-butyl ether | N/A |
| Isopropyl alcohol | Water | N/A |

Quench Cooling Screen

Saturated solutions of the compound of Formula I (from Example I) were prepared at 30-50° C. and quench cooled to about −15° C. to induce precipitation. Results of the screen are presented below in Table 9. The entry "N/A" means that either the sample contained only clear solution or the amount of solid was too small to be analyzed by XRPD.

TABLE 9

Quench Cooling Results.

| Solvent | Form |
|---|---|
| Acetonitrile | N/A |
| Methyl isobutyl ketone | N/A |
| Toluene | Form IV |
| n-Butanol | N/A |
| Methyl t-butyl ether | N/A |
| Ethanol | N/A |
| Ethyl acetate | N/A |
| Ethyl formate | N/A |
| Isobutyl acetate | N/A |
| Isopropyl acetate | N/A |

TABLE 9-continued

Quench Cooling Results.

| Solvent | Form |
| --- | --- |
| 1-Propanol | N/A |
| Isopropyl alcohol | Form II |

Saturated Solution Heating and Cooling Cycle Screen

Saturated solutions (about 3 mL) of the compound of Formula I (from Example 1) were prepared at 30 to 50° C. and cooled slowly using a programmed circulating bath to form a slurry of solvent and precipitate. This slurry was then heated to 50° C. over 2 hours and then cooled down to 5° C. over 2 hours. The process was repeated overnight and the solid was isolated for further analysis. The results are presented in Table 10. The entry "N/A" means that either the sample contained only clear solution or the amount of solid was too small to be analyzed by XRPD.

TABLE 10

Heating and Cooling Cycle Results.

| Solvent | Form |
| --- | --- |
| Acetonitrile | N/A |
| Chloroform | N/A |
| Methylene chloride | Form I |
| Dimethylformamide | N/A |
| 1,4-Dioxane | N/A |
| Methanol | N/A |
| 2-Methoxyethanol | N/A |
| Methyl isobutyl ketone | Form VII |
| Toluene | Form X |
| Hexane | Amorphous + solid |
| Tetrahydrofuran | N/A |
| Acetone | Form X |
| n-Butanol | N/A |
| Methyl t-butyl ether | N/A |
| Dimethylsulfoxide | N/A |
| Ethanol | N/A |
| Ethyl acetate | Form I |
| Ethyl formate | N/A |
| Isobutyl acetate | Form XI |
| Isopropyl acetate | Form II |
| 1-Propanol | N/A |
| Isopropyl alcohol | Form II |
| Water | Form VI |
| Methyl ethyl ketone | Form I |

Example 3

Experiments Related to Stability of the Crystalline Forms

Competitive Slurry Experiment in Methanol-Ethyl Acetate at Elevated Temperature

Forms I and X of the compound of Formula I were slurried together in a methanol-ethyl acetate (1:10) solvent system and heated at 50° C. for 5 days. Specifically, 5 mL of ethyl acetate and 0.5 mL of methanol were combined and heated to 50° C. Form I (from Example 1) was added to the solvent mixture until a cloudy solution formed (about 156 mg), and then additional Form I was added (about 50 mg). Then 50 mg of Form X (prepared as described in Example 12) was added. The mixture was stirred at 50° C. for 5 days and the solid was characterized and monitored by XRPD. The resulting crystalline form was predominantly Form I with other minor forms detected.

Competitive Slurry Experiment of all Forms in Methanol-Acetate at Room Temperature Forms I to XIII of the compound of Formula I were slurried together in a methanol-ethyl acetate (1:10) solvent system at room temperature for 8 days. Specifically, 10 mg of Form I (from Example 1) was added to 1 mL of ethyl acetate with stirring. Then 0.1 mL of methanol was added giving a cloudy solution to which 3 mg of additional Form I (from Example 1) was added. About 3 mg each of the other crystalline Forms II to XIII, prepared according to the chart below, were then added and the resulting slurry was stirred for 8 days and the solids characterized by XRPD. The resulting crystalline form detected after 8 days was predominantly Form I.

Methods of preparation for Forms II to XIII.

| Form | Preparation |
| --- | --- |
| Form II | To 2 mL of saturated solution of Form I in IPA was added about 30 mg of additional Form I followed by stirring at 50 ± 1° C. For 3 days. The solid was centrifuged and characterized by XRPD as Form II. |
| Form III | To 2 mL of saturated solution of Form I in IPAc was added about 30 mg of additional Form I followed by stirring at 50 ± 1° C. For 3 days. The solid was centrifuged and characterized by XRPD as Form III. |
| Form IV | To 2 mL of saturated solution of Form I in toluene was added about 30 mg of additional Form I followed by stirring at 25 ± 1° C. For 3 days. The solid was centrifuged and characterized by XRPD as Form IV. |
| Form V | To 2 mL of saturated solution of Form I in isobutyl acetate was added about 30 mg of additional Form I followed by stirring at 25 ± 1° C. For 3 days. The solid was centrifuged and characterized by XRPD as Form V. |
| Form VI | To 2 mL of saturated solution of Form I in water was added about 30 mg of additional Form I followed by stirring at 25 ± 1° C. For 3 days. The solid was isolated by centrifugation and characterized by XRPD as Form VI. |
| Form VII | To 2 mL of saturated solution of Form I in 1,4-dioxane was added about 30 mg of additional Form I followed by stirring at 25 ± 1° C. For 3 days. The solid was centrifuged and characterized by XRPD as Form VII. |
| Form VIII | Approximately 2 mL of saturated solution of Form I in n-butanol were evaporated under air without stirring at 50 ± 1° C. to give solid, which was characterized by XRPD as Form VIII. |
| Form IX | To 2 mL of saturated solution of Form I in MIBK was added about 30 mg of additional Form I followed by stirring at 50 ± 1° C. For 3 days. The solid was centrifuged and characterized by XRPD as Form IX. |
| Form X | To 2 mL of saturated solution of Form I in acetone was added about 30 mg of additional Form I followed by stirring at 50 ± 1° C. For 3 days. The solid was isolated by centrifugation and characterized by XRPD as Form X. |
| Form XI | Approximately 3 mL of saturated solutions Form I in isobutyl acetate was prepared at 30° C. to 50° C. and cooled to 25° C. in a bath slowly by using a programmed circulating bath. The formed solution was heated to 50° C. over 2 hours and then cooled to 5° C. over 2 hours. This process was repeated for 76 hrs and the solid was isolated by centrifugation and analyzed by XRPD as Form XI. |
| Form XII | To 2 mL of saturated solution of Form I in MTBE was added about 30 mg of additional Form I followed by stirring at 50 ± 1° C. For 3 days. The solid was centrifuged and characterized by XRPD as Form XII. |
| Form XIII | Approximately 2 mL of saturated solution of Form I in 2-methoxyethanol were evaporated under air without stirring at 50 ± 1° C. to give solid, which was characterized by XRPD as Form XIII. |

Competitive Slurry Experiment in Acetone at Elevated Temperature

Forms I and X of the compound of Formula I were slurried together in acetone and heated at 50° C. overnight. Specifically, 5 mL of acetone was heated to 50° C. Form I (from Example 1) was added to the solvent mixture until a cloudy solution formed (about 190 mg), and then additional Form I was added (about 50 mg). Then 50 mg of Form X (prepared as described in Example 12) was added. The mixture was stirred at 50° C. overnight and the solid was characterized and monitored by XRPD. The resulting crystalline form was predominantly Form X. Thus, Form I can be converted to Form X under certain conditions.

Competitive Slurry Experiment in Acetone at Room Temperature

Forms I to XIII of the compound of Formula I were slurried together in acetone at room temperature for 11 days. Specifically, 1 mL of acetone was combined with 11.2 mg of Form I (from Example 1) at room temperature to give a clear solution, and then additional Form I was added (about 10 mg) to give a slurry. Then 0.5 mL of acetone was added to give a cloudy solution. Then about 2 mg each of Forms II-XIII (see above chart) were added. The mixture was stirred at room temperature for 11 days and the resulting solid was characterized and monitored by XRPD. The resulting crystalline form was predominantly Form I with other minor forms also detected.

Example 4

Preparation and Characterization of Form II

Form II was prepared as follows. To 0.5 mL of saturated solution of Form I in IPA was added 2.5 mL of heptane followed by stirring to give a solid, which was analyzed by XRPD as Form II.

The XRPD for Form II is provided in FIG. 5 and a list of corresponding peaks is provided in Table 11 below.

TABLE 11

XRPD Peaks for Form II.

| 2-Theta | Height | H % |
|---------|--------|------|
| 4.0 | 277 | 11.1 |
| 7.2 | 262 | 10.5 |
| 9.2 | 405 | 16.2 |
| 11.1 | 330 | 13.2 |
| 12.0 | 106 | 4.2 |
| 14.8 | 1296 | 51.7 |
| 15.8 | 500 | 20 |
| 16.7 | 59 | 2.4 |
| 18.5 | 1927 | 77 |
| 19.3 | 2504 | 100 |
| 20.3 | 82 | 3.3 |
| 20.8 | 604 | 24.1 |
| 21.7 | 533 | 21.3 |
| 22.5 | 296 | 11.8 |
| 22.8 | 1243 | 49.6 |
| 23.1 | 376 | 15 |
| 23.8 | 142 | 5.7 |
| 24.5 | 224 | 9 |
| 25.0 | 246 | 9.8 |
| 25.6 | 780 | 31.1 |
| 26.5 | 90 | 3.6 |
| 27.8 | 454 | 18.1 |
| 28.3 | 273 | 10.9 |
| 28.7 | 370 | 14.8 |
| 29.5 | 66 | 2.6 |
| 30.3 | 128 | 5.1 |
| 30.7 | 156 | 6.2 |
| 31.4 | 122 | 4.9 |
| 32.4 | 144 | 5.8 |
| 34.6 | 238 | 9.5 |
| 35.9 | 70 | 2.8 |
| 36.6 | 154 | 6.1 |
| 37.5 | 60 | 2.4 |

The TGA of Form II is provided in FIG. 6. The sample showed about 0.1% weight loss up to 100° C., and about 11% weight loss between 100 and 200° C.

Example 5

Preparation and Characterization of Form III

Form III was prepared as follows. To 2 mL of saturated solution of Form I in IPAc was added about 30 mg of additional Form I followed by stirring at 50±1° C. For 3 days. The solid was centrifuged and characterized by XRPD as Form III.

The XRPD spectrum for Form III is provided in FIG. 7 and a list of corresponding peaks is provided in Table 12 below

TABLE 12

XRPD Peaks for Form III.

| 2-Theta | Height | H % |
|---------|--------|------|
| 3.8 | 284 | 3.8 |
| 10.9 | 3624 | 48.5 |
| 11.3 | 1016 | 13.6 |
| 12.3 | 1027 | 13.7 |
| 13.9 | 885 | 11.8 |
| 14.9 | 495 | 6.6 |
| 15.7 | 716 | 9.6 |
| 17.8 | 621 | 8.3 |
| 18.6 | 1087 | 14.5 |
| 19.5 | 643 | 8.6 |
| 20.1 | 753 | 10.1 |
| 21.0 | 1183 | 15.8 |
| 21.8 | 7476 | 100 |
| 22.7 | 1177 | 15.7 |
| 23.1 | 795 | 10.6 |
| 24.6 | 1972 | 26.4 |
| 25.1 | 1272 | 17 |
| 25.8 | 65 | 0.9 |
| 26.6 | 434 | 5.8 |
| 27.2 | 816 | 10.9 |
| 27.8 | 53 | 0.7 |
| 28.4 | 1070 | 14.3 |
| 28.9 | 206 | 2.8 |
| 30.3 | 239 | 3.2 |
| 31.7 | 436 | 5.8 |
| 32.1 | 184 | 2.5 |
| 33.0 | 618 | 8.3 |
| 33.5 | 75 | 1 |
| 38.8 | 239 | 3.2 |
| 39.1 | 423 | 5.7 |

Two DSC thermograms for Form III are provided in FIG. 8. The first is an initial cycle showing an endotherm with a maximum at about 133° C. The second is a thermogram of the sample after it had already been heated to 250° C., and it shows an endotherm with a peak maximum at about 241° C.

The TGA thermogram for Form III is provided in FIG. 9. Form III shows 0.2% weight loss up to 100° C., and 19% weight loss between 100 and 200° C.

Example 6

Preparation and Characterization of Form IV

Form IV was prepared as follows. To 2 mL of saturated solution of Form I in toluene was added about 30 mg of additional Form I followed by stirring at 50±1° C. For 3 days. The solid was centrifuged and characterized by XRPD as Form IV.

The XRPD for Form IV is shown in FIG. 10 and a list of corresponding peaks is provided in Table 13 below.

TABLE 13

XRPD Peaks for Form IV.

| 2-Theta | Height | H % |
| --- | --- | --- |
| 5.9 | 358 | 31 |
| 8.8 | 940 | 81.5 |
| 9.2 | 564 | 48.9 |
| 10.5 | 86 | 7.5 |
| 11.8 | 133 | 11.5 |
| 12.4 | 74 | 6.4 |
| 13.4 | 211 | 18.3 |
| 14.4 | 241 | 20.9 |
| 15.3 | 301 | 26.1 |
| 17.7 | 1090 | 94.5 |
| 19.5 | 207 | 18 |
| 23.6 | 1153 | 100 |
| 24.5 | 140 | 12.1 |
| 25.0 | 203 | 17.6 |
| 26.4 | 724 | 62.8 |
| 26.8 | 867 | 75.2 |
| 27.7 | 127 | 11 |
| 29.6 | 587 | 50.9 |

Two DSC thermograms are shown in FIG. 11 that are representative of Form IV, The first is an initial cycle showing an endothermic event having a maximum at about 153° C. The second thermocycle represents Form IV after it had been heated to 250° C. An endotherm with a maximum at about 149° C. is shown.

A TGA thermogram representative of Form IV is shown in FIG. 12. The sample showed 3.4% weight loss up to 100° C., and 8.4% weight loss between 100 and 200° C.

Example 7

Preparation and Characterization of Form V

Form V was prepared as follows. To 2 mL of saturated solution of Form I in isobutyl acetate was added about 30 mg of additional Form I followed by stirring at 25±1° C. For 3 days. The solid was centrifuged and characterized by XRPD as Form V.

The XRPD pattern for Form V is shown in FIG. 13 and a list of corresponding peaks is provided in Table 14 below.

TABLE 14

XRPD Peaks for Form V.

| 2-Theta | Height | H % |
| --- | --- | --- |
| 3.4 | 122 | 3.4 |
| 10.6 | 331 | 9.2 |
| 11.1 | 663 | 18.5 |
| 12.0 | 1191 | 33.3 |
| 13.6 | 716 | 20 |
| 14.6 | 261 | 7.3 |
| 15.4 | 670 | 18.7 |
| 15.7 | 232 | 6.5 |
| 17.5 | 2351 | 65.7 |
| 18.4 | 960 | 26.8 |
| 19.3 | 926 | 25.9 |
| 19.9 | 1185 | 33.1 |
| 20.8 | 1033 | 28.8 |
| 21.3 | 460 | 12.8 |
| 21.6 | 347 | 9.7 |
| 22.4 | 1573 | 43.9 |
| 22.9 | 3581 | 100 |
| 24.2 | 371 | 10.4 |
| 24.8 | 1263 | 35.3 |
| 26.4 | 655 | 18.3 |
| 27.0 | 729 | 20.4 |
| 28.0 | 371 | 10.4 |
| 28.6 | 893 | 24.9 |
| 29.8 | 1092 | 30.5 |
| 31.3 | 183 | 5.1 |
| 33.3 | 81 | 2.3 |
| 34.3 | 398 | 11.1 |
| 34.9 | 96 | 2.7 |
| 35.6 | 132 | 3.7 |
| 36.6 | 305 | 8.5 |
| 37.3 | 85 | 2.4 |
| 38.4 | 219 | 6.1 |

Two DSC thermograms are shown in FIG. 14 that are representative of Form V. The first thermogram represents an initial DSC cycle that is characterized by an endothermic peak maximum at about 121° C. The second thermogram represents a further DSC cycle carried out after the sample had already been heated to 250° C., showing an endothermic peak maximum at about 242° C.

A TGA thermogram representative of Form V is shown in FIG. 15. The sample showed about 0.2% weight loss up to 100° C. and about 21% weight loss between 100 and 200° C.

Example 8

Preparation and Characterization of Form VI

Form VI was prepared by combining about 1.0 g of the compound of Formula I (from Example 1) with 17 mL of water and then heating the resulting slurry at 50° C. with stirring for 3 days. The predominant crystalline form that was detected was Form VI based on characterization of the resulting solid by XRPD. The XRPD spectrum for Form VI is provided in FIG. 16 and the corresponding peak data is provided below in Table 15.

TABLE 15

XRPD Peak Data for Form VI.

| 2-Theta | Height | H % |
| --- | --- | --- |
| 3.5 | 173 | 8.8 |
| 3.8 | 172 | 8.7 |
| 10.7 | 879 | 44.6 |
| 13.2 | 119 | 6.1 |
| 13.8 | 205 | 10.4 |
| 14.6 | 1199 | 60.8 |
| 15.8 | 423 | 21.5 |
| 16.0 | 762 | 38.7 |
| 16.7 | 505 | 25.6 |
| 17.8 | 577 | 29.3 |
| 19.1 | 1176 | 59.7 |
| 19.9 | 145 | 7.4 |
| 20.8 | 302 | 15.3 |
| 21.3 | 187 | 9.5 |
| 22.4 | 727 | 36.9 |
| 23.9 | 1971 | 100 |
| 24.5 | 633 | 32.1 |
| 25.0 | 303 | 15.4 |
| 25.5 | 172 | 8.7 |
| 26.7 | 902 | 45.8 |
| 27.8 | 117 | 5.9 |
| 28.3 | 94 | 4.8 |
| 29.1 | 942 | 47.8 |
| 29.4 | 203 | 10.3 |
| 30.3 | 1369 | 69.5 |
| 31.9 | 118 | 6 |
| 32.5 | 363 | 18.4 |
| 33.4 | 121 | 6.2 |
| 34.7 | 448 | 22.7 |
| 35.7 | 98 | 5 |

TABLE 15-continued

XRPD Peak Data for Form VI.

| 2-Theta | Height | H % |
| --- | --- | --- |
| 35.9 | 129 | 6.6 |
| 36.9 | 241 | 12.2 |
| 38.0 | 173 | 8.8 |
| 39.5 | 114 | 5.8 |
| 40.4 | 170 | 8.6 |
| 41.3 | 140 | 7.1 |

The DSC data for Form VI is provided in FIG. 17, showing the initial DSC thermogram and a second DSC thermogram after the sample had been heated to 250° C. The initial DSC thermogram showed multiple endotherms with major peaks at about 134° C. and about 167° C. The second DSC thermogram showed a single endotherm with a sharp peak maximum at about 242° C., indicating that the heating of Form VI can result in a different solid form.

The TGA data for Form VI is provided in FIG. 18 and shows 2.6% weight loss up to about 100° C. and an additional weight loss of 1.3% between 100° C. and 250° C. The TGA data indicates that Form VI is likely a hydrated crystalline form of the compound of Formula I, potentially a hemihydrate.

Example 9

Preparation and Characterization of Form VII

Form VII was prepared as follows. To 2 mL of saturated solution of Form I in 1,4-dioxane was added about 30 mg of additional Form I followed by stirring at 25±1° C. For 3 days. The solid was centrifuged and characterized by XRPD as Form VII.

The XRPD spectrum for Form VII is provided in FIG. 19 and the corresponding peak data is provided below in Table 16.

TABLE 16

XRPD Peak Data for Form VII.

| 2-Theta | Height | H % |
| --- | --- | --- |
| 3.6 | 151 | 7.3 |
| 8.8 | 230 | 11.1 |
| 11.0 | 252 | 12.2 |
| 12.0 | 537 | 26.1 |
| 14.4 | 200 | 9.7 |
| 15.1 | 761 | 36.9 |
| 15.8 | 446 | 21.7 |
| 16.2 | 535 | 26 |
| 17.8 | 2059 | 100 |
| 18.5 | 817 | 39.7 |
| 19.5 | 930 | 45.1 |
| 19.9 | 261 | 12.7 |
| 21.5 | 199 | 9.7 |
| 22.1 | 663 | 32.2 |
| 23.2 | 108 | 5.2 |
| 24.0 | 547 | 26.6 |
| 24.6 | 1655 | 80.4 |
| 25.3 | 230 | 11.2 |
| 25.9 | 1192 | 57.9 |
| 26.7 | 108 | 5.3 |
| 27.9 | 298 | 14.5 |
| 29.0 | 155 | 7.5 |
| 29.5 | 155 | 7.5 |
| 30.5 | 429 | 20.8 |
| 30.8 | 255 | 12.4 |
| 31.9 | 307 | 14.9 |
| 32.9 | 146 | 7.1 |
| 33.7 | 341 | 16.6 |

TABLE 16-continued

XRPD Peak Data for Form VII.

| 2-Theta | Height | H % |
| --- | --- | --- |
| 34.1 | 55 | 2.7 |
| 34.7 | 63 | 3.1 |
| 39.6 | 208 | 10.1 |
| 40.5 | 93 | 4.5 |

The TGA thermogram for Form VII is provided in FIG. 20 and shows about 0.02% weight loss up to 100° C., and about 11% weight loss between 100 and 200° C.

Two DSC thermograms for Form VII are shown in FIG. 21. Cycle 1 shows the initial thermogram with an endothermic peak having a maximum at about 123° C. Cycle 2 shows the thermogram after the sample had been heated to 250° C., and shows an endothermic event having a maximum at about 257° C.

Example 10

Preparation and Characterization of Form VIII

Form VIII was prepared as follows. Approximately 2 mL of saturated solution of Form I in n-butanol were evaporated under air without stirring at 50±1° C. to give solid, which was characterized by XRPD as Form VIII.

The XRPD spectrum for Form VIII is provided in FIG. 22 and the corresponding peak data is provided below in Table 17.

TABLE 17

XRPD Peak Data for Form VIII.

| 2-Theta | Height | H % |
| --- | --- | --- |
| 3.9 | 279 | 15.1 |
| 7.3 | 158 | 8.6 |
| 8.2 | 431 | 23.3 |
| 10.9 | 1034 | 55.9 |
| 11.7 | 956 | 51.7 |
| 12.5 | 240 | 13 |
| 14.4 | 658 | 35.6 |
| 15.4 | 177 | 9.6 |
| 16.0 | 554 | 30 |
| 16.5 | 332 | 18 |
| 17.5 | 1051 | 56.9 |
| 18.2 | 373 | 20.2 |
| 18.5 | 535 | 28.9 |
| 19.4 | 270 | 14.6 |
| 19.7 | 1005 | 54.4 |
| 20.1 | 274 | 14.8 |
| 21.5 | 1679 | 90.8 |
| 22.6 | 1848 | 100 |
| 23.3 | 102 | 5.5 |
| 25.0 | 310 | 16.8 |
| 25.3 | 619 | 33.5 |
| 26.0 | 217 | 11.8 |
| 26.8 | 488 | 26.4 |
| 27.7 | 208 | 11.2 |
| 28.0 | 382 | 20.7 |
| 28.8 | 127 | 6.9 |
| 29.4 | 269 | 14.6 |
| 30.0 | 238 | 12.9 |
| 30.8 | 353 | 19.1 |
| 31.4 | 93 | 5 |
| 36.5 | 62 | 3.4 |
| 37.3 | 187 | 10.1 |
| 37.9 | 83 | 4.5 |

Two DSC thermograms for Form VIII are shown in FIG. 23. Cycle 1 shows the initial thermogram with an endothermic peak having a maximum at about 176° C. Cycle 2 shows the thermogram after the sample had been heated to 250° C.

The TGA thermogram for Form VIII is provided in FIG. 24 and shows about 0.4% weight loss up to 100° C. and other thermal events.

Example 11

Preparation and Characterization of Form IX

Form IX was prepared as follows. To 2 mL of saturated solution of Form I in MIBK was added about 30 mg of additional Form I followed by stirring at 50±1° C. For 3 days. The solid was centrifuged and characterized by XRPD as Form IX.

The XRPD spectrum for Form IX is provided in FIG. 25 and the corresponding peak data is provided below in Table 18.

TABLE 18

XRPD Peak Data for Form IX.

| 2-Theta | Height | H % |
|---|---|---|
| 3.9 | 264 | 9.8 |
| 11.1 | 1022 | 38 |
| 12.2 | 1363 | 50.7 |
| 13.8 | 809 | 30.1 |
| 14.9 | 160 | 6 |
| 15.5 | 595 | 22.2 |
| 15.9 | 159 | 5.9 |
| 17.4 | 1802 | 67.1 |
| 17.7 | 763 | 28.4 |
| 18.6 | 1129 | 42 |
| 19.3 | 1516 | 56.4 |
| 19.9 | 895 | 33.3 |
| 20.9 | 1113 | 41.4 |
| 21.7 | 823 | 30.6 |
| 22.4 | 1294 | 48.2 |
| 22.8 | 2687 | 100 |
| 24.4 | 971 | 36.1 |
| 24.8 | 2652 | 98.7 |
| 25.6 | 99 | 3.7 |
| 26.2 | 191 | 7.1 |
| 26.8 | 386 | 14.4 |
| 27.3 | 498 | 18.5 |
| 28.4 | 848 | 31.6 |
| 29.0 | 92 | 3.4 |
| 29.6 | 581 | 21.6 |
| 30.0 | 338 | 12.6 |
| 31.3 | 347 | 12.9 |
| 31.6 | 254 | 9.5 |
| 32.2 | 85 | 3.2 |
| 34.0 | 429 | 16 |
| 35.0 | 231 | 8.6 |
| 35.9 | 137 | 5.1 |
| 36.4 | 299 | 11.1 |
| 37.4 | 113 | 4.2 |
| 38.2 | 193 | 7.2 |
| 39.1 | 164 | 6.1 |
| 43.5 | 191 | 7.1 |

A DSC thermogram for Form IX is shown in FIG. 26. The thermogram is characterized by an endothermic event having a maximum at about 258° C.

The TGA thermogram for Form IX is provided in FIG. 27 and shows about 0.03% weight loss up to 100° C. and about 18% weight loss between 100 and 200° C.

Example 12

Preparation and Characterization of Form X

Form X was prepared by heating a slurry of Form I (from Example 1) in acetone at 50° C. for 2.5 days. Specifically, 1.06 g of the compound of Formula I was combined at 50° C. with 16 mL of acetone to give a slurry. The temperature of the mixture was maintained at 50° C. for 2.5 days. XRPD confirmed the presence of Form X.

The XRPD spectrum for Form X is provided in FIG. 28 and the corresponding peak data is provided below in Table 19.

TABLE 19

XRPD Peak Data for Form X.

| 2-Theta | Height | H % |
|---|---|---|
| 3.9 | 282 | 12.3 |
| 4.2 | 232 | 10.1 |
| 6.8 | 821 | 35.8 |
| 9.8 | 80 | 3.5 |
| 10.5 | 375 | 16.4 |
| 12.5 | 64 | 2.8 |
| 13.5 | 844 | 36.8 |
| 14.8 | 800 | 34.9 |
| 15.4 | 332 | 14.5 |
| 17.0 | 784 | 34.2 |
| 18.0 | 136 | 5.9 |
| 18.6 | 351 | 15.3 |
| 19.3 | 328 | 14.3 |
| 19.6 | 776 | 33.8 |
| 20.2 | 1021 | 44.5 |
| 21.2 | 154 | 6.7 |
| 21.7 | 2293 | 100 |
| 22.5 | 76 | 3.3 |
| 23.8 | 240 | 10.5 |
| 25.0 | 1076 | 46.9 |
| 25.4 | 139 | 6.1 |
| 26.3 | 1149 | 50.1 |
| 27.1 | 58 | 2.5 |
| 28.0 | 155 | 6.7 |
| 28.3 | 181 | 7.9 |
| 29.6 | 758 | 33 |
| 30.7 | 132 | 5.8 |
| 31.1 | 83 | 3.6 |

The DSC thermogram for Form X is shown in FIG. 29 and is characterized by an endotherm having a maximum at about 258° C.

The TGA thermograpm for Form X is shown in FIG. 30 and shows about 0.06% weight loss up to 100° C.

Example 13

Preparation and Characterization of Form XI

Form XI was prepared as follows. Approximately 3 mL of saturated solutions Form I in isobutyl acetate was prepared at 30° C. to 50° C. and cooled to 25° C. in a bath slowly by using a programmed circulating bath. The formed solution was heated to 50° C. over 2 hours and then cooled to 5° C. over 2 hours. This process was repeated for 76 hrs and the solid was isolated by centrifugation and analyzed by XRPD as Form XI.

The XRPD spectrum for Form XI is provided in FIG. 31 and the corresponding peak data is provided below in Table 20.

TABLE 20

XRPD Peak Data for Form XI.

| 2-Theta | Height | H % |
|---|---|---|
| 3.8 | 309 | 8.1 |
| 5.8 | 289 | 7.6 |
| 7.0 | 266 | 7 |
| 7.7 | 3775 | 99 |
| 11.7 | 198 | 5.2 |
| 12.4 | 559 | 14.7 |

TABLE 20-continued

XRPD Peak Data for Form XI.

| 2-Theta | Height | H % |
|---|---|---|
| 13.0 | 112 | 2.9 |
| 15.5 | 78 | 2.1 |
| 16.6 | 693 | 18.2 |
| 17.6 | 177 | 4.6 |
| 17.9 | 477 | 12.5 |
| 18.6 | 359 | 9.4 |
| 19.3 | 86 | 2.3 |
| 20.3 | 2474 | 64.9 |
| 21.3 | 183 | 4.8 |
| 22.0 | 155 | 4.1 |
| 22.9 | 238 | 6.2 |
| 23.4 | 3813 | 100 |
| 24.2 | 1326 | 34.8 |
| 24.8 | 270 | 7.1 |
| 26.3 | 950 | 24.9 |
| 27.1 | 172 | 4.5 |
| 28.1 | 81 | 2.1 |
| 29.2 | 175 | 4.6 |
| 29.9 | 713 | 18.7 |
| 31.4 | 312 | 8.2 |
| 31.9 | 299 | 7.8 |

Two DSC thermograms are shown in FIG. 32, that are representative of Form XI. The first thermogram is characterized by an endothermic event having a maximum at about 117° C. The second thermogram represents a further DSC cycle carried out after the sample had already been heated to 250° C., showing an endothermic peak maximum at about 243° C.

Example 14

Preparation and Characterization of Form XII

Form XII was prepared as follows. To 2 mL of saturated solution of Form I in MTBE was added about 30 mg of additional Form I followed by stirring at 50±1° C. For 3 days. The solid was centrifuged and characterized by XRPD as Form XII.

The XRPD spectrum for Form XII is provided in FIG. 33 and the corresponding peak data is provided below in Table 21.

TABLE 21

XRPD Peak Data for Form XII.

| 2-Theta | Height | H % |
|---|---|---|
| 3.8 | 83 | 5.7 |
| 6.0 | 147 | 10.1 |
| 7.8 | 1131 | 77.3 |
| 9.7 | 131 | 9 |
| 11.9 | 113 | 7.7 |
| 12.6 | 392 | 26.8 |
| 14.7 | 210 | 14.3 |
| 15.2 | 306 | 21 |
| 16.6 | 559 | 38.2 |
| 18.2 | 865 | 59.1 |
| 18.8 | 185 | 12.6 |
| 19.3 | 85 | 5.8 |
| 20.1 | 889 | 60.8 |
| 22.1 | 83 | 5.7 |
| 23.0 | 146 | 10 |
| 23.7 | 1463 | 100 |
| 25.0 | 140 | 9.6 |
| 25.9 | 187 | 12.8 |
| 27.3 | 120 | 8.2 |
| 29.5 | 354 | 24.2 |
| 29.8 | 273 | 18.7 |
| 30.7 | 109 | 7.4 |

TABLE 21-continued

XRPD Peak Data for Form XII.

| 2-Theta | Height | H % |
|---|---|---|
| 31.4 | 93 | 6.4 |
| 34.3 | 56 | 3.8 |
| 34.8 | 113 | 7.7 |

A DSC thermogram for Form XII is shown in FIG. 34. The thermogram is characterized by an endothermic event having a maximum at about 137° C.

Example 15

Preparation and Characterization of Form XIII

Form XIII was prepared as follows. Approximately 2 mL of saturated solution of Form I in 2-methoxyethanol were evaporated under air without stirring at 50±1° C. to give solid, which was characterized by XRPD as Form XIII The XRPD spectrum for Form XIII is provided in FIG. 35 and the corresponding peak data is provided below in Table 22.

TABLE 22

XRPD Peak Data for Form XIII.

| 2-Theta | Height | H % |
|---|---|---|
| 3.8 | 302 | 30.9 |
| 5.9 | 845 | 86.5 |
| 7.7 | 112 | 11.5 |
| 10.1 | 977 | 100 |
| 11.3 | 231 | 23.6 |
| 11.7 | 238 | 24.3 |
| 13.0 | 717 | 73.3 |
| 14.2 | 103 | 10.5 |
| 14.8 | 153 | 15.7 |
| 16.2 | 375 | 38.3 |
| 16.9 | 564 | 57.7 |
| 17.8 | 237 | 24.3 |
| 18.5 | 116 | 11.9 |
| 19.4 | 188 | 19.2 |
| 20.4 | 153 | 15.7 |
| 21.0 | 207 | 21.1 |
| 21.6 | 64 | 6.6 |
| 22.6 | 559 | 57.2 |
| 23.4 | 747 | 76.4 |
| 24.2 | 229 | 23.5 |
| 24.6 | 175 | 17.9 |
| 25.4 | 177 | 18.1 |
| 26.0 | 514 | 52.6 |
| 26.9 | 704 | 72.1 |
| 28.2 | 291 | 29.8 |
| 29.5 | 273 | 28 |
| 30.5 | 202 | 20.7 |

A DSC thermogram for Form XIII is shown in FIG. 36. The thermogram is characterized by an endothermic event having a maximum at about 156° C. and a second endotherm at about 238° C.

Example A1: PI3K Enzyme Assay

PI3-Kinase luminescent assay kit including lipid kinase substrate, D-myo-phosphatidylinositol 4,5-bisphosphate (PtdIns(4,5)P2)D (+)-sn-1,2-di-O-octanoylglyceryl, 3-O-phospho linked (PIP2), biotinylated I(1,3,4,5)P4, PI(3,4,5) P3 Detector Protein, is purchased from Echelon Biosciences (Salt Lake City, Utah). AlphaScreen™ GST Detection Kit including donor and acceptor beads is purchased from PerkinElmer Life Sciences (Waltham, Mass.). PI3Kδ

(p110δ/p85α) is purchased from Millipore (Bedford, Mass.). ATP, MgCl$_2$, DTT, EDTA, HEPES and CHAPS are purchased from Sigma-Aldrich (St. Louis, Mo.).

AlphaScreen™ Assay for PI3Kδ

The kinase reaction is conducted in 384-well REMP plate from Thermo Fisher Scientific in a final volume of 40 μL. Inhibitors are first diluted serially in DMSO and added to the plate wells before the addition of other reaction components. The final concentration of DMSO in the assay is 2%. The PI3K assays are carried out at room temperature in 50 mM HEPES, pH 7.4, 5 mM MgCl$_2$, 50 mM NaCl, 5 mM DTT and CHAPS 0.04%. Reactions are initiated by the addition of ATP, the final reaction mixture consists of 20 μM PIP2, 20 μM ATP, 1.2 nM PI3K$_6$ and are incubated for 20 min. 10 μL of reaction mixture is then transferred to 5 μL 50 nM biotinylated I(1,3,4,5)P4 in quench buffer: 50 mM HEPES pH 7.4, 150 mM NaCl, 10 mM EDTA, 5 mM DTT, 0.1% Tween-20, followed with the addition of 10 μL AlphaScreen™ donor and acceptor beads suspended in quench buffer containing 25 nM PI(3,4,5)P3 detector protein. The final concentration of both donor and acceptor beads is 20 mg/mL. After plate sealing, the plate is incubated in a dark location at room temperature for 2 hours. The activity of the product is determined on Fusion-alpha microplate reader (Perkin-Elmer). IC$_{50}$ determination is performed by fitting the curve of percent control activity versus the log of the inhibitor concentration using the GraphPad Prism 3.0 software.

Example A2: PI3K Enzyme Assay

Materials:

Lipid kinase substrate, phosphoinositol-4,5-bisphosphate (PIP2), is purchased from Echelon Biosciences (Salt Lake City, Utah). PI3K isoforms α, β, δ and γ are purchased from Millipore (Bedford, Mass.). ATP, MgCl$_2$, DTT, EDTA, MOPS and CHAPS are purchased from Sigma-Aldrich (St. Louis, Mo.).

The kinase reaction is conducted in clear-bottom 96-well plate from Thermo Fisher Scientific in a final volume of 24 μL. Inhibitors are first diluted serially in DMSO and added to the plate wells before the addition of other reaction components. The final concentration of DMSO in the assay is 0.5%. The PI3K assays are carried out at room temperature in 20 mM MOPS, pH 6.7, 10 mM MgCl$_2$, 5 mM DTT and CHAPS 0.03%. The reaction mixture is prepared containing 50 μM PIP2, kinase and varying concentration of inhibitors. Reactions are initiated by the addition of ATP containing 2.2 μCi [γ-$^{33}$P]ATP to a final concentration of 1000 μM. The final concentration of PI3K isoforms α, β, δ and γ in the assay are 1.3, 9.4, 2.9 and 10.8 nM respectively. Reactions are incubated for 180 min and terminated by the addition of 100 μL of 1 M potassium phosphate pH 8.0, 30 mM EDTA quench buffer. A 100 μL aliquot of the reaction solution is then transferred to 96-well Millipore MultiScreen IP 0.45 μm PVDF filter plate (The filter plate is pre-wetted with 200 μL 100% ethanol, distilled water, and 1 M potassium phosphate pH 8.0, respectively). The filter plate is aspirated on a Millipore Manifold under vacuum and washed with 18×200 μL wash buffer containing 1 M potassium phosphate pH 8.0 and 1 mM ATP. After drying by aspiration and blotting, the plate is air dried in an incubator at 37° C. overnight. Packard TopCount adapter (Millipore) is then attached to the plate followed with addition of 120 μL Microscint 20 scintillation cocktail (Perkin Elmer) in each well. After the plate sealing, the radioactivity of the product is determined by scintillation counting on Topcount (Perkin-Elmer). IC$_{50}$ determination is performed by fitting the curve of percent control activity versus the log of the inhibitor concentration using the GraphPad Prism 3.0 software. Compounds having and IC$_{50}$ value of 10 μM or less are considered active.

Example A3: PI3Kδ Scintillation Proximity Assay

Materials

[γ-33P]ATP (10 mCi/mL) is purchased from Perkin-Elmer (Waltham, Mass.). Lipid kinase substrate, D-myo-Phosphatidylinositol 4,5-bisphosphate (PtdIns(4,5)P2)D (+)-sn-1,2-di-O-octanoylglyceryl, 3-O-phospho linked (PIP2), CAS 204858-53-7, is purchased from Echelon Biosciences (Salt Lake City, Utah). PI3Kδ (p110δ/p85α) is purchased from Millipore (Bedford, Mass.). ATP, MgCl$_2$, DTT, EDTA, MOPS and CHAPS are purchased from Sigma-Aldrich (St. Louis, Mo.). Wheat Germ Agglutinin (WGA) YSi SPA Scintillation Beads is purchased from GE healthcare life sciences (Piscataway, N.J.).

The kinase reaction is conducted in polystyrene 384-well matrix white plate from Thermo Fisher Scientific in a final volume of 25 μL. Inhibitors are first diluted serially in DMSO and added to the plate wells before the addition of other reaction components. The final concentration of DMSO in the assay is 0.5%. The PI3K assays are carried out at room temperature in 20 mM MOPS, pH 6.7, 10 mM MgCl$_2$, 5 mM DTT and CHAPS 0.03%. Reactions are initiated by the addition of ATP, the final reaction mixture consisted of 20 μM PIP2, 20 μM ATP, 0.2 μCi [γ-$^{33}$P] ATP, 4 nM PI3Kδ. Reactions are incubated for 210 min and terminated by the addition of 40 μL SPA beads suspended in quench buffer: 150 mM potassium phosphate pH 8.0, 20% glycerol. 25 mM EDTA, 400 μM ATP. The final concentration of SPA beads is 1.0 mg/mL. After the plate sealing, plates are shaken overnight at room temperature and centrifuged at 1800 rpm for 10 minutes, the radioactivity of the product is determined by scintillation counting on Topcount (Perkin-Elmer). IC$_{50}$ determination is performed by fitting the curve of percent control activity versus the log of the inhibitor concentration using the GraphPad Prism 3.0 software.

Example B1: B Cell Proliferation Assay

To acquire B cells, human PBMC are isolated from the peripheral blood of normal, drug free donors by standard density gradient centrifugation on Ficoll-Hypague (GE Healthcare, Piscataway, N.J.) and incubated with anti-CD19 microbeads (Miltenyi Biotech, Auburn, Calif.). The B cells are then purified by positive immunosorting using an autoMacs (Miltenyi Biotech) according to the manufacturer's instruction.

The purified B cells (2×10$^5$/well/200 μL) are cultured in 96-well ultra-low binding plates (Corning, Corning, N.Y.) in RPMI1640, 10% FBS and goat F(ab')2 anti-human IgM (10 μg/ml) (Invitrogen, Carlsbad, Calif.), in the presence of different amount of test compounds, for three days. [$^3$H]-thymidine (1 μCi/well) (PerkinElmer, Boston, Mass.) in PBS is then added to the B cell cultures for an additional 12 hrs before the incorporated radioactivity is separated by filtration with water through GF/B filters (Packard Bioscience, Meriden, Conn.) and measured by liquid scintillation counting with a TopCount (Packard Bioscience). Compounds having an IC$_{50}$ value of 10 μM or less are considered active.

Example B2: Pfeiffer Cell Proliferation Assay

Pfeiffer cell line (diffuse large B cell lymphoma) is purchased from ATCC (Manassas, Va.) and maintained in the culture medium recommended (RPMI and 10% FBS). To measure the anti-proliferation activity of the PI3Kδ submittals, the Pfeiffer cells are plated with the culture medium ($2\times10^3$ cells/well/per 200 µl) into 96-well ultra-low binding plates (Corning, Corning, N.Y.), in the presence or absence of a concentration range of test compounds. After 3-4 days, [$^3$H]-thymidine (1 µCi/well) (PerkinElmer, Boston, Mass.) in PBS is then added to the cell culture for an additional 12 hrs before the incorporated radioactivity is separated by filtration with water through GF/B filters (Packard Bioscience, Meridenj, CT) and measured by liquid scintillation counting with a TopCount (Packard Bioscience).

Example C: Akt Phosphorylation Assay

Ramos cells (B lymphocyte from Burkitts lymphoma) can be obtained from ATCC (Manassas, Va.) and maintained in RPMI1640 and 10% FBS. The cells ($3\times10^7$ cells/tube/3 mL in RPMI) are incubated with different amounts of test compounds for 2 hrs at 37° C. and then stimulated with goat F(ab')2 anti-human IgM (5 µg/mL) (Invitrogen) for 17 min. in a 37° C. water bath. The stimulated cells are spun down at 4° C. with centrifugation and whole cell extracts prepared using 300 µL lysis buffer (Cell Signaling Technology, Danvers, Mass.). The resulting lysates are sonicated and supernatants are collected. The phosphorylation level of Akt in the supernatants are analyzed by using PathScan phospho-Akt1 (Ser473) sandwich ELISA kits (Cell Signaling Technology) according to the manufacturer's instruction.

Example D: In Vitro JAK Kinase Assay

The compounds in Table A were tested for inhibitory activity of JAK targets according to the following in vitro assay described in Park et al., *Analytical Biochemistry* 1999, 269, 94-104. The catalytic domains of human JAK1 (a.a. 837-1142), JAK2 (a.a. 828-1132) and JAK3 (a.a. 781-1124) were expressed using baculovirus in insect cells and purified. The catalytic activity of JAK1, JAK2 or JAK3 was assayed by measuring the phosphorylation of a biotinylated peptide. The phosphorylated peptide was detected by homogenous time resolved fluorescence (HTRF). $IC_{50}$s of compounds were measured for each kinase in the 40 µL reactions that contain the enzyme, ATP and 500 nM peptide in 50 mM Tris (pH 7.8) buffer with 100 mM NaCl, 5 mM DTT, and 0.1 mg/mL (0.01%) BSA. For the 1 mM $IC_{50}$ measurements, ATP concentration in the reactions was 1 mM. Reactions were carried out at room temperature for 1 hour and then stopped with 20 µL 45 mM EDTA, 300 nM SA-APC, 6 nM Eu-Py20 in assay buffer (Perkin Elmer, Boston, Mass.). Binding to the Europium labeled antibody took place for 40 minutes and HTRF signal was measured on a PHERA star plate reader (BMG, Cary, N.C.). The data for the JAK1 and/or JAK2 inhibitors were obtained by testing the compounds in the Example D assay at 1 mM ATP.

What is claimed is:

1. A method of treating a disease in a patient, wherein said disease is arthritis, myasthenia gravis, multiple sclerosis, or Sjoegren's syndrome, comprising administering to said patient a therapeutically effective amount of a crystalline form of the compound (S)-7-(1-(9H-purin-6-ylamino)ethyl)-6-(3-fluorophenyl)-3-methyl-5H-thiazolo[3,2-a]pyrimidin-5-one which is hydrated, or a crystalline form of the compound (S)-7-(1-(9H-purin-6-ylamino)ethyl)-6-(3-fluorophenyl)-3-methyl-5H-thiazolo[3,2-a]pyrimidin-5-one which is Form X.

2. A method of treating an immune-based disease in a patient, wherein said immune-based disease is rheumatoid arthritis, glomerulonephritis, lupus, inflammation related to rheumatoid arthritis, inflammation related to glomerulonephritis, or inflammation related to lupus, comprising administering to said patient a therapeutically effective amount of a crystalline form of the compound (S)-7-(1-(9H-purin-6-ylamino)ethyl)-6-(3-fluorophenyl)-3-methyl-5H-thiazolo[3,2-a]pyrimidin-5-one which is hydrated, or a crystalline form of the compound (S)-7-(1-(9H-purin-6-ylamino)ethyl)-6-(3-fluorophenyl)-3-methyl-5H-thiazolo[3,2-a]pyrimidin-5-one which is Form X.

3. A method of treating B cell lymphoma in a patient, comprising administering to said patient a therapeutically effective amount of a crystalline form of the compound (S)-7-(1-(9H-purin-6-ylamino)ethyl)-6-(3-fluorophenyl)-3-methyl-5H-thiazolo[3,2-a]pyrimidin-5-one which is hydrated, or a crystalline form of the compound (S)-7-(1-(9H-purin-6-ylamino)ethyl)-6-(3-fluorophenyl)-3-methyl-5H-thiazolo[3,2-a]pyrimidin-5-one which is Form X.

4. The method of claim 1, wherein the method comprises administering to said patient a therapeutically effective amount of a crystalline form of the compound (S)-7-(1-(9H-purin-6-ylamino)ethyl)-6-(3-fluorophenyl)-3-methyl-5H-thiazolo[3,2-a]pyrimidin-5-one which is hydrated.

5. The method of claim 4, wherein said disease is arthritis.

6. The method of claim 4, wherein said disease is myasthenia gravis.

7. The method of claim 4, wherein said disease is multiple sclerosis.

8. The method of claim 4, wherein said disease is Sjoegren's syndrome.

9. The method of claim 2, wherein the method comprises administering to said patient a therapeutically effective amount of a crystalline form of the compound (S)-7-(1-(9H-purin-6-ylamino)ethyl)-6-(3-fluorophenyl)-3-methyl-5H-thiazolo[3,2-a]pyrimidin-5-one which is hydrated.

10. The method of claim 9, wherein said immune-based disease is rheumatoid arthritis.

11. The method of claim 9, wherein said immune-based disease is glomerulonephritis.

12. The method of claim 9, wherein said immune-based disease is lupus.

13. The method of claim 9, wherein said immune-based disease is inflammation related to rheumatoid arthritis, inflammation related to glomerulonephritis, or inflammation related to lupus.

14. The method of claim 3, wherein the method comprises administering to said patient a therapeutically effective amount of a crystalline form of the compound (S)-7-(1-(9H-purin-6-ylamino)ethyl)-6-(3-fluorophenyl)-3-methyl-5H-thiazolo[3,2-a]pyrimidin-5-one which is hydrated.

15. The method of claim 14, wherein said B cell lymphoma is diffuse large B cell lymphoma.

16. The method of claim 14, wherein said B cell lymphoma is activated B-cell like (ABC) diffuse large B cell lymphoma.

17. The method of claim 14, wherein said B cell lymphoma is germinal center B cell (GCB) diffuse large B cell lymphoma.

18. The method of claim 1, wherein the method comprises administering to said patient a therapeutically effective amount of a crystalline form of the compound (S)-7-(1-(9H-purin-6-ylamino)ethyl)-6-(3-fluorophenyl)-3-methyl-5H-thiazolo[3,2-a]pyrimidin-5-one which is Form X.

19. The method of claim 18, wherein said disease is arthritis.

20. The method of claim 18, wherein said disease is myasthenia gravis.

21. The method of claim 18, wherein said disease is multiple sclerosis.

22. The method of claim 18, wherein said disease is Sjoegren's syndrome.

23. The method of claim 2, wherein the method comprises administering to said patient a therapeutically effective amount of a crystalline form of the compound (S)-7-(1-(9H-purin-6-ylamino)ethyl)-6-(3-fluorophenyl)-3-methyl-5H-thiazolo[3,2-a]pyrimidin-5-one which is Form X.

24. The method of claim 23, wherein said immune-based disease is rheumatoid arthritis.

25. The method of claim 23, wherein said immune-based disease is glomerulonephritis.

26. The method of claim 23, wherein said immune-based disease is lupus.

27. The method of claim 23, wherein said immune-based disease is inflammation related to rheumatoid arthritis, inflammation related to glomerulonephritis, or inflammation related to lupus.

28. The method of claim 3, wherein the method comprises administering to said patient a therapeutically effective amount of a crystalline form of the compound (S)-7-(1-(9H-purin-6-ylamino)ethyl)-6-(3-fluorophenyl)-3-methyl-5H-thiazolo[3,2-a]pyrimidin-5-one which is Form X.

29. The method of claim 28, wherein said B cell lymphoma is diffuse large B cell lymphoma.

30. The method of claim 28, wherein said B cell lymphoma is activated B-cell like (ABC) diffuse large B cell lymphoma.

31. The method of claim 28, wherein said B cell lymphoma is germinal center B cell (GCB) diffuse large B cell lymphoma.

* * * * *